(12) United States Patent
Cals et al.

(10) Patent No.: US 10,315,996 B2
(45) Date of Patent: Jun. 11, 2019

(54) ROR GAMMA (RORγ) MODULATORS

(71) Applicants: LEAD PHARMA HOLDING B.V., Nijmegen (NL); SANOFI, Paris (FR)

(72) Inventors: Joseph Maria Gerardus Barbara Cals, Oss (NL); Vera De Kimpe, Oss (NL); Sander Bernardus Nabuurs, Oss (NL)

(73) Assignees: LEAD PHARMA HOLDING B.V., Nijmegen (NL); SANOFI, Paris (FR)

( * ) Notice: Subject to any disclaimer, the term of this patent is extended or adjusted under 35 U.S.C. 154(b) by 0 days.

(21) Appl. No.: 15/579,111

(22) PCT Filed: Jun. 3, 2016

(86) PCT No.: PCT/EP2016/062688
§ 371 (c)(1),
(2) Date: Dec. 1, 2017

(87) PCT Pub. No.: WO2016/193452
PCT Pub. Date: Dec. 8, 2016

(65) Prior Publication Data
US 2018/0170877 A1    Jun. 21, 2018

(30) Foreign Application Priority Data
Jun. 5, 2015    (EP) .................... 15170762

(51) Int. Cl.
*C07C 311/20* (2006.01)
*C07C 317/44* (2006.01)
(Continued)

(52) U.S. Cl.
CPC .......... *C07D 213/75* (2013.01); *C07C 311/20* (2013.01); *C07C 317/44* (2013.01); *C07C 317/50* (2013.01); *C07D 207/06* (2013.01); *C07D 209/08* (2013.01); *C07D 211/16* (2013.01); *C07D 211/26* (2013.01); *C07D 211/60* (2013.01); *C07D 213/82* (2013.01); *C07D 215/08* (2013.01); *C07D 217/02* (2013.01); *C07D 223/16* (2013.01); *C07D 231/40* (2013.01); *C07D 241/04* (2013.01); *C07D 261/08* (2013.01); *C07D 277/46* (2013.01); *C07D 285/135* (2013.01); *C07D 295/13* (2013.01); *C07D 295/192* (2013.01); *C07D 307/52* (2013.01); *C07D 333/36* (2013.01); *C07D 417/04* (2013.01); *C07D 495/04* (2013.01); *C07C 2601/02* (2017.05); *C07C 2601/04* (2017.05)
(Continued)

(58) Field of Classification Search
CPC ............ C07C 2601/02; C07C 2601/04; C07C 311/20; C07C 317/44; C07C 317/50; C07D 207/06; C07D 209/08; C07D 211/16; C07D 211/26; C07D 211/60; C07D 213/75; C07D 213/82; C07D 215/08; C07D 217/02; C07D 223/16; C07D 231/40; C07D 241/04; C07D 261/08; C07D 277/46; C07D 285/135; C07D 295/13; C07D 295/192; C07D 307/52; C07D 333/36; C07D 417/04; C07D 495/04

See application file for complete search history.

(56) References Cited

FOREIGN PATENT DOCUMENTS

| WO | 2013/029338 A1 | 3/2013 |
| WO | 2013/171729 A2 | 11/2013 |
| WO | 2014/125426 A1 | 8/2014 |

OTHER PUBLICATIONS

Jul. 25, 2016 Search Report issued in International Patent Application No. PCT/EP2016/062688.
(Continued)

*Primary Examiner* — Sarah Pihonak
(74) *Attorney, Agent, or Firm* — Oliff PLC

(57) ABSTRACT

Compounds according to Formula I:

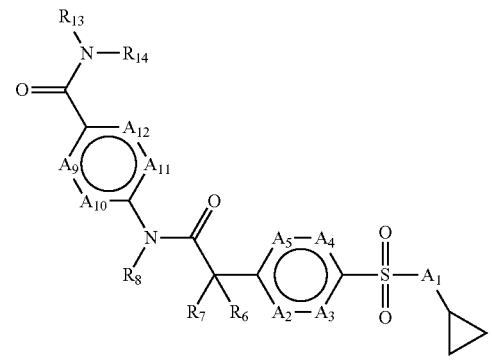

(Formula I)

or a pharmaceutically acceptable salt wherein: $A_1$ is $NR_1$ or $CR_1$, with $R_1$ herein; the cyclopropyl moiety with one or more methyl and one or more F; $A_2$-$A_5$ are N or $CR_2$-$CR_5$, with no more than two of the four positions A in $A_2$-$A_5$ can be simultaneously N; $R_2$-$R_5$ are described; $R_6$ and $R_7$ are independently H, F, methyl, ethyl, hydroxyl or methoxy or $R_6$ and $R_7$ together is carbonyl, all alkyl groups, if substituted with one or more F; $R_8$ is H or C(1-6)alkyl; $A_9$-$A_{12}$ are N or $CR_9$-$CR_{12}$, with no more than two of the four positions A in $A_9$-$A_{12}$ can be simultaneously N; $R_9$-$R_{12}$ herein; $R_{13}$ and $R_{14}$ herein; or $R_{13}$ and $R_{14}$ fused forming a ring having 5 to 7 atoms by joining $R_{13}$ being C(1-6)alkyl or C(2-6)alkenyl. The RORγ compounds can treat RORγ mediated diseases.

15 Claims, No Drawings

(51) Int. Cl.
*C07C 317/50* (2006.01)
*C07D 207/06* (2006.01)
*C07D 209/08* (2006.01)
*C07D 211/16* (2006.01)
*C07D 211/26* (2006.01)
*C07D 211/60* (2006.01)
*C07D 213/75* (2006.01)
*C07D 213/82* (2006.01)
*C07D 215/08* (2006.01)
*C07D 217/02* (2006.01)
*C07D 223/16* (2006.01)
*C07D 231/40* (2006.01)
*C07D 241/04* (2006.01)
*C07D 261/08* (2006.01)
*C07D 277/46* (2006.01)
*C07D 285/135* (2006.01)
*C07D 295/13* (2006.01)
*C07D 295/192* (2006.01)
*C07D 307/52* (2006.01)
*C07D 333/36* (2006.01)
*C07D 417/04* (2006.01)
*C07D 495/04* (2006.01)

(56) References Cited

OTHER PUBLICATIONS

Jul. 25, 2016 Written Opinion issued in International Patent Application No. PCT/EP2016/062688.

ROR GAMMA (RORγ) MODULATORS

The retinoic-acid-receptor-related orphan receptor γt (RORγt) acts as a master regulator of the development of $T_H17$ cells, but also as a critical component in non-$T_H17$ IL-17 producing cells, such as for example γδ T-cells. The ROR gene family is part of the nuclear hormone receptor superfamily, and consists of three members (RORα, RORβ, and RORγ). Each gene is expressed in different isoforms, differing foremost in their N-terminal sequence. Two isoforms of RORγ have been identified: RORγ1 and RORγ2 (also known as RORγt). The term RORγ is used here to describe both RORγ1 and/or RORγ2.

The present invention relates to modulators of RORγ, to pharmaceutical compositions comprising the same and to the use of said compounds for the treatment of RORγ-mediated diseases or conditions, in particular autoimmune diseases and inflammatory diseases.

The present invention provides novel RORγ modulator compounds according to Formula I

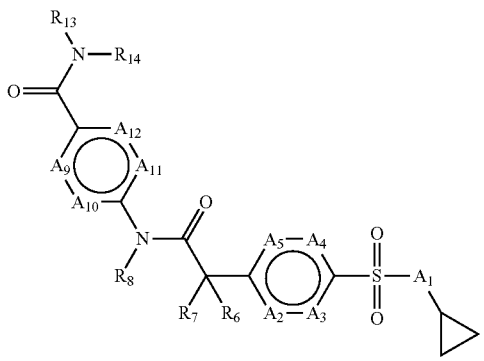

(Formula I)

or a pharmaceutically acceptable salt thereof wherein:

$A_1$ is $NR_1$ or $CR_1$, with $R_1$ being H or methyl, with methyl, if present, optionally being substituted with one or more F;

the cyclopropyl moiety can be optionally substituted with one or more methyl and one or more F;

$A_2$-$A_5$ are N or $CR_2$-$CR_5$, respectively, with the proviso that no more than two of the four positions A in $A_2$-$A_5$ can be simultaneously N;

$R_2$-$R_5$ are independently H, halogen, amino, C(1-3)alkoxy, (di)C(1-3)alkylamino or C(1-6)alkyl;

$R_6$ and $R_7$ are independently H, F, methyl, ethyl, hydroxyl or methoxy or $R_6$ and $R_7$ together is carbonyl, all alkyl groups, if present, optionally being substituted with one or more F;

$R_8$ is H or C(1-6)alkyl;

$A_9$-$A_{12}$ are N or $CR_9$-$CR_{12}$, respectively, with the proviso that no more than two of the four positions A in $A_9$-$A_{12}$ can be simultaneously N;

$R_9$-$R_{12}$ are independently H, halogen, amino, C(1-3)alkoxy, (di)C(1-3)alkylamino or C(1-6)alkyl;

$R_{13}$ is H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, amino, hydroxyl, cyano, C(1-3)alkoxy, C(1-3)alkoxycarbonyl, (di)C(1-3)alkylamino or C(1-3)alkyl; and $R_{14}$ is H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, amino, hydroxyl, cyano, C(1-3)alkoxy, C(1-3)alkoxycarbonyl, (di)C(1-3)alkylamino or C(1-3)alkyl;

or $R_{13}$ and $R_{14}$ are fused and form a ring having 5 to 7 atoms by joining $R_{13}$ being C(1-6)alkyl or C(2-6)alkenyl with an independent substituent within the definition of $R_{14}$, all groups optionally substituted with one or more halogen, amino, hydroxy, cyano, C(1-3)alkoxy, C(1-3)alkoxycarbonyl, (di)C(1-3)alkylamino or C(1-3)alkyl.

The term C(1-6)alkyl as used herein means a branched or unbranched alkyl group having 1-6 carbon atoms, for example methyl, ethyl, propyl, isopropyl, butyl, tert-butyl, n-pentyl and n-hexyl. All carbon atoms may optionally be substituted with one or more halogen.

The term C(1-4)alkyl as used herein means an alkyl group having 1-4 carbon atoms, i.e. methyl, ethyl, propyl, isopropyl, butyl, isobutyl, sec-butyl or tert-butyl. All carbon atoms may optionally be substituted with one or more halogen.

The term C(1-3)alkyl as used herein means an alkyl group having 1-3 carbon atoms, i.e. methyl, ethyl, propyl or isopropyl. All carbon atoms may optionally be substituted with one or more halogen.

The term C(1-2)alkyl as used herein means an alkyl group having 1-2 carbon atoms i.e. methyl or ethyl. All carbon atoms may optionally be substituted with one or more halogen.

The term C(2-6)alkenyl as used herein means a branched or unbranched alkenyl group having 2-6 carbon atoms, for example 4-hexenyl, but-2-enyl, 1-methylenepropyl, -propenyl (allyl) and ethenyl (vinyl). All carbon atoms may optionally be substituted with one or more halogen.

The term C(6-10)aryl as used herein means an aromatic hydrocarbon group having 6-10 carbon atoms, for example phenyl or naphthyl. The preferred aromatic hydrocarbon group is phenyl. All carbon atoms may optionally be substituted with one or more halogen.

The term C(6-10)arylC(1-4)alkyl as used herein means an C(6-10)aryl group attached to a C(1-4)alkyl group, both with the same meaning as previously defined.

The term C(6-10)arylC(1-3)alkyl as used herein means an C(6-10)aryl group attached to a C(1-3)alkyl group, both with the same meaning as previously defined.

The term C(6)aryl as used herein means an aromatic hydrocarbon group having 6 carbon atoms, i.e. phenyl. All carbon atoms may optionally be substituted with one or more halogen.

The term C(6)arylC(1-4)alkyl as used herein means an C(6)aryl group attached to a C(1-4)alkyl group, both with the same meaning as previously defined.

The term C(6)arylC(1-3)alkyl as used herein means an C(6)aryl group attached to a C(1-3)alkyl group, both with the same meaning as previously defined.

The term heteroatom as used herein refers to a nitrogen, sulfur or oxygen atom.

The term amino as used herein refers to an $NH_2$ group.

The term C(1-9)heteroaryl as used herein means an aromatic group having 1-9 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, oxazolyl, isoxazolyl, tetrazolyl, thiophenyl, thiazolyl, thiadiazolyl and quinolyl. All carbon atoms may optionally be substituted with one or more halogen or methyl.

The term C(1-9)heteroarylC(1-4)alkyl as used herein means an C(1-9)heteroaryl group attached to a C(1-4)alkyl group, both with the same meaning as previously defined.

The term C(1-9)heteroarylC(1-3)alkyl as used herein means an C(1-9)heteroaryl group attached to a C(1-3)alkyl group, both with the same meaning as previously defined.

The term C(1-5)heteroaryl as used herein means an aromatic group having 1-5 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, isoxazolyl, and tetrazolyl. All carbon atoms may optionally be substituted with one or more halogen or methyl.

The term C(1-5)heteroarylC(1-4)alkyl as used herein means an C(1-5)heteroaryl group attached to a C(1-4)alkyl group, both with the same meaning as previously defined.

The term C(1-5)heteroarylC(1-3)alkyl as used herein means an C(1-5)heteroaryl group attached to a C(1-3)alkyl group, both with the same meaning as previously defined.

The term C(3-6)cycloalkyl as used herein means a saturated cyclic hydrocarbon having 3-6 carbon atoms, i.e. cyclopropyl, cyclobutyl, cyclopentyl or cyclohexyl. All carbon atoms may optionally be substituted with one or more halogen or methyl.

The term C(3-6)cycloalkylC(1-4)alkyl as used herein means an C(3-6)cycloalkyl group attached to an C(1-4)alkyl group, both with the same meaning as previously defined. An example is cyclopropylethyl.

The term C(3-6)cycloalkylC(1-3)alkyl as used herein means an C(3-6)cycloalkyl group attached to an C(1-3)alkyl group, both with the same meaning as previously defined. An example is cyclopropylmethyl.

The term cyclopropylmethyl as used herein means a methyl group substituted with cyclopropyl. All carbon atoms are optionally substituted with one or more halogen or methyl.

The term C(2-5)heterocycloalkyl as used herein means a saturated cyclic hydrocarbon having 2-5 carbon atoms and 1-3 heteroatoms, which may be attached via a nitrogen atom if feasible, or a carbon atom. Examples include piperazinyl, pyrazolidilyl, piperidinyl, oxolanyl oxetanyl, morpholinyl, pyrrolidinyl, tetrahydropyranyl, benzoxazine. All carbon atoms may optionally be substituted with one or more halogen or methyl.

The term C(2-5)heterocycloalkylC(1-4)alkyl as used herein means an C(2-5)heterocycloalkyl group attached to an C(1-4)alkyl group, both with the same meaning as previously defined.

The term C(2-5)heterocycloalkylC(1-3)alkyl as used herein means an C(2-5)heterocycloalkyl group attached to an C(1-3)alkyl group, both with the same meaning as previously defined.

The term (di)C(1-3)alkylamino as used herein means an amino group, which is monosubstituted or disubstituted with a C(1-3)alkyl group, the latter having the same meaning as previously defined.

The term C(1-6)alkoxy means an alkoxy group having 1-6 carbon atoms, the alkyl moiety being branched or unbranched. All carbon atoms are optionally substituted with one or more F.

The term C(1-3)alkoxy means an alkoxy group having 1-3 carbon atoms, the alkyl moiety being branched or unbranched. All carbon atoms are optionally substituted with one or more F.

The term C(1-3)alkoxycarbonyl means a carbonyl group substituted with a C(1-3)alkoxy, the latter having the same meaning as previously defined.

The term halogen as used herein means Br, Cl or F.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced by a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt represents those salts which are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one embodiment the invention relates to a compound according to Formula I wherein:

$A_1$ is $NR_1$ or $CR_1$, with $R_1$ being H;

$A_2$-$A_5$ are respectively $CR_2$-$CR_5$;

or $A_3$ or $A_4$ is N, the remaining positions A being carbon;

$R_2$-$R_5$ are independently H;

$R_6$ and $R_7$ are independently H;

$R_8$ is H;

$A_9$-$A_{12}$ are respectively $CR_9$-$CR_{12}$;

or $A_{10}$ or $A_{11}$ is N, the remaining positions A being carbon;

$R_9$-$R_{12}$ are independently H, halogen, C(1-3)alkoxy or C(1-6)alkyl;

$R_{13}$ is H, C(1-6)alkyl, C(2-6)alkenyl, C(3-6)cycloalkyl, C(6-10)aryl, C(6-10)arylC(1-4)alkyl, or C(1-9)heteroaryl, all groups optionally substituted with one or more hydroxyl or C(1-3)alkyl; and $R_{14}$ is C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, hydroxyl, cyano, C(1-3) alkoxy, C(1-3)alkoxycarbonyl or C(1-3)alkyl;

or $R_{13}$ and $R_{14}$ are fused and form a ring having 5 to 7 atoms by joining $R_{13}$ being C(1-6)alkyl with an independent substituent within the definition of $R_{14}$, all groups optionally substituted with one or more hydroxy, C(1-3)alkoxy, (di)C(1-3)alkylamino. or C(1-3)alkyl.

In one embodiment the invention also relates to a compound according to Formula I wherein:

$A_1$ is $NR_1$ or $CR_1$, with $R_1$ being H;
$A_2$-$A_5$ are respectively $CR_2$-$CR_5$;
or $A_3$ or $A_4$ is N, the remaining positions A being carbon;
$R_2$-$R_5$ are independently H;
$R_6$ and $R_7$ are independently H;
$R_8$ is H;
$A_9$-$A_{12}$ are respectively $CR_9$-$CR_{12}$;
or $A_{10}$ or $A_{11}$ is N, the remaining positions A being carbon;
$R_{13}$ is H, methyl, ethyl, propyl, butyl, isobutyl, propen-1-yl, cyclobutyl, cyclopropyl, phenyl, benzyl, or pyridinyl all groups optionally substituted with one, hydroxyl or methyl; and
$R_{14}$ is methyl, ethyl, propyl, butyl, isobutyl, tert-butyl, propen-1-yl, cyclopropyl, cyclobutyl, cyclohexyl, cyclopropylmethyl, cyclobutylmethyl, piperidinyl, oxetanyl, oxolanyl, tetrahydropyranyl, morpholinylethyl, oxolanylpropanyl, phenyl, benzyl, phenylethyl, pyridinyl, thiazolyl, thiophenyl, pyrazolyl, oxazolyl, thiadiazolyl, pyridinylmethyl, isoxazolylmethyl, furanylmethyl or thiophenylmethyl, all groups optionally substituted with one or more halogen, hydroxyl, cyano, methoxy, methoxycarbonyl, ethoxycarbonyl, or methyl;
or $R_{13}$ and $R_{14}$ are fused and form phenylpyrrolidine, piperidine, phenylpiperidine, 4,5,6,7-tetrahydrothieno[2,3-c]pyridine, (1,3-thiazolyl)pyrrolidine, (morpholinylmethyl)piperidine, 1,2,3,4-tetrahydroquinoline, 2,3-dihydro-2H-isoindole, phenylpiperazine, 2,3,4,5-tetrahydro-1H-1-benzazepine, 1,4-benzoxazine, 7-oxa-4-azaspiro[2.5]octane, all groups optionally substituted with one or more ethoxycarbonyl, or methyl.

In one embodiment the invention also relates to a compound according to Formula I wherein:

$A_1$ is $NR_1$ or $CR_1$, with $R_1$ being H;
$A_2$-$A_5$ are respectively $CR_2$-$CR_5$;
$R_2$-$R_5$ are independently H;
$R_6$ and $R_7$ are independently H;
$R_8$ is H;
$A_9$ and $A_{12}$ are respectively $CR_9$ and $CR_{12}$;
$A_{10}$ or $A_{11}$ is N, the remaining position A being $CR_{10}$ or $CR_{11}$;
$R_9$-$R_{12}$ are independently H, halogen, C(1-3)alkoxy or C(1-6)alkyl;
$R_{13}$ is C(1-6)alkyl and
$R_{14}$ is C(6-10)aryl.

In one embodiment the invention relates to a compound according to Formula I wherein:

$A_1$ is $CR_1$, with $R_1$ being H;
$A_2$ and $A_5$ are respectively $CR_2$ and $CR_5$;
$A_3$ or $A_4$ is N, the remaining position A being $CR_3$ or $CR_4$;
$R_2$-$R_5$ are independently H;
$R_6$ and $R_7$ are independently H;
$R_8$ is H;
$A_9$-$A_{12}$ are respectively $CR_9$-$CR_{12}$;
$R_9$-$R_{12}$ are independently H or halogen;
$R_{13}$ is C(1-6)alkyl, all groups optionally substituted with one or more halogen; and
$R_{14}$ is C(6-10)aryl. In one embodiment the invention also relates to a compound according to Formula I wherein $A_1$ is $CR_1$.

In another embodiment the invention relates to a compound according to Formula I wherein $A_1$ is $NR_1$.

In another embodiment the invention relates to a compound according to Formula I wherein $R_1$ is hydrogen.

In one embodiment the invention also relates to a compound according to Formula I wherein $A_1$ is $CR_1$ and $R_1$ is hydrogen.

In another embodiment the invention relates to a compound according to Formula I wherein $A_1$ is $NR_1$ and $R_1$ is hydrogen.

In another embodiment the invention relates to a compound according to Formula I wherein all of the positions A in $A_2$-$A_5$ are carbon.

In another embodiment the invention relates to a compound according to Formula I wherein all of the positions A in $A_2$-$A_5$ are carbon and all of the position R in $R_2$-$R_5$ are H.

In another embodiment the invention relates to a compound according to Formula I wherein at least one, but no more than two of the four positions A in $A_2$-$A_5$ is nitrogen.

In yet another embodiment the invention relates to a compound according to Formula I wherein one of the positions A in $A_2$-$A_5$ is nitrogen and the remaining positions A in $A_2$-$A_5$ are carbon.

In one embodiment the invention relates to a compound according to Formula I wherein $A_2$-$A_5$ are respectively $CR_2$-$CR_5$ or one of the positions $A_3$ or $A_4$ is N, the remaining positions A being carbon.

In one embodiment the invention relates to a compound according to Formula I wherein $A_3$ or $A_4$ is N, the remaining positions A being carbon and $A_9$-$A_{12}$ are respectively $CR_9$-$CR_{12}$.

In yet another embodiment the invention relates to a compound according to Formula I wherein $R_2$ is methyl and $R_3$-$R_5$ are H.

In another embodiment the invention relates to a compound according to Formula I wherein $R_2$-$R_5$ are H.

In another embodiment the invention relates to a compound according to Formula I wherein $R_6$ and $R_7$ are independently H, methyl or hydroxyl.

In another embodiment the invention relates to a compound according to Formula I wherein $R_6$ and $R_7$ is H.

The invention also relates to a compound according to Formula I wherein $R_8$ is H or C(1-2)alkyl.

The invention also relates to a compound according to Formula I wherein $R_8$ is H.

The invention also relates to a compound according to Formula I wherein all positions A of $A_9$-$A_{12}$ are carbon.

In another embodiment the invention relates to a compound according to Formula I wherein at least one, but no more than two of the four positions A in $A_9$-$A_{12}$ is nitrogen.

In yet another embodiment the invention relates to a compound according to Formula I wherein one of the positions A in $A_9$-$A_{12}$ is nitrogen and the remaining positions A in $A_9$-$A_{12}$ are carbon.

In one embodiment the invention relates to a compound according to Formula I wherein $A_9$-$A_{12}$ are respectively $CR_2$-$CR_5$ or one of the positions $A_9$-$A_{12}$ is N, the remaining positions A being carbon.

In again another embodiment the invention relates to a compound according to Formula I wherein $A_9$ or $A_{12}$ is nitrogen, the remaining positions A being carbon and $A_2$-$A_5$ are respectively $CR_2$-$CR_5$.

In again another embodiment the invention relates to a compound according to Formula I wherein $A_{10}$ or $A_{11}$ is nitrogen and the remaining position A in $A_9$-$A_{12}$ are carbon.

In yet another embodiment the invention relates to a compound according to Formula I wherein all positions A of $A_9$-$A_{12}$ are carbon or wherein position A in either $A_9$ or $A_{10}$ is nitrogen and the remaining positions A are carbon.

In another embodiment the invention relates to a compound according to Formula I wherein $R_9$-$R_{12}$ are independently H, halogen, methoxy or methyl.

In another embodiment the invention relates to a compound according to Formula I wherein $R_9$-$R_{12}$ are independently H.

In another embodiment the invention relates to a compound according to Formula I wherein $R_{13}$ and $R_{14}$ are independently H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, amino, hydroxyl, cyano, C(1-3)alkoxy, C(1-3)alkoxycarbonyl, (di)C(1-3)alkylamino or C(1-3)alkyl.

In yet another embodiment the invention relates to a compound according to Formula i wherein $R_{13}$ and $R_{14}$ are independently H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkylC(1-4)alkyl, C(6)aryl, C(6)arylC(1-4)alkyl, C(1-5)heteroaryl or C(1-5)heteroarylC(1-4)alkyl, all groups optionally substituted with one or more halogen, hydroxy, cyano, C(1-3)alkoxy, C(1-3)alkoxycarbonyl, or C(1-3)alkyl.

In yet another embodiment the invention relates to a compound according to Formula I wherein $R_{13}$ is H, methyl, ethyl, propyl, butyl, isobutyl, propen-1-yl, cyclobutyl, cyclopropyl, phenyl, benzyl, or pyridinyl all groups optionally substituted with one hydroxyl or methyl; and $R_{14}$ is methyl, ethyl, propyl, butyl, isobutyl, tert-butyl, propen-1-yl, cyclopropyl, cyclobutyl, cyclohexyl, cyclopropylmethyl, cyclobutylmethyl, piperidinyl, oxetanyl, oxolanyl, tetrahydropyranyl, morpholinylethyl, oxolanylpropanyl, phenyl, benzyl, phenylethyl, pyridinyl, thiazolyl, thiophenyl, pyrazolyl, oxazolyl, thiadiazolyl, pyridinylmethyl, isoxazolylmethyl, furanylmethyl or thiophenylmethyl, all groups optionally substituted with one or more halogen, hydroxyl, cyano, methoxy, methoxycarbonyl, ethoxycarbonyl, or methyl.

In another embodiment the invention relates to a compound according to Formula I wherein $R_{13}$ and $R_{14}$ are fused and form a ring consisting of 5 to 7 atoms by joining C(1-6)alkyl at $R_{13}$ with a substituent at $R_{14}$ selected from C(1-6)alkyl, C(2-6)alkenyl, (3-6)cycloalkyl, C(3-6)cycloalkylC(1-4)alkyl, C(2-5)heterocycloalkyl, C(2-5)heterocycloalkyl-C(1-4)alkyl, C(6)aryl, C(6)arylC(1-4)alkyl, C(1-5)heteroaryl or C(1-5)heteroarylC(1-4)alkyl, with all groups optionally substituted with one or more halogen, hydroxy, cyano, C(1-3)alkoxy, C(1-3)alkoxycarbonyl, or C(1-3)alkyl.

In again another embodiment the invention relates to a compound according to Formula I wherein $R_{13}$ and $R_{14}$ are fused and form a cyclic hydrocarbon having 5 or 6 carbon atoms by joining ethyl or propyl at $R_{13}$ with $R_{14}$ selected from C(1-6)alkyl, C(2-6)alkenyl, C(2-5)heterocycloalkyl, C(2-5)heterocycloalkylC(1-3)alkyl, C(6)aryl, C(6)arylC(1-3)alkyl, C(1-5)heteroaryl or C(1-5)heteroarylC(1-3)alkyl, with all groups optionally substituted with one or more halogen, cyano, C(1-3)alkoxy, C(1-3)alkoxycarbonyl, (di)C(1-3)alkylamino or C(1-3)alkyl. In another embodiment the invention relates to a compound according to Formula I wherein $R_{13}$ and $R_{14}$ $R_{13}$ and $R_{14}$ are fused and form phenylpyrrolidine, piperidine, phenylpiperidine, 4,5,6,7-tetrahydrothieno[2,3-c]pyridine, (1,3-thiazolyl)pyrrolidine, (morpholinylmethyl)piperidine, 1,2,3,4-tetrahydroquinoline, 2,3-dihydro-2H-isoindole, phenylpiperazine, 2,3,4,5-tetrahydro-1H-1-benzazepine, 4-benzoxazine, 7-oxa-4-azaspiro[2.5]octane, all groups optionally substituted with one or more methoxycarbonyl, ethoxycarbonyl, methylamino, or methyl.

The invention also relates to those compounds wherein all specific definitions for $A_1$ through $A_{12}$, $R_1$ through $R_{14}$, and all substituent groups in the various aspects of the inventions defined here above occur in any combination within the definition of the compound of Formula I.

In another aspect the invention relates to compounds of Formula I, which have a pIC50 of 5 or higher. In yet another aspect the invention relates to compounds according to Formula I with a pIC50 of more than 6. In yet another aspect the invention relates to compounds according to Formula I with a pIC50 of more than 7. In yet another aspect the invention relates to compounds according to Formula I with a pIC50 of more than 8.

In yet another aspect the invention resides in the compounds according to Formula I selected as described in examples 1-166.

The compounds of Formula I may form salts, which are also within the scope of this invention. Reference to a compound of Formula I herein is understood to include reference to salts thereof, unless otherwise indicated.

The compounds of Formula I may contain asymmetric or chiral centers and, therefore, exist in different stereoisomeric forms. It is intended that all stereoisomeric forms of the compounds of Formula I as well as mixtures thereof, including racemic mixtures, form part of the present invention.

Diastereomeric mixtures can be separated into their individual diastereomers on the basis of their physical chemical differences by methods well known to those skilled in the art, such as, for example, chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Enantiomers can also be separated by use of chiral HPLC column.

The skilled artisan will recognize that desirable 1050 values are dependent on the compound tested. For example, a compound with an 1050 value less than $10^{-5}$ M is generally considered as a candidate for drug selection. Preferably, this value is lower than $10^{-6}$ M. However, a compound which has a higher 1050 value, but is selective for the particular receptor, may be even a better candidate.

The compounds of the invention inhibit RORγ activity. Modulation of RORγ activity can be measured using for example biophysical (natural) ligand displacement studies, biochemical AlphaScreen or FRET assays, cellular GAL4 reporter gene assays, cellular IL-17 promotor reporter assay or functional IL-17 ELISA assays using for example mouse splenocytes or human peripheral blood mononuclear cells (PBMCs) cultured under $T_H17$ polarizing conditions.

In such assays, the interaction of a ligand with RORγ can be determined by measuring, for example, the ligand modulated interaction of cofactor-derived peptides with the RORγ ligand binding domain, or measuring the gene products of ligand modulated RORγ mediated transcription using, for example, luciferase reporter assays or IL-17 ELISA assays.

The present invention also relates to a pharmaceutical composition comprising compounds or pharmaceutically acceptable salts thereof having the general Formula I in admixture with pharmaceutically acceptable excipients and optionally other therapeutically active agents. The excipients must be "acceptable" in the sense of being compatible with the other ingredients of the composition and not deleterious to the recipients thereof.

The present invention also relates to a pharmaceutical composition comprising at least one additional therapeutically active agent.

The invention further includes a compound of Formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive, which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as herein before described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration, which are more dependent upon absorption. However, a dosage for humans preferably contains 0.0001-100 mg per kg body weight. The desired dose may be presented as one dose or as multiple sub-doses administered at appropriate intervals throughout the day.

The compounds according to the invention or a pharmaceutically acceptable salt thereof can be used as medicament in therapy.

A further aspect of the invention resides in the use of compounds according to the invention or a pharmaceutically acceptable salt thereof for the treatment of RORγ-mediated diseases or RORγ mediated conditions.

Another aspect of the invention resides in the use of compounds having the general Formula I or a pharmaceutically acceptable salt thereof for the treatment of autoimmune diseases, in particular those diseases in which $T_H17$ cells and non-$T_H17$ cells, which express $T_H17$ hallmark cytokines play a prominent role. These include, but are not limited to, the treatment of rheumatoid arthritis, psoriasis, inflammatory bowel disease, Crohn's disease and multiple sclerosis.

In another aspect, compounds having the general Formula I or a pharmaceutically acceptable salt thereof can be used for treatment of inflammatory diseases in which $T_H17$ cells and/or non-$T_H17$ cells, which express $T_H17$ hallmark cytokines play a prominent role such as, but not limited to respiratory diseases, osteoarthritis and asthma. Also, compounds or a pharmaceutically acceptable salt thereof having the general Formula I can be used for treatment of infectious diseases in which $T_H17$ cells and/or non-$T_H17$ cells, which express $T_H17$ hallmark cytokines play a prominent role such as, but not limited to mucosal leishmaniasis.

Compounds having the general Formula I or a pharmaceutically acceptable salt thereof can also be used for treatment of other diseases in which $T_H17$ cells and/or non-$T_H17$ cells, which express $T_H17$ hallmark cytokines play a prominent role such as, but not limited to Kawaski disease and Hashimoto's thyroiditis.

In yet another aspect the invention resides in the use of compounds having the general Formula I for the treatment of multiple sclerosis, inflammatory bowel disease, Crohn's disease, psoriasis, rheumatoid arthritis, asthma, osteoarthritis, Kawaski disease, Hashimoto's thyroiditis, cancer and mucosal leishmaniasis.

In another aspect, the compounds according to the invention can be used in therapies to treat or prevent multiple sclerosis, inflammatory bowel disease, Crohn's disease, psoriasis and rheumatoid arthritis, asthma, osteoarthritis, Kawaski disease, Hashimoto's thyroiditis, cancer and mucosal leishmaniasis.

In another aspect the compounds according to the invention can be used to treat or prevent psoriasis.

In yet another aspect the compounds according to the invention can be used to treat inflammatory bowel disease.

The invention is illustrated by the following examples.

EXEMPLIFICATION

As depicted in the Examples below, in certain exemplary embodiments, compounds are prepared according to the following general procedures. It will be appreciated that, although the general methods depict the synthesis of certain compounds of the invention, the following general methods, and other methods known to one skilled in the art, can be applied to all compounds and subclasses and species of each of these compounds, as described herein.

General Methods of Preparation

The compounds described herein, including compounds of general Formula I, can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those skilled in the art, but are not mentioned in greater detail. For example, where specific acids, bases, reagents, coupling agents, solvents, etc. are mentioned, it is understood that other suitable acids, bases, reagents, coupling agents, solvents etc. may be used and are included within the scope of the present invention. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxyl, thiol and carboxylic acid groups that may interfere with the desired reaction, it may be advantageous to employ protected forms of the intermediate. Methods for the selection, introduction and subsequent removal of protecting groups are well known to those skilled in the art. The compounds obtained by using the general reaction sequences may be of insufficient purity. The compounds can be purified by using any of the methods of purification of organic compounds, for example, crystallization or silica gel or alumina column chromatography, using different solvents in suitable ratios.

All possible stereoisomers are envisioned within the scope of the invention. In the discussion below variables have the meaning indicated above unless otherwise indicated.

The abbreviations used in these experimental details are listed below and additional ones should be considered known to a person skilled in the art of synthetic chemistry.

Abbreviations used herein are as follow: r.t.: room temperature; HATU: 2-(7-Aza-1H-benzotriazole-1-yl)-1,1,3,3-tetramethyluronium hexafluorophosphate; DMF: Dimethyl formamide; DiPEA: Diisopropylethylamine; DMAP: 4-(dimethylamino)pyridine; DCC: N,N'-Dicyclohexylcarbodiimide; mCPBA: 3-chloroperoxybenzoic acid; TFA: Trifluoroacetic acid; THF: Tetrahydrofuran; DMSO: Dimethylsulfoxide; PyBOP: (Benzotriazol-1-yloxy)tripyrrolidinophosphonium hexafluorophosphate; EtOH: Ethanol; TLC: Thin Layer Chromatography; EDCl: 1-Ethyl-3-(3-dimethylaminopropyl)carbodiimide; AIBN: Azobisisobutyronitrile; NBS: N-bromosuccinimide; TBAF: tetra-n-butylammonium fluoride; TMSCN: trimethylsilyl cyanide.

Chemical names are preferred IUPAC names, generated using MarvinSketch version 6.3.0.

If a chemical compound is referred to using both a chemical structure and a chemical name, and an ambiguity exists between the structure and the name, the structure predominates.

General Procedures

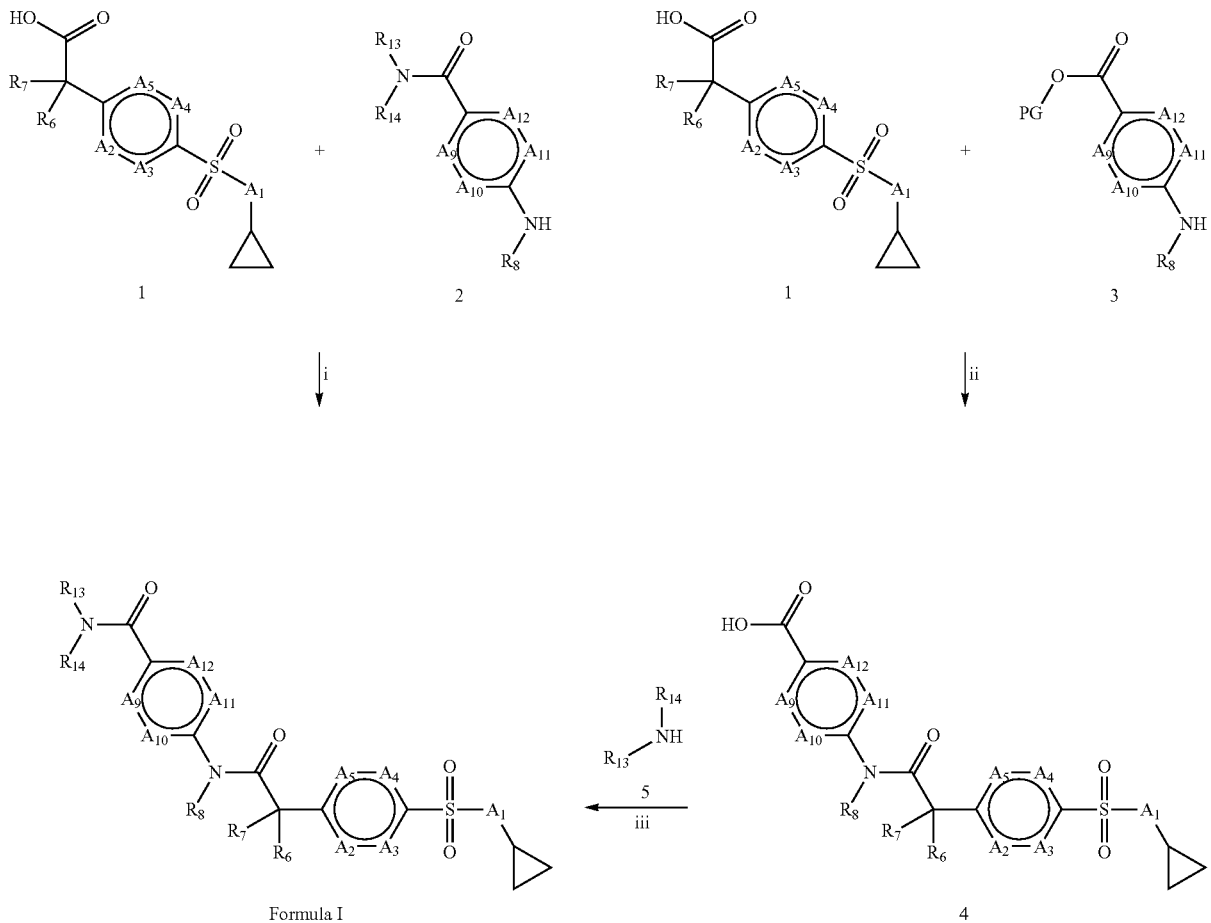

Scheme 1:

Formula I

As depicted in scheme 1, the derivatives of the invention having Formula I can be prepared by methods known in the art of organic chemistry. Compounds of the invention can for example be obtained by an amide coupling reaction between a (hetero)aryl acetic acid derivative 1, wherein $A_1$, $A_2$, $A_3$, $A_4$, $A_5$, $R_6$, and $R_7$ have the meaning as previously described, and an amine derivative 2, wherein $A_9$, $A_{10}$, $A_{11}$, $A_{12}$, $R_8$, $R_{13}$ and $R_{14}$ have the meaning as previously described, which can easily be prepared by someone skilled in the art of organic chemistry, using a coupling reagent such as EDCl, HATU, DCC, or PyBOP or the like, in the presence of a suitable base such as DiPEA or catalyst such as DMAP.

In an alternative way, a (hetero)aryl acetic acid derivative 1 can be converted into an acid chloride, using for example $SOCl_2$ or oxalyl chloride, which then can be coupled, in the presence of a suitable base such as $Et_3N$ or the like, with an amine derivative 2, obtaining derivatives of Formula I.

Alternatively, a (hetero)aryl acetic acid derivative 1 can be condensed with a suitable acid protected (hetero)aryl amino derivative 3, wherein $A_9$, $A_{10}$, $A_{11}$, $A_{12}$, and $R_8$ have the meaning as previously described, using methods as described above. After removal of the protecting group, the obtained carboxylic acid derivative 4 can be condensed with a suitable amine 5, wherein $R_{13}$ and $R_{14}$ have the meaning as previously described, using methods as described before, giving derivatives of Formula I.

Scheme 2:

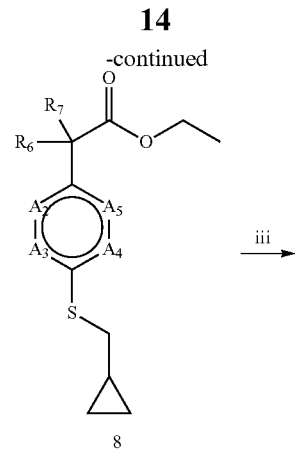

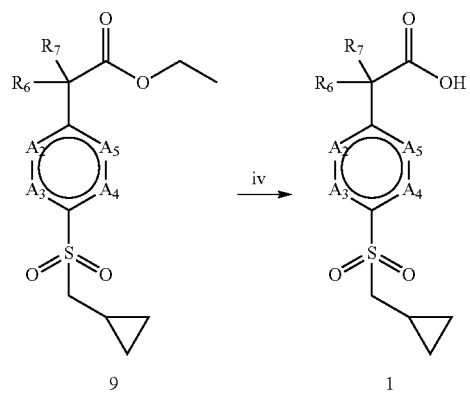

Conditions: i) $H_2SO_4$, EtOH, 60° C.;
ii) (bromomethyl) cyclopropane, $K_2CO_3$, $CH_3CN$, r.t.;
iii) mCPBA, $CH_2Cl_2$, r.t.;
iv) 2N NaOH, EtOH, r.t..

Scheme 2 illustrates a general method for preparing 2-(4-cyclopropylmethanesulfonylphenyl)acetic acid derivatives of building block 1 wherein $A_1$ is C and $A_2$, $A_3$, $A_4$, $A_5$, $R_6$ and $R_7$ have the meaning as previously described.

Esterification of 4-mercaptophenylacetic acid derivatives 6 under acidic conditions, using for example $H_2SO_4$ in ethanol, provides 4-mercaptophenylacetic acid ethylester derivatives 7. Alkylation of the sulfur group using (bromomethyl)cyclopropane in the presence of a base, such as $K_2CO_3$, gives the corresponding 2-(4-cyclopropylmethanesulfanylphenyl)acetate derivatives 8. Oxidation, using e.g. mCPBA, gives 2-(4-cyclopropylmethanesulfonylphenyl)acetate derivatives 9 which after saponification of the ester moiety under basic conditions, e.g. NaOH in ethanol, gives the corresponding 2-(4-cyclopropylmethanesulfonylphenyl) acetic acid derivatives of building block 1.

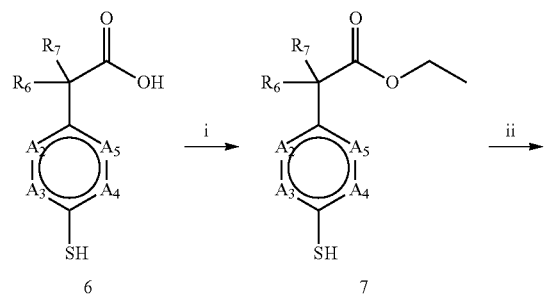

Scheme 3:

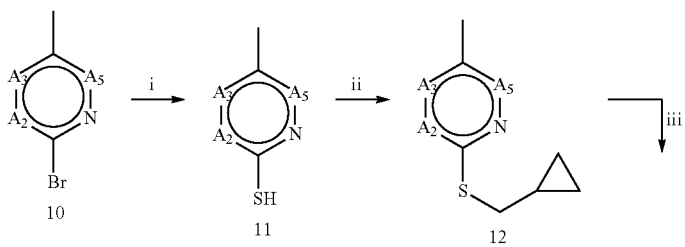

-continued

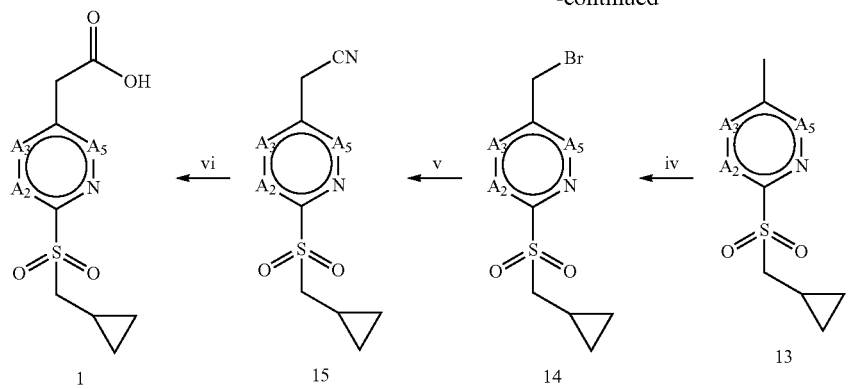

Conditions (A₁ = C, A₄ = N and R₆ and R₇ are H): i) Thiourea, HCl (aq), reflux; ii) (bromomethyl)cyclopropane, K₂CO₃, CH₃CN, r.t.; iii) mCPBA, CH₂Cl₂, 0° C. -> RT; iv) NBS, AIBN, CH₃CN, 60° C.; v) TMSCN, TBAF, CH₃CN, reflux; vi) NaOH, EtOH, reflux.

Scheme 3 shows a general method for the preparation of 2-(6-alkylsulfonylpyridin-3-yl)acetic acid derivatives of building block 1 wherein $A_1$ is C, $A_4$ is N, $R_6$ and $R_7$ are H and $A_2$, $A_3$ and $A_5$ have the meaning as previously described.

Reaction of 2-bromo-5-methylpyridine derivatives 10 with thiourea under acidic conditions gives 5-methylpyridine-2-thiol derivatives 11 which can be alkylated in the presence of a suitable base such as potassium carbonate to give the corresponding 2-[(cyclopropylmethyl)sulfanyl]-5-methylpyridine derivatives 12. Oxidation using mCPBA for example to the corresponding sulfone derivatives 13, which upon radical bromination with NBS in presence of a radical initiator such as AIBN provides 5-(bromomethyl)-2-[(cyclopropylmethyl)sulfanyl]pyridine derivatives 14. These bromide derivatives can be converted to the corresponding nitrile derivatives 15 by treating them with a cyanide source such as TMSCN or potassium cyanide or the like. If TMSCN is used, it is required to add a fluoride source such as TBAF or the like to generate the cyanide nucleophile in situ. Hydrolysis of the nitrile derivatives 15 can provide the corresponding carboxylic acid derivatives of building block 1 wherein $A_1$ is C and $A_4$ is N.

Some of the building blocks 1 are commercially available, known or prepared according to methods known to those skilled in the art.

Scheme 4:

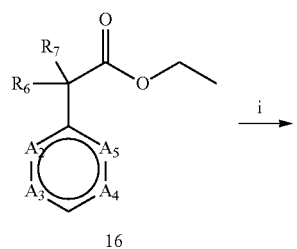

16

-continued

[structures 17, 18, 1]

Conditions: i) Chlorosulfonic acid, CH₂Cl₂, 0° C. to r.t.;
ii) Cyclopropylamine, Et₃N, CH₂Cl₂, r.t.;
iii) 2N NaOH, EtOH, r.t..

Scheme 4 illustrates a general method for preparing 2-[4-(cyclopropylsulfamoyl)phenyl]acetic acid derivatives of building block 1 wherein $A_1$ is N and $A_2$, $A_3$, $A_4$, $A_5$, $R_6$ and $R_7$ have the meaning as previously described.

Reaction of ethyl 2-phenylacetate derivatives 16 with chlorosulfonic acid provides ethyl 2-[4-(chlorosulfonyl)phenyl]acetate derivatives 17 which after nucleofilic substitution with cyclopropyl amine gives ethyl 2-[4-(cyclopropylsulfamoyl) phenyl]acetate derivatives 18. Saponification of the ester moiety under basic conditions, e.g. NaOH in ethanol, gives the corresponding 2-[4-(cyclopropylsulfamoyl)phenyl]acetic acid derivatives of building block 1.

Scheme 5:

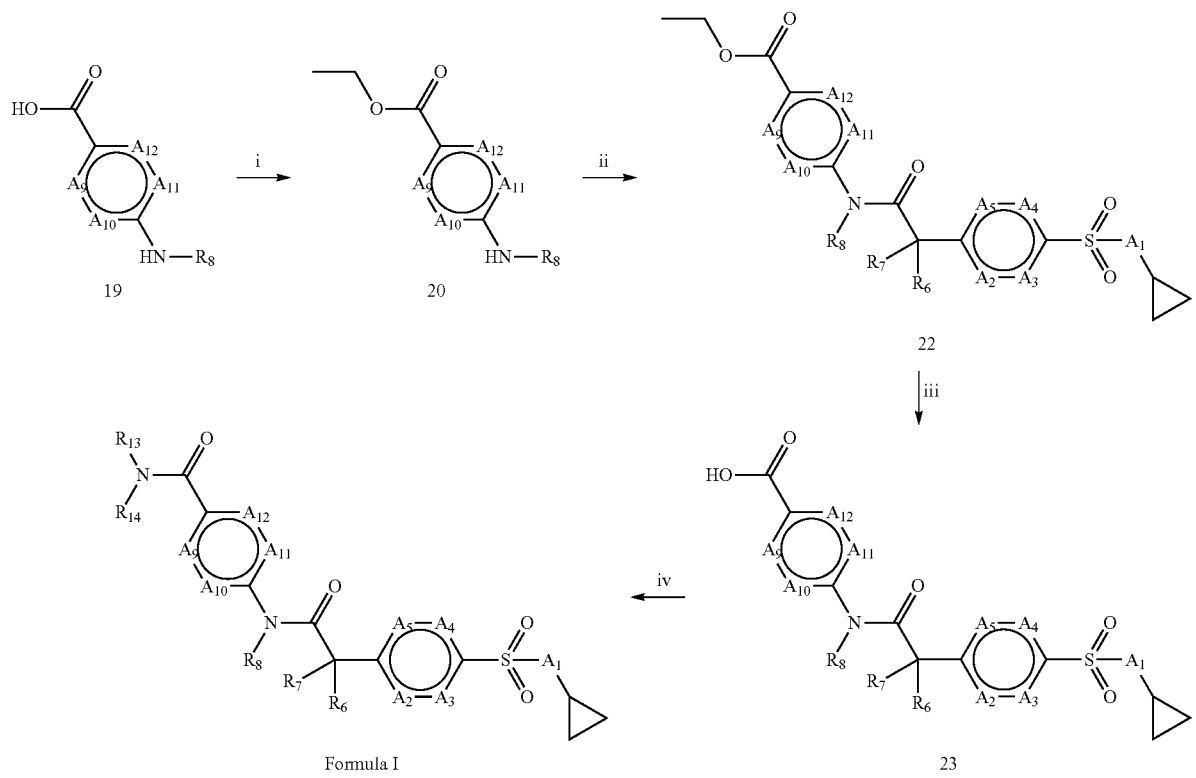

Conditions: i) EtOH, HCl$_{(conc.)}$, r.t.;
ii) Building block 1, EDCl, DMAP, CH$_2$Cl$_2$, 60° C.;
iii) 2N NaOH, EtOH, reflux;
iv) A suitable amine, EDCl, DMAP, CH$_2$Cl$_2$, 60° C.

Scheme 5 demonstrates a general method for the preparation of derivatives of Formula I wherein $A_1$, $A_2$, $A_3$, $A_4$, $A_5$, $R_6$, $R_7$, $R_8$, $A_9$, $A_{10}$, $A_{11}$, $A_{12}$, $R_{13}$ and $R_{14}$ have the meaning as previously described.

Reaction of carboxylic acid derivatives 19 with a suitable alcohol, under acidic conditions, gives the corresponding ester derivatives 20, which can be condensed with building block 1, in the presence of for example EDCl and DMAP, giving amide derivatives 22. After saponification of the ester moiety under basic conditions, by using for example NaOH in ethanol, the obtained derivatives 23 can be condensed with a suitable amine, in the presence of for example EDCl and DMAP, giving derivatives of Formula I.

Scheme 6:

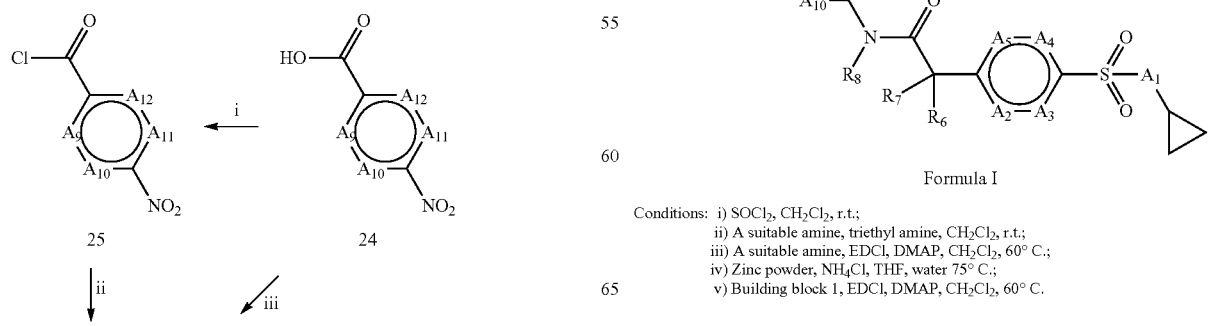

Conditions: i) SOCl$_2$, CH$_2$Cl$_2$, r.t.;
ii) A suitable amine, triethyl amine, CH$_2$Cl$_2$, r.t.;
iii) A suitable amine, EDCl, DMAP, CH$_2$Cl$_2$, 60° C.;
iv) Zinc powder, NH$_4$Cl, THF, water 75° C.;
v) Building block 1, EDCl, DMAP, CH$_2$Cl$_2$, 60° C.

Scheme 6 demonstrates an alternative route for the preparation of derivatives of Formula I wherein $A_1$, $A_2$, $A_3$, $A_4$, $A_5$, $R_6$, $R_7$, $R_8$, $A_9$, $A_{10}$, $A_{11}$, $A_{12}$, $R_{13}$ and $R_{14}$ have the meaning as previously described.

4-Nitrobenzoic acid derivatives 24 can be condensed with suitable amines, in the presence of for example EDCl and DMAP, giving 4-nitrobenzamide derivatives 26. Alternatively, 4-nitrobenzoic acid derivatives can easily be converted into the corresponding 4-nitrobenzoyl chloride derivatives 25 by using for example $SOCl_2$ or oxalyl chloride, which then can be coupled with suitable amines in the presence of a base such as $Et_3N$ or the like.

The nitro group of derivatives 26 can be reduced, by using for example tin chloride, iron in the presence of acetic acid or zinc in the presence of ammonium chloride or ammonium formate, giving the 4-aminobenzamide derivatives 27, which can be condensed with (hetero)aryl acetic acid derivatives 1, in the presence of for example EDCl and DMAP, giving Formula I derivatives wherein $R_8$ is hydrogen.

If $R_{13}$ is a C(1-6)alkyl substituted with one or more hydroxyl, the alcohol contained in the amine $R_{13}R_{14}NH$ can be protected as a silyl ether prior to condensation with the 4-nitrobenzoic acid derivatives 24 or 4-nitrobenzoyl chloride derivatives 25 as described above. After the subsequent nitro reduction and condensation with (hetero)aryl acetic acid derivative 1, derivatives of Formula I can be obtained by silyl ether deprotection with tetrabutylammonium fluoride.

EXAMPLES

All building blocks used are commercially available, known or prepared according to methods known to those skilled in the art.

Examples 1-166

1: 4-[2-(4-cyclopropylmethanesulfonylphenyl)acetamido]-N-propylbenzamide

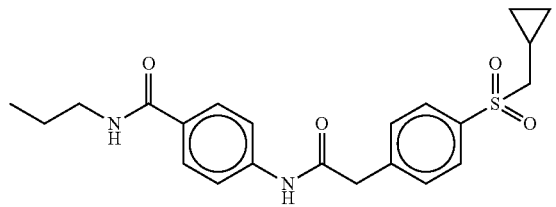

i) To a suspension of 4-aminobenzoic acid (20 g) in methanol (150 mL) was added at room temperature concentrated HCl (25 mL). The reaction mixture was stirred overnight at room temperature. The reaction was quenched by addition of a saturated aqueous $NaHCO_3$ solution. The organic solvent was removed under reduced pressure and the aqueous layer was extracted several times with ethyl acetate. The combined organic layers were washed with water then brine, dried over $MgSO_4$ and concentrated under reduced pressure giving methyl 4-aminobenzoate (22.1 g) as an off-white solid. The product was used in the next step without further purification.

ii) To a solution of the product obtained in the previous step (710 mg), 2-(4-cyclopropylmethanesulfonylphenyl) acetic acid (1.0 g) and DMAP (100 mg) in $CH_2Cl_2$ (2 mL) was added dropwise at 0° C. a solution of EDCl (900 mg) in $CH_2Cl_2$. The reaction mixture was stirred overnight at room temperature. The organic layer was washed with a saturated aqueous $NaHCO_3$ solution, water then brine, dried over $MgSO_4$ and concentrated under reduced pressure. The residue was purified on $SiO_2$, using 1% to 10% ethyl acetate in heptane as the eluent, giving methyl 4-[2-(4-cyclopropylmethanesulfonylphenyl)acetamido]benzoate (1.3 g) as a white solid.

iii) A suspension of the product obtained in the previous step (1.3 g) and a 2N aqueous NaOH solution (6 mL) in ethanol (20 mL) was stirred overnight at room temperature. Ethanol was removed under reduced pressure and water was added. The solution was washed with $CH_2Cl_2$ and the aqueous phase was acidified by adding a 2N aqueous HCl solution until pH=1. The product was extracted into ethyl acetate and the ethyl acetate layer was washed with water then brine, dried over $MgSO_4$ and concentrated under reduced pressure giving 4-[2-(4-cyclopropylmethanesulfonylphenyl)acetamido]benzoic acid (840 mg). The product was used without further purification.

iv) A solution of the product obtained in the previous step (40 mg), n-propylamine (12 uL), EDCl (25 mg) and DMAP (14 mg) in $CH_2Cl_2$ (2 mL) was stirred overnight at room temperature. The organic layer was washed with water, a saturated aqueous $NaHCO_3$ solution, brine, dried over $MgSO_4$ and concentrated under reduced pressure. The residue was purified on reverse phase HPLC, giving the title compound 4-[2-(4-cyclopropylmethanesulfonylphenyl)acetamido]-N-propylbenzamide (23 mg) as a white solid. MS(ES$^+$) m/z 415.2 (M+H)$^+$.

Following a procedure analogous to that described for Example 1, using appropriate starting materials, the following compounds have been prepared.

2: 4-[2-(4-cyclopropylmethanesulfonylphenyl)acetamido]-N-ethylbenzamide

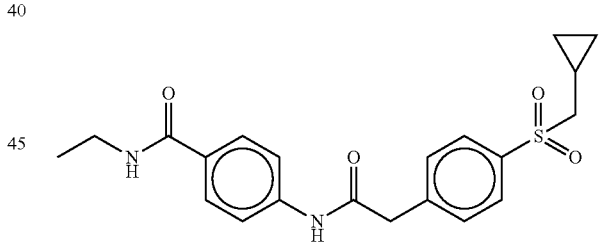

MS(ES$^+$) m/z 401.1 (M+H)$^+$.

3: 4-[2-(4-cyclopropylmethanesulfonylphenyl)acetamido]-N-methyl-N-phenylbenzamide

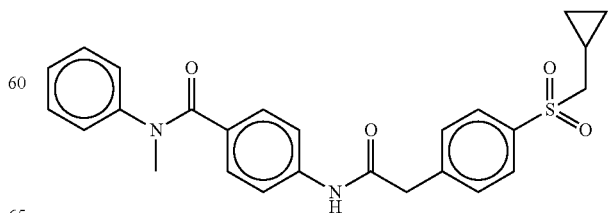

MS(ES$^+$) m/z 463.2 (M+H)$^+$.

4: 4-[2-(4-cyclopropylmethanesulfonylphenyl)acetamido]-N,N-dimethylbenzamide

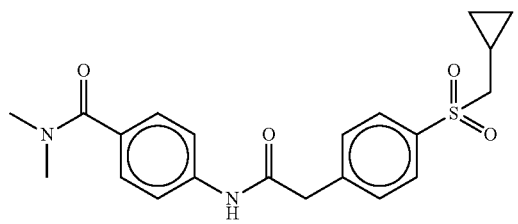

MS(ES$^+$) m/z 401.1 (M+H)$^+$.

5: N-benzyl-4-[2-(4-cyclopropylmethanesulfonylphenyl)acetamido]-N-methylbenzamide

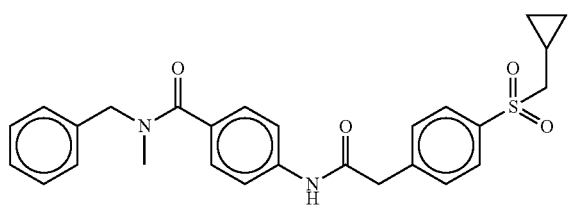

MS(ES$^+$) m/z 477.2 (M+H)$^+$.

6: 4-[2-(4-cyclopropylmethanesulfonylphenyl)acetamido]-N-(2-phenylpropan-2-yl)benzamide

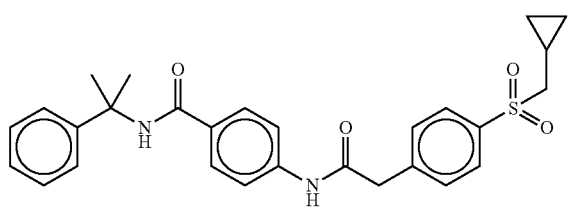

MS(ES$^+$) m/z 491.2 (M+H)$^+$.

7: 4-[2-(4-cyclopropylmethanesulfonylphenyl)acetamido]-N-methyl-N-propylbenzamide

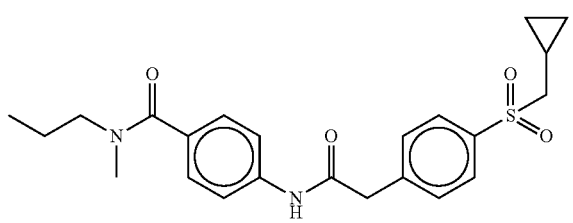

MS(ES$^+$) m/z 428.2 (M+H)$^+$.

8: 4-[2-(4-cyclopropylmethanesulfonylphenyl)acetamido]-N-methyl-N-(2-methylpropyl)benzamide

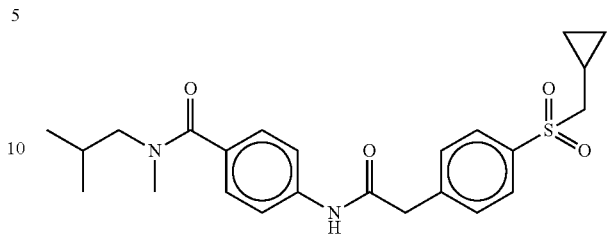

MS(ES$^+$) m/z 443.2 (M+H)$^+$.

9: 4-[2-(4-cyclopropylmethanesulfonylphenyl)acetamido]-N-(cyclopropylmethyl)-N-propylbenzamide

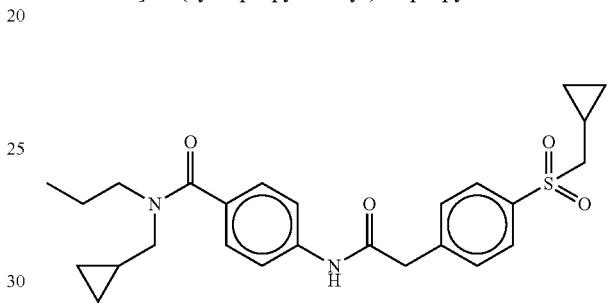

MS(ES$^+$) m/z 469.2 (M+H)$^+$.

10: 4-[2-(4-cyclopropylmethanesulfonylphenyl)acetamido]-N-methyl-N-(2-phenylethyl)benzamide

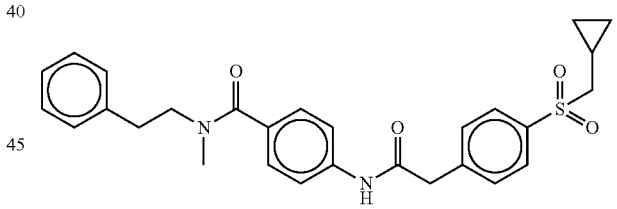

MS(ES$^+$) m/z 491.2 (M+H)$^+$.

11: N-tert-butyl-4-[2-(4-cyclopropylmethanesulfonylphenyl)acetamido]benzamide

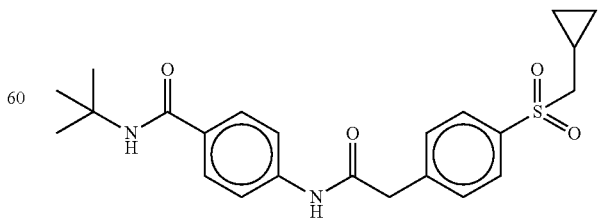

MS(ES$^+$) m/z 429.2 (M+H)$^+$.

12: N,N-dibenzyl-4-[2-(4-cyclopropylmethanesulfo-nylphenyl)acetamido]benzamide

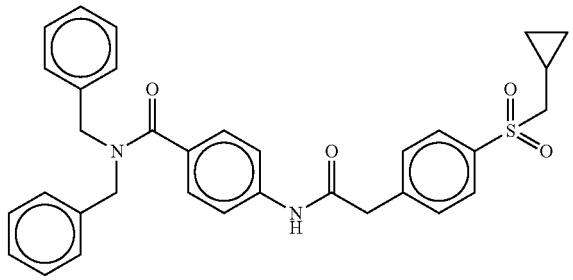

MS(ES$^+$) m/z 553.2 (M+H)$^+$.

13: N-benzyl-4-[2-(4-cyclopropylmethanesulfonyl-phenyl)acetamido]benzamide

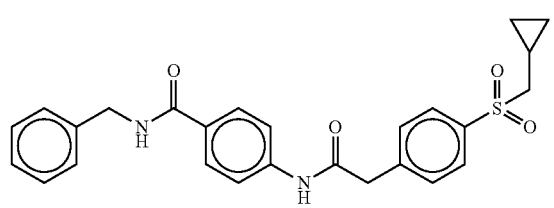

MS(ES$^+$) m/z 463.2 (M+H)$^+$.

14: 4-[2-(4-cyclopropylmethanesulfonylphenyl)acet-amido]-N-(1-phenylethyl)benzamide

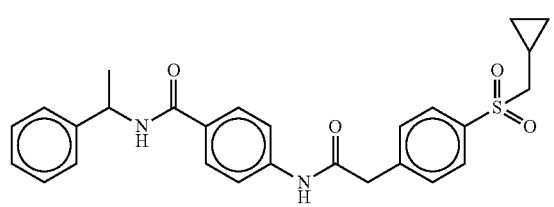

MS(ES$^+$) m/z 477.2 (M+H)$^+$.

15: 4-[2-(4-cyclopropylmethanesulfonylphenyl)acet-amido]-N,N-bis(2-methylpropyl)benzamide

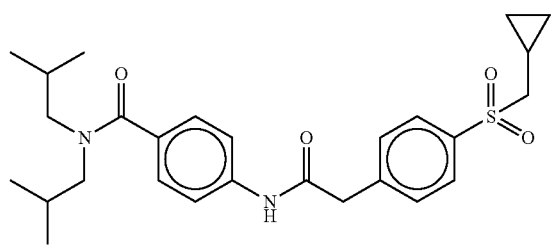

MS(ES$^+$) m/z 485.2 (M+H)$^+$.

16: 4-[2-(4-cyclopropylmethanesulfonylphenyl)acet-amido]-N-ethyl-N-phenylbenzamide

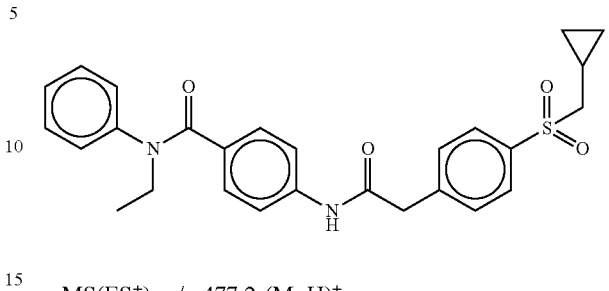

MS(ES$^+$) m/z 477.2 (M+H)$^+$.

17: 4-[2-(4-cyclopropylmethanesulfonylphenyl)acet-amido]-N-methyl-N-(pyridin-2-yl)benzamide

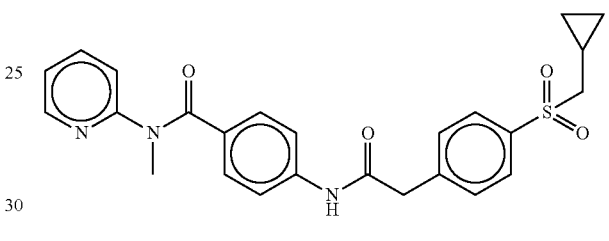

MS(ES$^+$) m/z 464.2 (M+H)$^+$.

18: 4-[2-(4-cyclopropylmethanesulfonylphenyl)acet-amido]-N-methyl-N-[(1S)-1-phenylethyl]benzamide

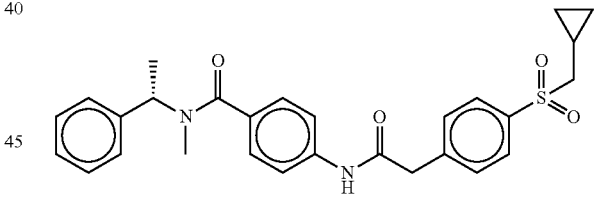

MS(ES$^+$) m/z 491.2 (M+H)$^+$.

19: 4-[2-(4-cyclopropylmethanesulfonylphenyl)acet-amido]-N-phenyl-N-propylbenzamide

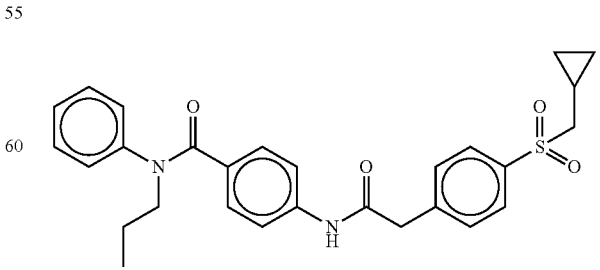

MS(ES$^+$) m/z 491.2 (M+H)$^+$.

20: 4-[2-(4-cyclopropylmethanesulfonylphenyl)acet-
amido]-N-propyl-N-(pyridin-3-yl)benzamide

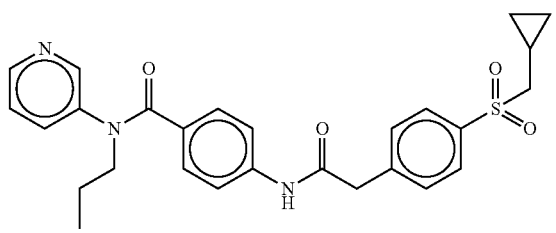

MS(ES⁺) m/z 492.2 (M+H)⁺.

21: N-benzyl-4-[2-(4-cyclopropylmethanesulfonyl-
phenyl)acetamido]-N-propylbenzamide

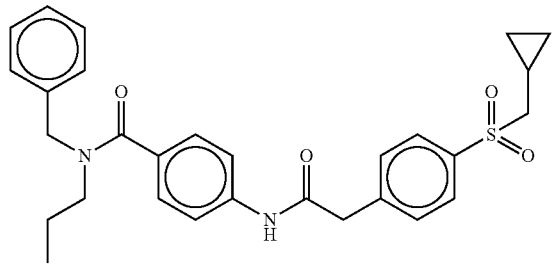

MS(ES⁺) m/z 505.2 (M+H)⁺.

22: 4-{2-[4-(cyclopropylsulfamoyl)phenyl]acet-
amido}-N-phenyl-N-propylbenzamide

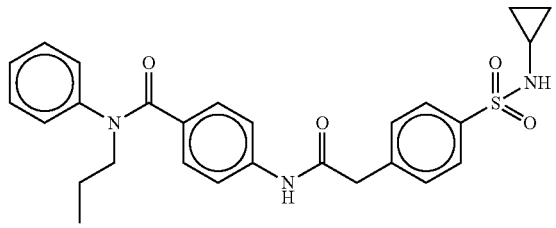

MS(ES⁺) m/z 492.2 (M+H)⁺.

23: N-benzyl-4-{2-[4-(cyclopropylsulfamoyl)phe-
nyl]acetamido}-N-propylbenzamide

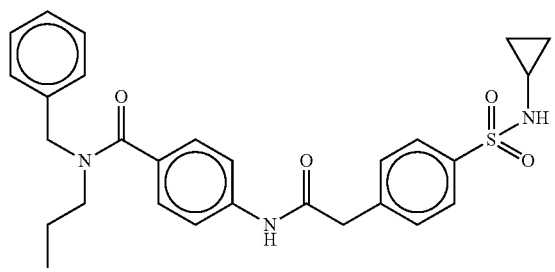

MS(ES⁺) m/z 506.2 (M+H)⁺.

24: N,N-dibenzyl-4-{2-[4-(cyclopropylsulfamoyl)
phenyl]acetamido}benzamide

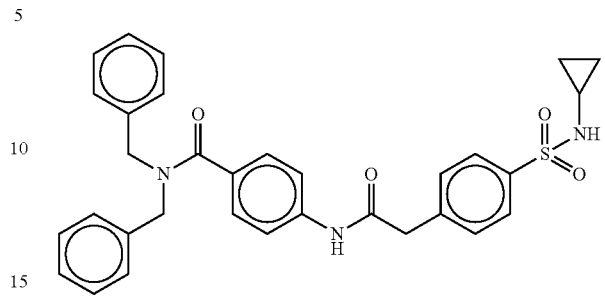

MS(ES⁺) m/z 554.2 (M+H)⁺.

25: ethyl 1-{4-[2-(4-cyclopropylmethanesulfonyl-
phenyl)acetamido]benzoyl}piperidine-3-carboxylate

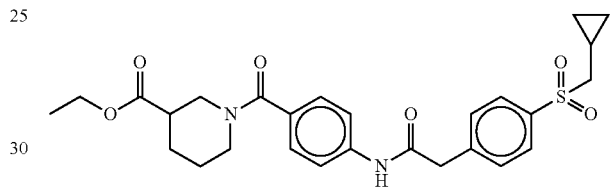

MS(ES⁺) m/z 513.2 (M+H)⁺.

26: N-tert-butyl-4-[2-(4-cyclopropylmethanesulfo-
nylphenyl)acetamido]-N-methylbenzamide

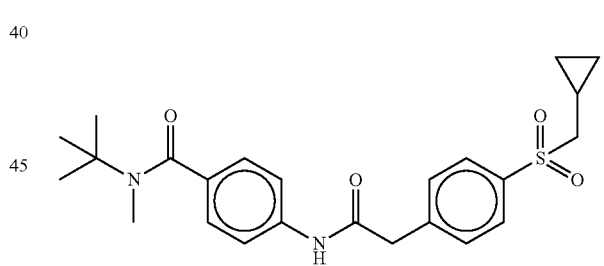

MS(ES⁺) m/z 443.2 (M+H)⁺.

27: N,N-dicyclobutyl-4-[2-(4-cyclopropylmethanesulfo-
nylphenyl)acetamido]benzamide.

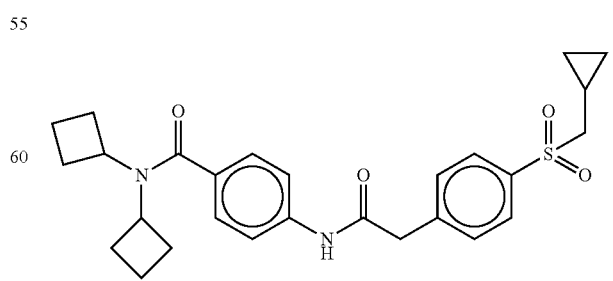

MS(ES⁺) m/z 481.2 (M+H)⁺.

28: 2-(4-cyclopropylmethanesulfonylphenyl)-N-[4-(2-methylpiperidine-1-carbonyl)phenyl]acetamide

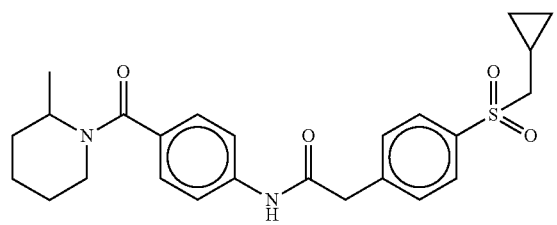

MS(ES+) m/z 455.2 (M+H)+.

29: 4-[2-(4-cyclopropylmethanesulfonylphenyl)acetamido]-N-ethyl-N-(4-methylphenyl)benzamide

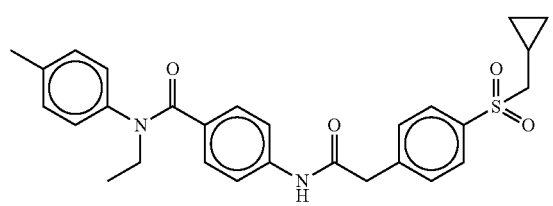

MS(ES+) m/z 491.2 (M+H)+.

30: methyl 3-{N-ethyl-4-[2-(4-cyclopropylmethanesulfonylphenyl)acetamido]benzamido}benzoate

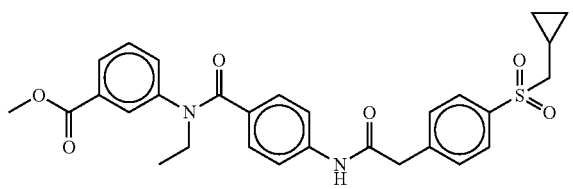

MS(ES+) m/z 535.2 (M+H)+.

31: 4-[2-(4-cyclopropylmethanesulfonylphenyl)acetamido]-N-ethyl-N-(3-methylphenyl)benzamide

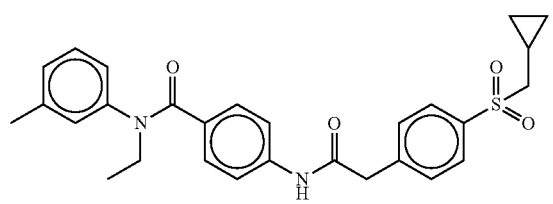

MS(ES+) m/z 491.2 (M+H)+.

32: ethyl 2-(N-benzyl-1-{4-[2-(4-cyclopropylmethanesulfonylphenyl)acetamido]phenyl}formamido)acetate

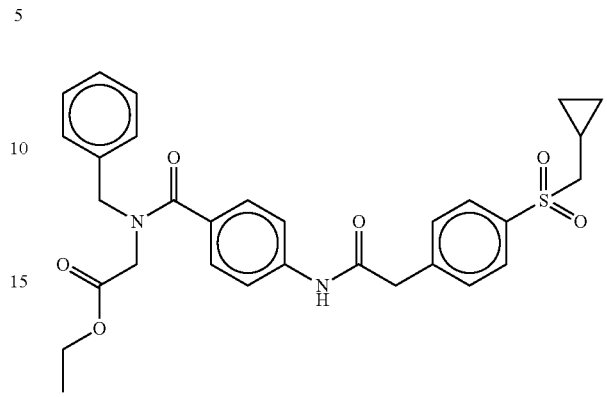

MS(ES+) m/z 549.2 (M+H)+.

33: ethyl 6-{4-[2-(4-cyclopropylmethanesulfonylphenyl)acetamido]benzoyl}-4H,5H,6H,7H-thieno[2,3-c]pyridine-2-carboxylate

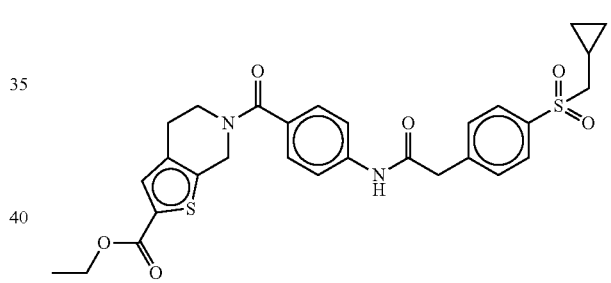

MS(ES+) m/z 567.2 (M+H)+.

34: N-cyclohexyl-4-[2-(4-cyclopropylmethanesulfonylphenyl)acetamido]-N-methylbenzamide

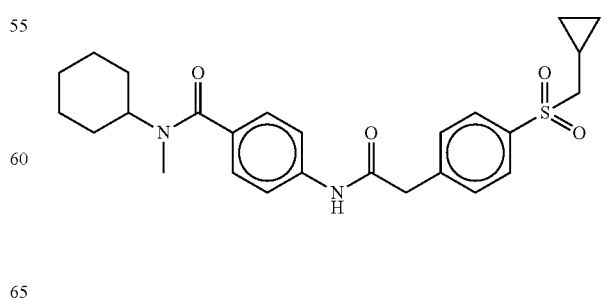

MS(ES+) m/z 469.2 (M+H)+.

35: 2-(4-cyclopropylmethanesulfonylphenyl)-N-[4-(2-phenylpyrrolidine-1-carbonyl)phenyl]acetamide

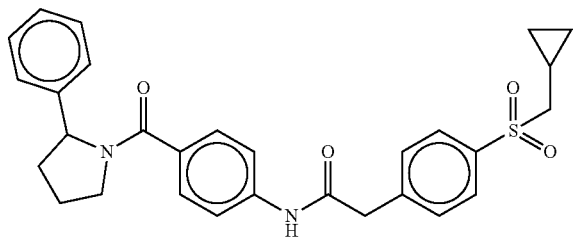

MS(ES$^+$) m/z 503.2 (M+H)$^+$.

36: 2-(4-cyclopropylmethanesulfonylphenyl)-N-[4-(piperidine-1-carbonyl)phenyl]acetamide

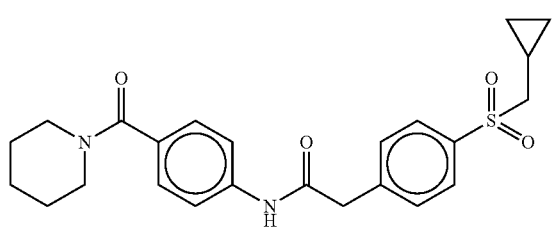

MS(ES$^+$) m/z 441.2 (M+H)$^+$.

37: 4-[2-(4-cyclopropylmethanesulfonylphenyl)acetamido]-N-(2-methylpropyl)-N-phenylbenzamide

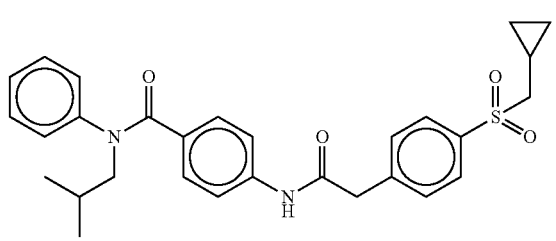

MS(ES$^+$) m/z 505.2 (M+H)$^+$.

38: ethyl 2-(1-{4-[2-(4-cyclopropylmethanesulfonylphenyl)acetamido]benzoyl}pyrrolidin-2-yl)-1,3-thiazole-4-carboxylate

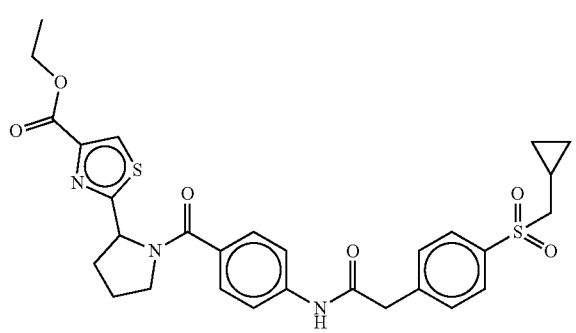

MS(ES$^+$) m/z 582.2 (M+H)$^+$.

39: 2-(4-cyclopropylmethanesulfonylphenyl)-N-{4-[2-(morpholin-4-ylmethyl)piperidine-1-carbonyl]phenyl}acetamide

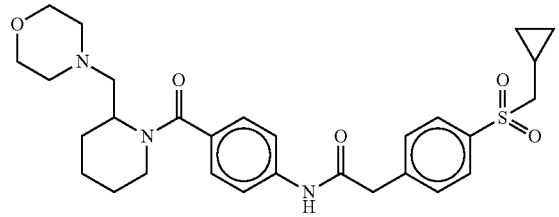

MS(ES$^+$) m/z 540.2 (M+H)$^+$.

40: 2-(4-cyclopropylmethanesulfonylphenyl)-N-[4-(1,2,3,4-tetrahydroquinoline-1-carbonyl) phenyl] acetamide

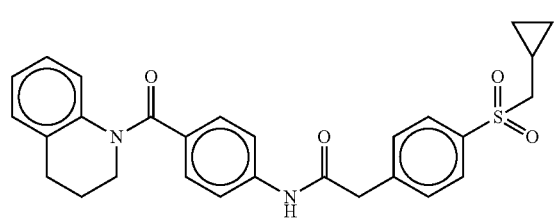

MS(ES$^+$) m/z 489.2 (M+H)$^+$.

41: 2-(4-cyclopropylmethanesulfonylphenyl)-N-[4-(2,3-dihydro-1H-indole-1-carbonyl)phenyl]acetamide

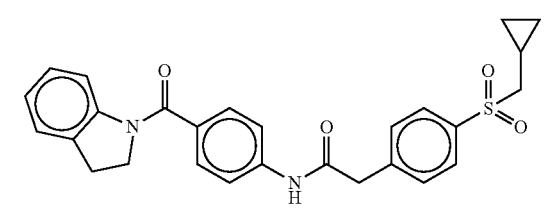

MS(ES$^+$) m/z 475.2 (M+H)$^+$.

42: N-benzyl-4-[2-(4-cyclopropylmethanesulfonylphenyl)acetamido]-N-ethylbenzamide

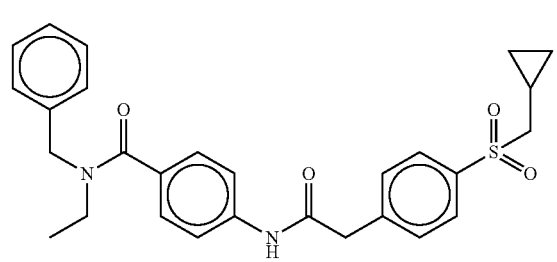

MS(ES$^+$) m/z 491.2 (M+H)$^+$.

43: 4-{2-[4-(cyclopropylsulfamoyl)phenyl]acet-amido}-N-ethyl-N-phenylbenzamide

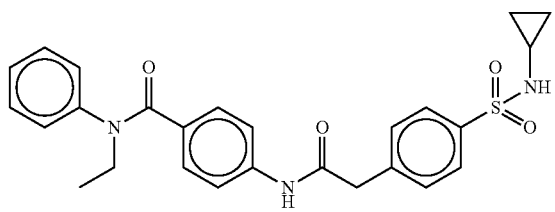

MS(ES⁺) m/z 478.2 (M+H)⁺.

44: 4-{2-[4-(cyclopropylsulfamoyl)phenyl]acet-amido}-N-methyl-N-phenylbenzamide

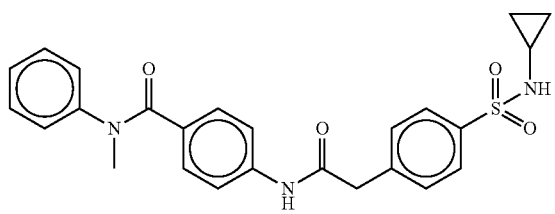

MS(ES⁺) m/z 464.2 (M+H)⁺.

45: 4-{2-[4-(cyclopropylsulfamoyl)phenyl]acet-amido}-N-ethyl-N-(4-methylphenyl) benzamide

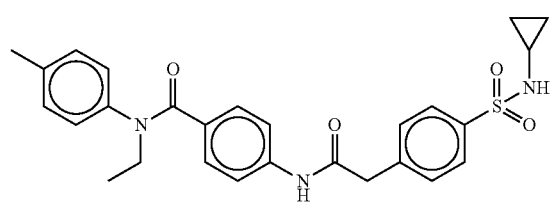

MS(ES⁺) m/z 492.2 (M+H)⁺.

46: 4-{2-[4-(cyclopropylsulfamoyl)phenyl]acet-amido}-N-ethyl-N-(3-methylphenyl) benzamide

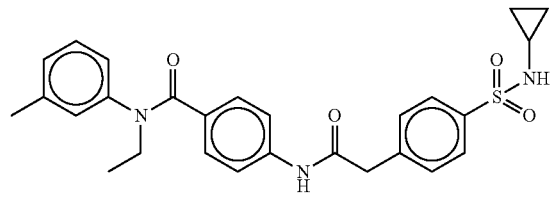

MS(ES⁺) m/z 492.2 (M+H)⁺.

47: methyl 3-(N-ethyl-4-{2-[4-(cyclopropylsulfa-moyl)phenyl]acetamido}benzamido) benzoate

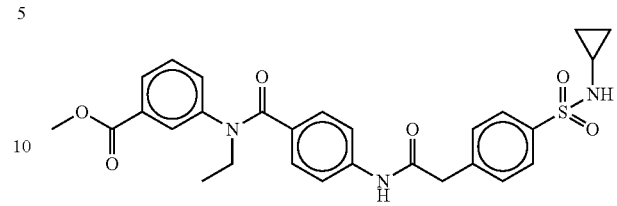

MS(ES⁺) m/z 536.2 (M+H)⁺.

48: 2-(4-cyclopropylmethanesulfonylphenyl)-N-[4-(3-phenylpiperidine-1-carbonyl)phenyl]acetamide

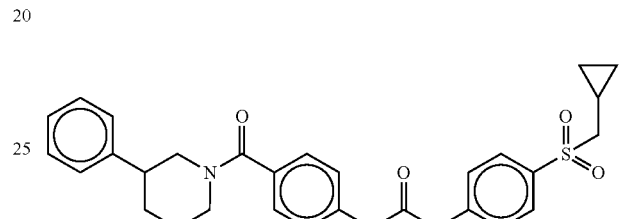

MS(ES⁺) m/z 517.2 (M+H)⁺.

49: 2-(4-cyclopropylmethanesulfonylphenyl)-N-[4-(2-phenylpiperidine-1-carbonyl)phenyl]acetamide

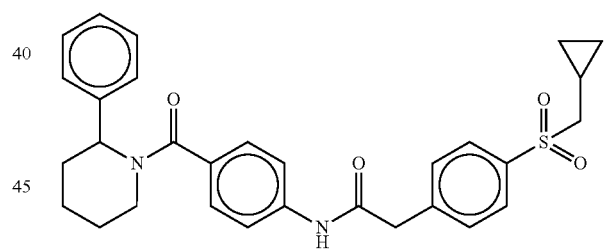

MS(ES⁺) m/z 517.2 (M+H)⁺.

50: 4-{2-[4-(cyclopropylsulfamoyl)phenyl]acet-amido}-N-ethyl-N-(pyridin-3-yl)benzamide

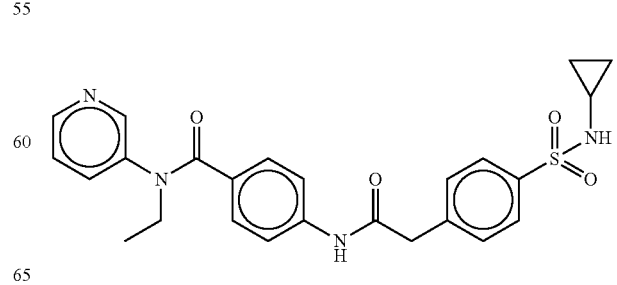

MS(ES⁺) m/z 479.2 (M+H)⁺.

51: 6-[2-(4-cyclopropylmethanesulfonylphenyl)acet-amido]-N-ethyl-N-phenylpyridine-3-carboxamide

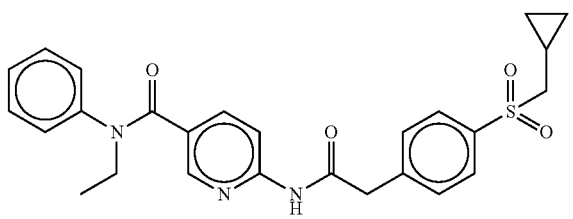

MS(ES⁺) m/z 478.2 (M+H)⁺.

52: 4-[2-(4-cyclopropylmethanesulfonylphenyl)acet-amido]-N-ethyl-N-(pyridin-3-yl) benzamide

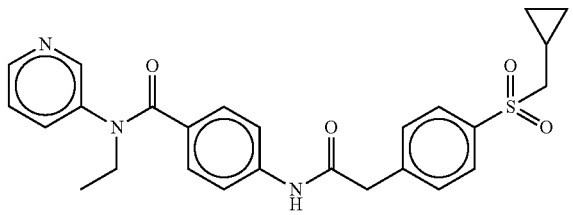

MS(ES⁺) m/z 478.2 (M+H)⁺.

53: 3-chloro-4-[2-(4-cyclopropylmethanesulfonyl-phenyl)acetamido]-N-ethyl-N-phenylbenzamide

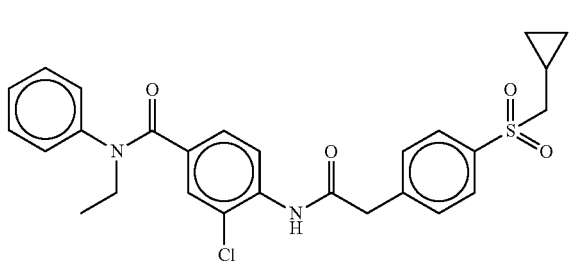

MS(ES⁺) m/z 512.2 (M+H)⁺.

54: 6-{2-[4-(cyclopropylsulfamoyl)phenyl]acet-amido}-N-ethyl-N-phenylpyridine-3-carboxamide

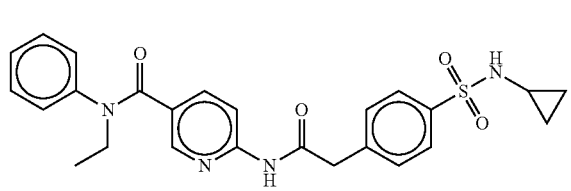

MS(ES⁺) m/z 479.2 (M+H)⁺.

55: 2-(4-cyclopropylmethanesulfonylphenyl)-N-[4-(1,2,3,4-tetrahydroisoquinoline-2-carbonyl)phenyl]acetamide

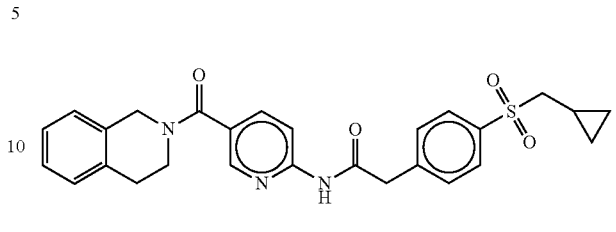

MS(ES⁺) m/z 489.2 (M+H)⁺.

56: 4-[2-(4-cyclopropylmethanesulfonylphenyl)acet-amido]-N-ethyl-N-[(5-methyl-1,2-oxazol-3-yl)methyl]benzamide

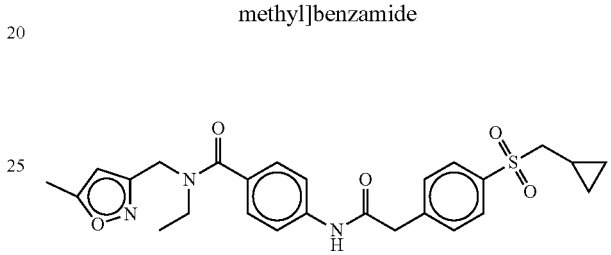

MS(ES⁺) m/z 496.2 (M+H)⁺.

57: 2-(4-cyclopropylmethanesulfonylphenyl)-N-[4-(4-methyl-2-phenylpiperazine-1-carbonyl)phenyl]acetamide

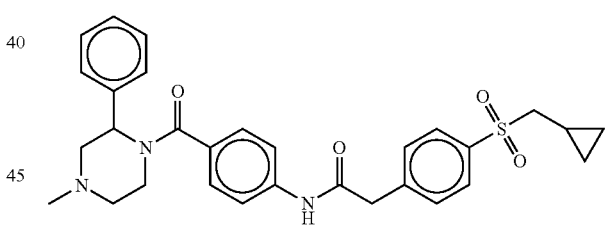

MS(ES⁺) m/z 532.3 (M+H)⁺.

58: 4-[2-(4-cyclopropylmethanesulfonylphenyl)acet-amido]-N-ethyl-2-methoxy-N-phenylbenzamide

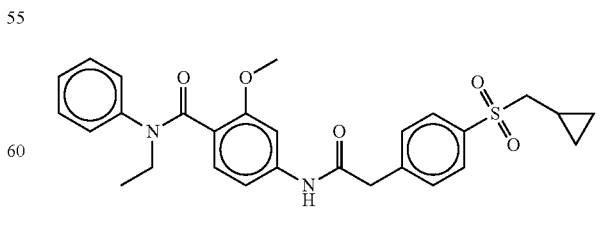

MS(ES⁺) m/z 507.2 (M+H)⁺.

59: 4-[2-(4-cyclopropylmethanesulfonylphenyl)acetamido]-N-(furan-2-ylmethyl)-N-methylbenzamide

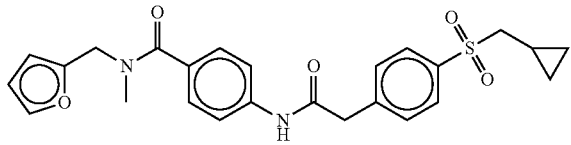

MS(ES+) m/z 467.2 (M+H)+.

60: 4-[2-(4-cyclopropylmethanesulfonylphenyl)acetamido]-N-[2-methyl-1-(morpholin-4-yl)propan-2-yl]benzamide

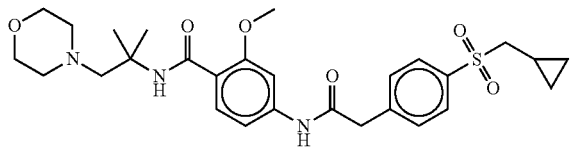

MS(ES+) m/z 514.3 (M+H)+.

61: 4-[2-(4-cyclopropylmethanesulfonylphenyl)acetamido]-N,N-bis(prop-2-en-1-yl)benzamide

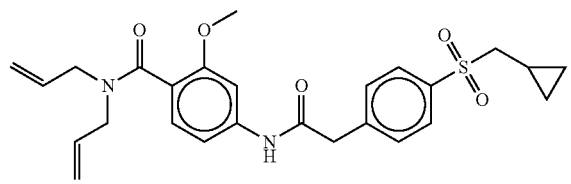

MS(ES+) m/z 453.2 (M+H)+.

62: 4-{2-[4-(cyclopropylsulfamoyl)phenyl]acetamido}-N,N-bis(2-methylpropyl)benzamide

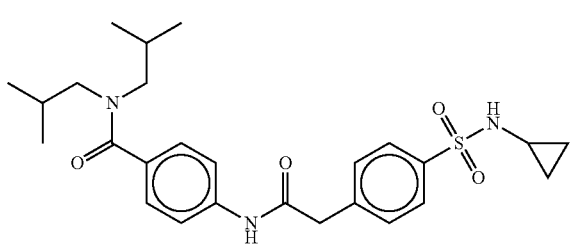

MS(ES+) m/z 486.2 (M+H)+.

63: 2-(4-cyclopropylmethanesulfonylphenyl)-N-[4-(2,3,4,5-tetrahydro-1H-1-benzazepine-1-carbonyl)phenyl]acetamide

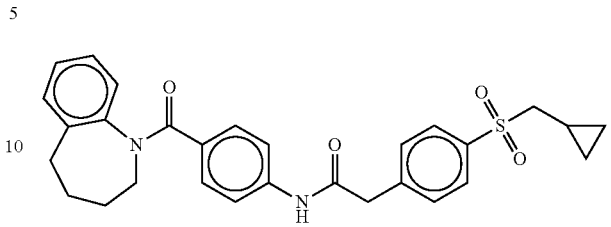

MS(ES+) m/z 503.2 (M+H)+.

64: 4-[2-(4-cyclopropylmethanesulfonylphenyl)acetamido]-N-(4-methyl-5-methyl-1,3-thiazol-2-yl)-N-ethylbenzamide

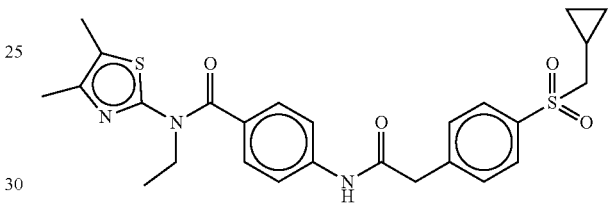

MS(ES+) m/z 512.2 (M+H)+.

65: 4-{2-[4-(cyclopropylsulfamoyl)phenyl]acetamido}-N-propyl-N-(pyridin-3-yl)benzamide

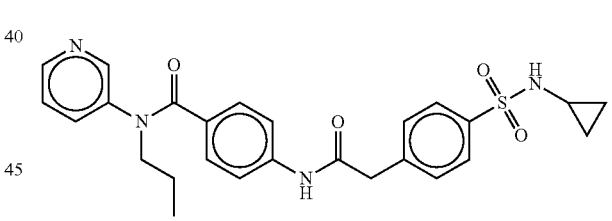

MS(ES+) m/z 493.2 (M+H)+.

66: 2-[4-(cyclopropylsulfamoyl)phenyl]-N-[4-(2-phenylpipendine-1-carbonyl)phenyl]acetamide

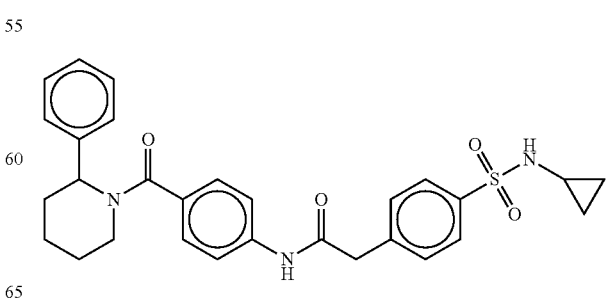

MS(ES+) m/z 518.2 (M+H)+.

67: 2-chloro-4-[2-(4-cyclopropylmethanesulfonyl-phenyl)acetamido]-N-methyl-N-(pyridin-2-yl)benzamide

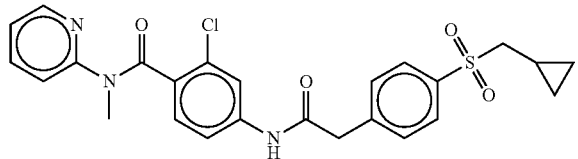

MS(ES+) m/z 498.2 (M+H)+.

68: 4-[2-(4-cyclopropylmethanesulfonylphenyl)acetamido]-N-[2-(pyridin-3-yl)propan-2-yl]benzamide

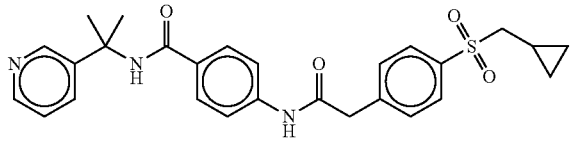

MS(ES+) m/z 492.2 (M+H)+.

69: 4-[2-(4-cyclopropylmethanesulfonylphenyl)acetamido]-N-[(2R)-1,1,1-trifluoro-3-methylbutan-2-yl]benzamide

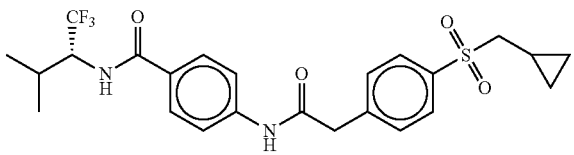

MS(ES+) m/z 497.2 (M+H)+.

70: 4-[2-(4-cyclopropylmethanesulfonylphenyl)acetamido]-N-[(1S)-1-(2-methoxyphenyl)ethyl]benzamide

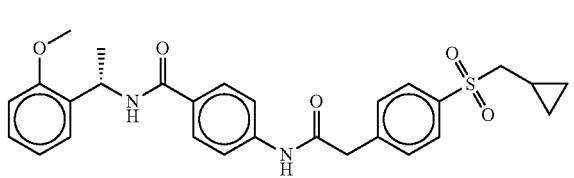

MS(ES+) m/z 507.2 (M+H)+.

71: 4-[2-(4-cyclopropylmethanesulfonylphenyl)acetamido]-N-[(1S)-1-(2-fluorophenyl)ethyl]benzamide

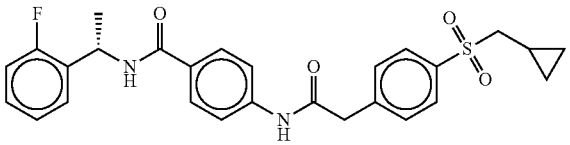

MS(ES+) m/z 495.2 (M+H)+.

72: N-[cyano(thiophen-2-yl)methyl]-4-[2-(4-cyclopropylmethanesulfonylphenyl) acetamido]benzamide

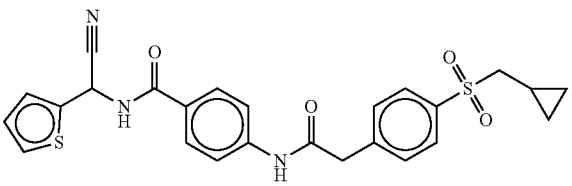

MS(ES+) m/z 495.2 (M+H)+.

73: N-[cyano(phenyl)methyl]-4-[2-(4-cyclopropylmethanesulfonylphenyl) acetamido]benzamide

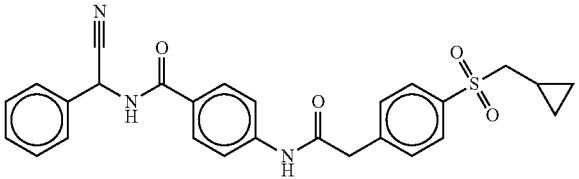

MS(ES+) m/z 488.2 (M+H)+.

74: 4-[2-(4-cyclopropylmethanesulfonylphenyl)acetamido]-N-[2-(trifluoromethoxy)phenyl]benzamide

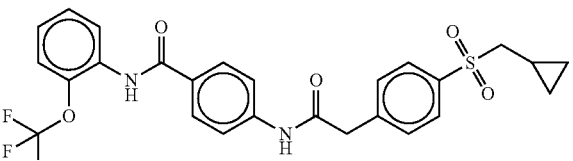

MS(ES+) m/z 533.2 (M+H)+.

75: 4-[2-(4-cyclopropylmethanesulfonylphenyl)acet-
amido]-N-(2,6-dimethylphenyl) benzamide

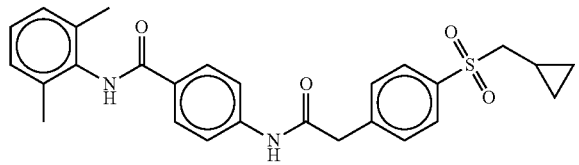

MS(ES+) m/z 477.2 (M+H)+.

76: N-[(1R)-1-(4-chlorophenyl)-2,2,2-trifluoro-
ethyl]-4-[2-(4-cyclopropylmethanesulfonylphenyl)
acetamido]benzamide

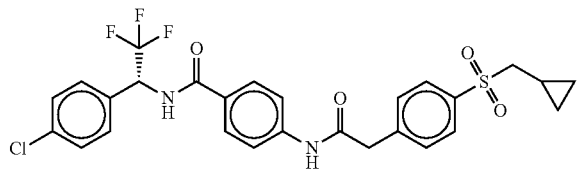

MS(ES+) m/z 565.2 (M+H)+.

77: N-cyclopropyl-4-[[2-[4-(cyclopropylmethylsul-
fonyl)phenyl]acetyl]amino]-N-(2-hydroxyethyl)ben-
zamide

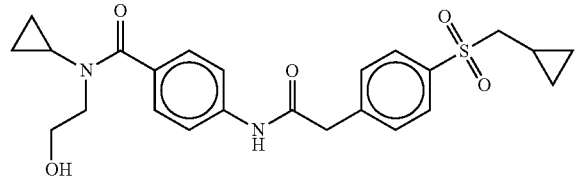

MS(ES+) m/z 457.1 (M+H)+.

78: N-cyclopropyl-4-[[2-[4-(cyclopropylmethylsul-
fonyl)phenyl]acetyl]amino]-N-[(1-hydroxycyclobu-
tyl)methyl]benzamide

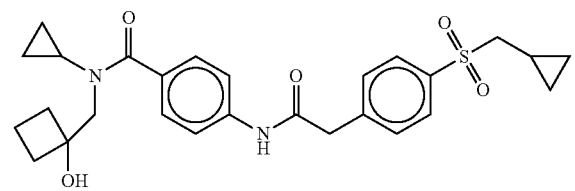

MS(ES+) m/z 497.2 (M+H)+.

79: N-cyclopropyl-4-[[2-[4-(cyclopropylmethylsul-
fonyl)phenyl]acetyl]amino]-N-(2-methoxyethyl)
benzamide

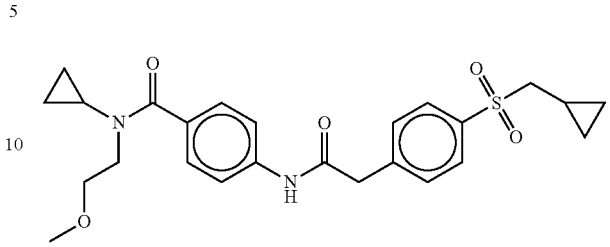

MS(ES+) m/z 471.2 (M+H)+.

80: N-cyclopropyl-4-[[2-[4-(cyclopropylmethylsul-
fonyl)phenyl]acetyl]amino]-N-tetrahydropyran-4-yl-
benzamide

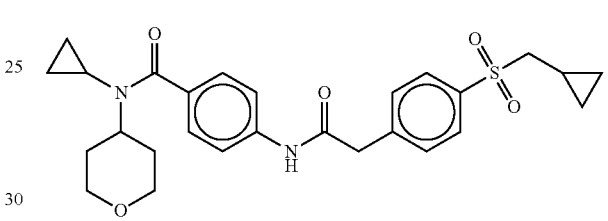

MS(ES+) m/z 497.2 (M+H)+.

81: 4-[2-(4-cyclopropylmethanesulfonylphenyl)acet-
amido]-N-propyl-N-(thiophen-3-yl)benzamide

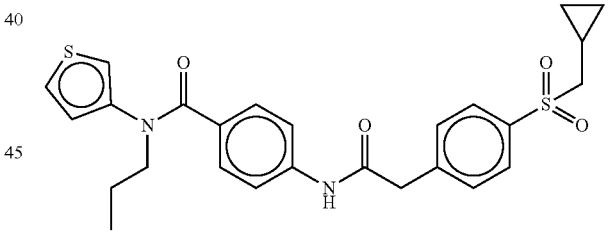

i) To a solution of N-propylthiophen-3-amine (147 mg) and triethyl amine (283 uL) in CH$_2$Cl$_2$ (2 mL) was added a solution of 4-nitrobenzoyl chloride (218 mg) in CH$_2$Cl$_2$ (2 mL) and the reaction mixture was stirred overnight at room temperature. Water was added and the organic phase was washed with a 1N aqueous HCl solution, water, a saturated aqueous NaHCO$_3$ solution, water and brine. The organic phase was dried over MgSO$_4$ and concentrated under reduced pressure. The residue was purified on SiO$_2$, using 10% to 30% ethyl acetate in toluene, as the eluent, giving 4-nitro-N-propyl-N-(thiophen-3-yl)benzamide (80 mg).

ii) To a solution of the product obtained in the previous step (81 mg) in ethanol (20 mL) was added at room temperature SnCl$_2$ (264 mg) and the reaction was stirred for 1 hour at 70° C. The reaction mixture was quenched by pouring onto ice and a 2N aqueous NaOH solution was added dropwise until pH=4. The product was extracted into ethyl acetate and the organic phase was washed with water, brine, dried over MgSO₄ and concentrated under reduced pressure giving 4-amino-N-propyl-N-(thiophen-3-yl)benzamide (66 mg). The product was used in the next step without further purification.

iii) Following a procedure analogous to that described in Example 1, step iv), the product obtained in the previous step (66 mg) was converted to the title compound 4-[2-(4-cyclopropylmethanesulfonylphenyl)acetamido]-N-propyl-N-(thiophen-3-yl)benzamide (72 mg). MS(ES⁺) m/z 496.6 (M+H)⁺.

Following a procedure analogous to that described for Example 81, using appropriate starting materials, the following compounds have been prepared.

82: N-butyl-4-[2-(4-cyclopropylmethanesulfonylphenyl)acetamido]-N-(1,3-thiazol-2-yl)benzamide

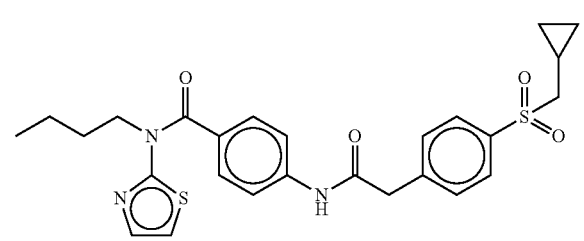

MS(ES⁺) m/z 512.2 (M+H)⁺.

83: 4-[2-(4-cyclopropylmethanesulfonylphenyl)acetamido]-N-propyl-N-(1,3-thiazol-2-yl)benzamide

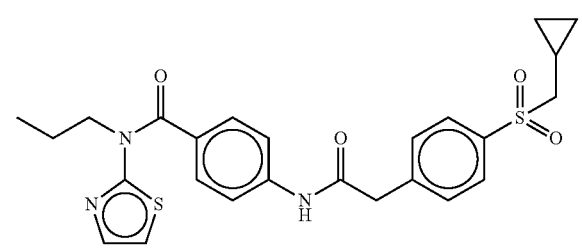

MS(ES⁺) m/z 498.2 (M+H)⁺.

84: 4-[2-(4-cyclopropylmethanesulfonylphenyl)acetamido]-N-ethyl-N-(1,3-thiazol-2-yl)benzamide

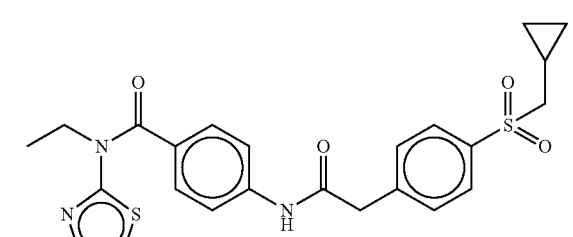

MS(ES⁺) m/z 484.2 (M+H)⁺.

85: 4-[2-(4-cyclopropylmethanesulfonylphenyl)acetamido]-N-methyl-N-(1,3-thiazol-2-yl)benzamide

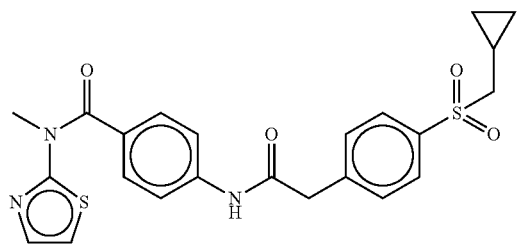

MS(ES⁺) m/z 470.2 (M+H)⁺.

86: 4-[2-(4-cyclopropylmethanesulfonylphenyl)acetamido]-N-(1,3-dimethyl-1H-pyrazol-5-yl)-N-propylbenzamide

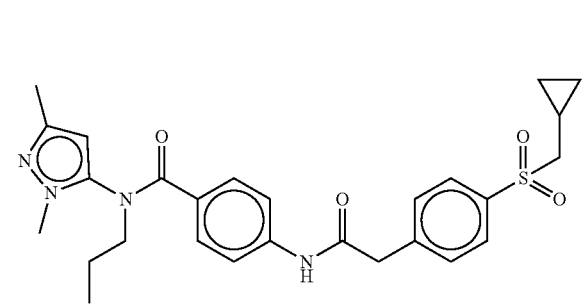

MS(ES⁺) m/z 509.2 (M+H)⁺.

87: 4-[2-(4-cyclopropylmethanesulfonylphenyl)acetamido]-N-(5-methyl-1,2-oxazol-3-yl)-N-propylbenzamide

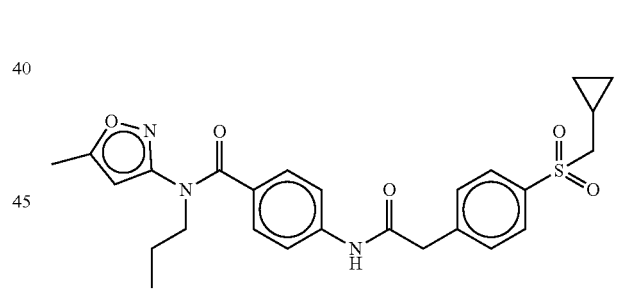

MS(ES⁺) m/z 496.2 (M+H)⁺.

88: 4-[2-(4-cyclopropylmethanesulfonylphenyl)acetamido]-N-(1,3-dimethyl-1H-pyrazol-5-yl)-N-ethylbenzamide

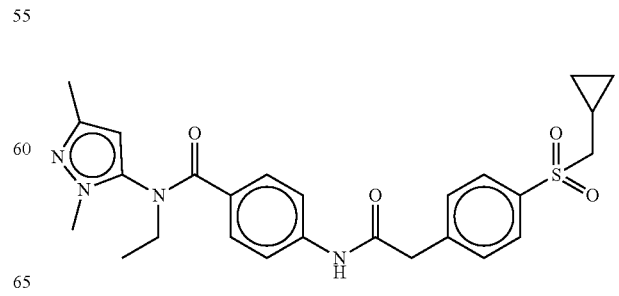

MS(ES⁺) m/z 495.2 (M+H)⁺.

89: 4-[2-(4-cyclopropylmethanesulfonylphenyl)acetamido]-N-ethyl-N-(5-methyl-1,2-oxazol-3-yl)benzamide

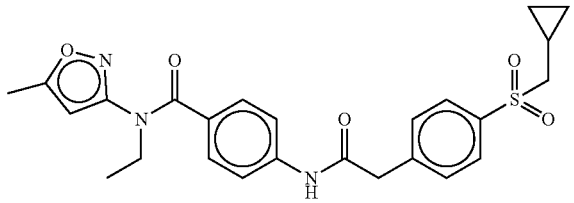

MS(ES⁺) m/z 482.2 (M+H)⁺.

90: 4-[2-(4-cyclopropylmethanesulfonylphenyl)acetamido]-N-methyl-N-(5-methyl-1,2-oxazol-3-yl)benzamide

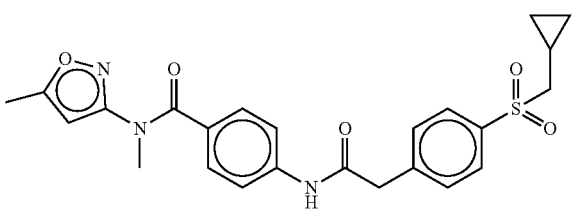

MS(ES⁺) m/z 468.2 (M+H)⁺.

91: 4-{2-[4-(cyclopropylsulfamoyl)phenyl]acetamido}-N-methyl-N-(5-methyl-1,2-oxazol-3-yl)benzamide

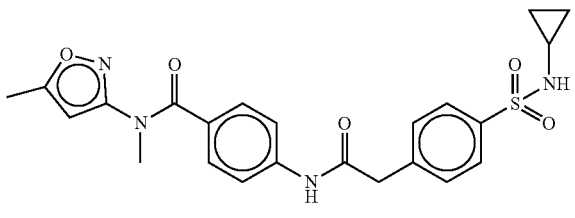

MS(ES⁺) m/z 469.2 (M+H)⁺.

92: 4-{2-[4-(cyclopropylsulfamoyl)phenyl]acetamido}-N-(1,3-dimethyl-1H-pyrazol-5-yl)-N-propylbenzamide

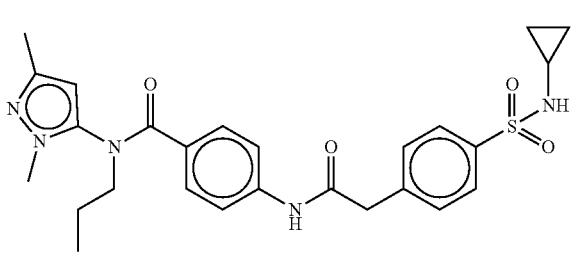

MS(ES⁺) m/z 510.2 (M+H)⁺.

93: 4-{2-[4-(cyclopropylsulfamoyl)phenyl]acetamido}-N-(5-methyl-1,2-oxazol-3-yl)-N-propylbenzamide

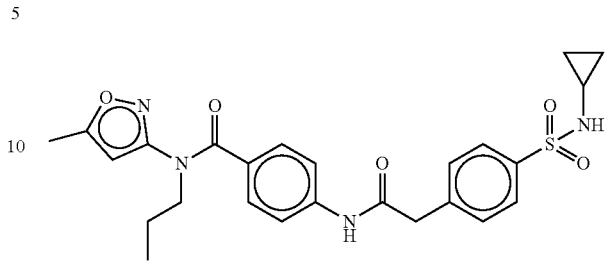

MS(ES⁺) m/z 497.2 (M+H)⁺.

94: 4-[2-(4-cyclopropylmethanesulfonylphenyl)acetamido]-N-ethyl-N-(3-methyl-1,2-oxazol-5-yl)benzamide

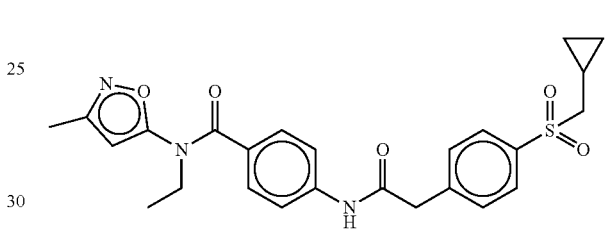

MS(ES⁺) m/z 482.2 (M+H)⁺.

95: 4-{2-[4-(cyclopropylsulfamoyl)phenyl]acetamido}-N-ethyl-N-(3-methyl-1,2-oxazol-5-yl)benzamide

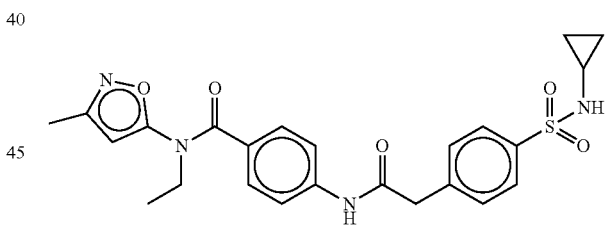

MS(ES⁺) m/z 483.2 (M+H)⁺.

96: 4-[2-(4-cyclopropylmethanesulfonylphenyl)acetamido]-N-ethyl-N-(5-methyl-1,3,4-thiadiazol-2-yl)benzamide

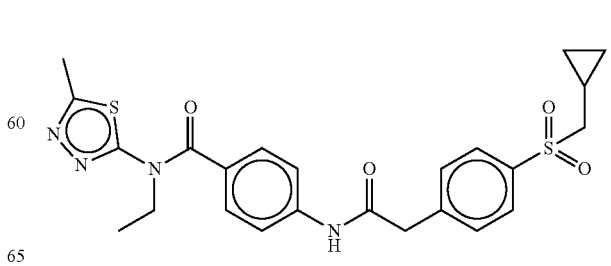

MS(ES⁺) m/z 499.2 (M+H)⁺.

97: 4-{2-[4-(cyclopropylsulfamoyl)phenyl]acet-amido}-N-ethyl-N-(5-methyl-1,3,4-thiadiazol-2-yl)benzamide

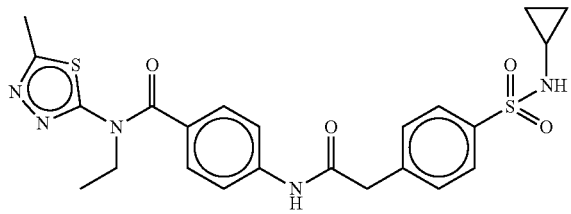

MS(ES⁺) m/z 500.2 (M+H)⁺.

98: 4-{2-[4-(cyclopropylsulfamoyl)phenyl]acet-amido}-N-ethyl-3-methoxy-N-phenylbenzamide

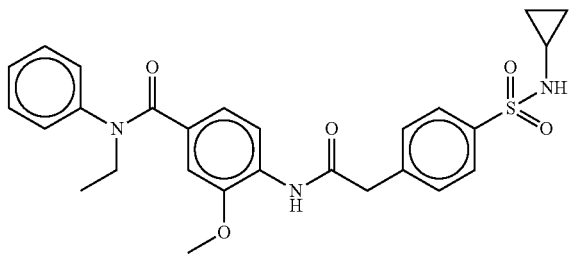

MS(ES⁺) m/z 508.2 (M+H)⁺.

99: 4-[2-(4-cyclopropylmethanesulfonylphenyl)acet-amido]-N-ethyl-2-fluoro-N-phenylbenzamide

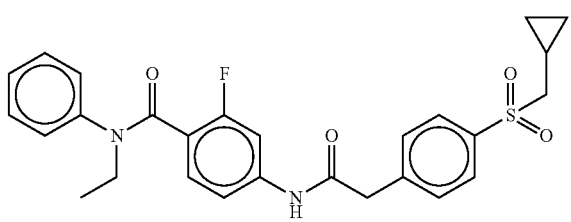

MS(ES⁺) m/z 495.2 (M+H)⁺.

100: 2-chloro-4-[2-(4-cyclopropylmethanesulfonyl-phenyl)acetamido]-N-ethyl-N-phenylbenzamide

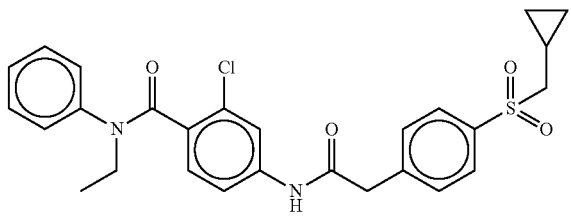

MS(ES⁺) m/z 512.1 (M+H)⁺.

101: 4-[2-(4-cyclopropylmethanesulfonylphenyl)acetamido]-N-ethyl-3-methoxy-N-phenylbenzamide

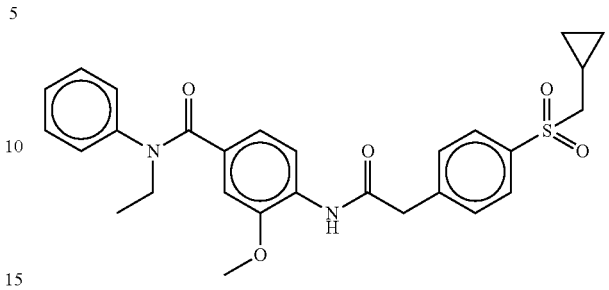

MS(ES⁺) m/z 507.2 (M+H)⁺.

102: 4-[2-(4-cyclopropylmethanesulfonylphenyl)acetamido]-N-ethyl-3-fluoro-N-phenylbenzamide

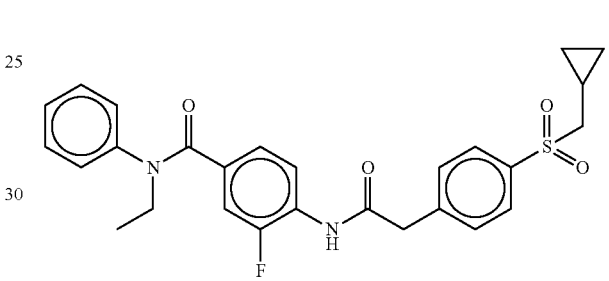

MS(ES⁺) m/z 495.2 (M+H)⁺.

103: 4-[2-(4-cyclopropylmethanesulfonylphenyl)acetamido]-N-ethyl-N-(1,2-oxazol-3-yl)benzamide

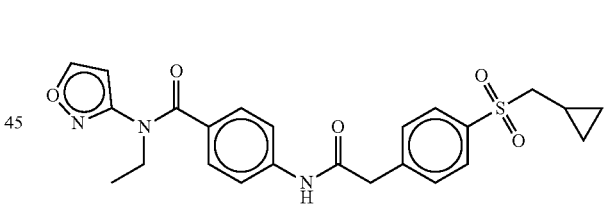

MS(ES⁺) m/z 468.2 (M+H)⁺.

104: 4-[2-(4-cyclopropylmethanesulfonylphenyl)acetamido]-N-phenyl-N-(2,2,2-trifluoroethyl)benz-amide

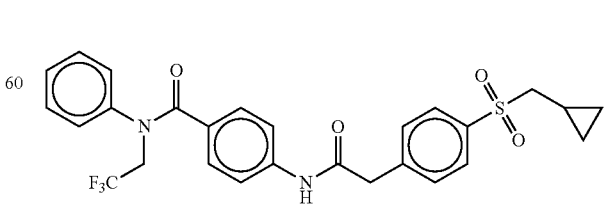

MS(ES⁺) m/z 531.2 (M+H)⁺.

105: 4-[2-(4-cyclopropylmethanesulfonylphenyl)acetamido]-N-ethyl-3-methyl-N-phenylbenzamide

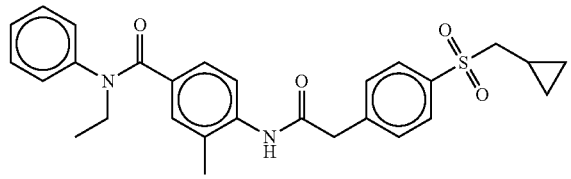

MS(ES⁺) m/z 491.2 (M+H)⁺.

106: 4-{2-[4-(cyclopropylsulfamoyl)phenyl]acetamido}-N-ethyl-3-methyl-N-phenylbenzamide

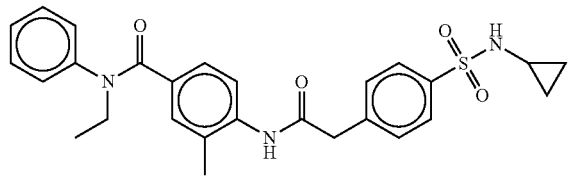

MS(ES⁺) m/z 492.2 (M+H)⁺.

107: 4-{2-[4-(cyclopropylsulfamoyl)phenyl]acetamido}-N-(4-methyl-5-methyl-1,3-thiazol-2-yl)-N-ethyl-benzamide

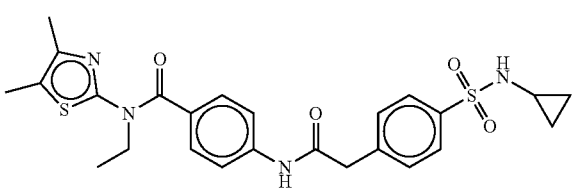

MS(ES⁺) m/z 513.2 (M+H)⁺.

108: 4-[2-(4-cyclopropylmethanesulfonylphenyl)acetamido]-N-(dimethyl-1,2-oxazol-4-yl)-N-ethyl-benzamide

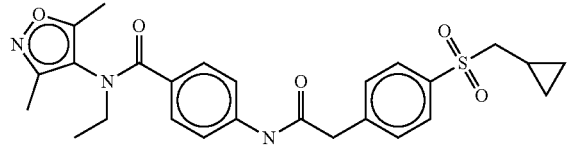

MS(ES⁺) m/z 496.2 (M+H)⁺.

109: 4-{2-[4-(cyclopropylsulfamoyl)phenyl]acetamido}-N-phenyl-N-(2,2,2-trifluoroethyl) benzamide

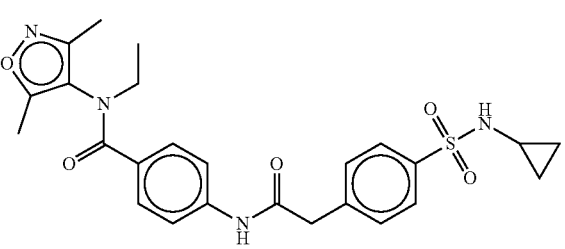

MS(ES⁺) m/z 532.2 (M+H)⁺.

110: 4-{2-[4-(cyclopropylsulfamoyl)phenyl]acetamido}-N-(dimethyl-1,2-oxazol-4-yl)-N-ethylbenzamide MS(ES⁺) m/z 497.2 (M+H)⁺.

111: 4-{2-[4-(cyclopropylsulfamoyl)phenyl]acetamido}-N-ethyl-2-fluoro-N-phenylbenzamide

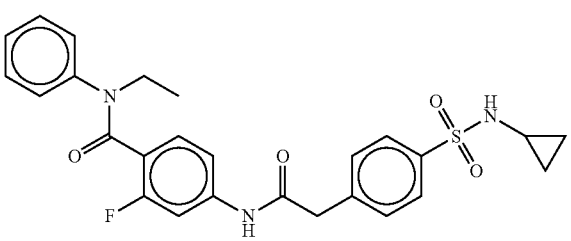

MS(ES⁺) m/z 496.2 (M+H)⁺.

112: 2-chloro-4-{2-[4-(cyclopropylsulfamoyl)phenyl]acetamido}-N-ethyl-N-phenylbenzamide

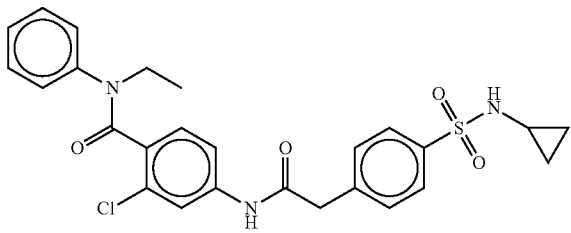

MS(ES$^+$) m/z 513.2 (M+H)$^+$.

113: N-benzyl-N-tert-butyl-4-[2-(4-cyclopropylmethanesulfonylphenyl)acetamido]benzamide

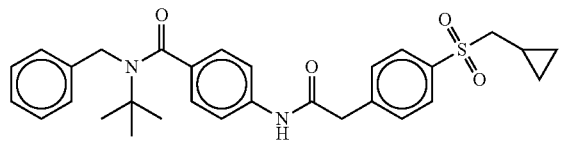

MS(ES$^+$) m/z 519.2 (M+H)$^+$.

114: 4-[2-(4-cyclopropylmethanesulfonylphenyl)acetamido]-N-(1-methylpiperidin-4-yl)-N-phenylbenzamide

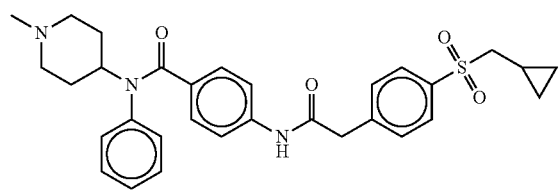

MS(ES$^+$) m/z 546.3 (M+H)$^+$.

115: N-(4-bromophenyl)-4-[2-(4-cyclopropylmethanesulfonylphenyl)acetamido]-N-phenylbenzamide

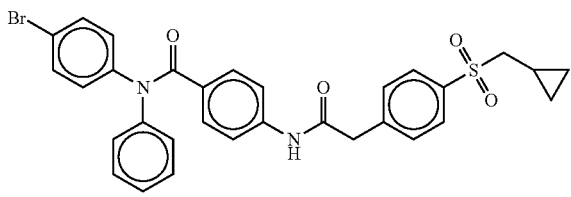

MS(ES$^+$) m/z 602.1 (M+H)$^+$.

116: 4-[2-(4-cyclopropylmethanesulfonylphenyl)acetamido]-2-fluoro-N-methyl-N-(2-methylphenyl)benzamide

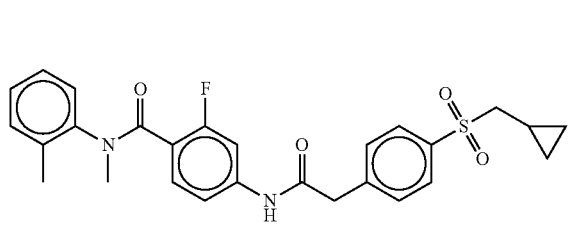

MS(ES$^+$) m/z 495.2 (M+H)$^+$.

117: 2-chloro-4-[2-(4-cyclopropylmethanesulfonylphenyl)acetamido]-N-methyl-N-(2-methylphenyl)benzamide

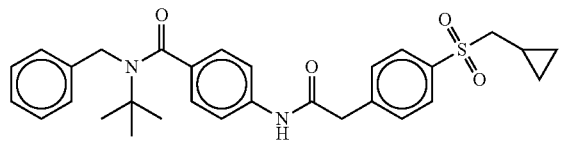

MS(ES$^+$) m/z 511.2 (M+H)$^+$.

118: N-(2-chlorophenyl)-4-[2-(4-cyclopropylmethanesulfonylphenyl)acetamido]-N-ethyl-2-fluorobenzamide

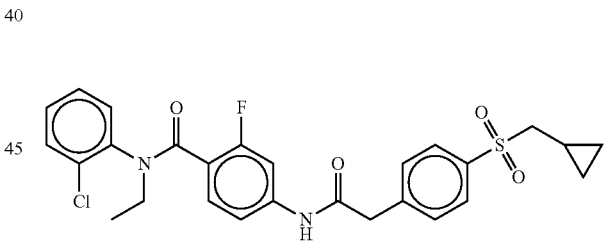

MS(ES$^+$) m/z 529.2 (M+H)$^+$.

119: 4-[2-(4-cyclopropylmethanesulfonylphenyl)acetamido]-N-(2,3-dimethylphenyl)-N-ethyl-2-fluorobenzamide

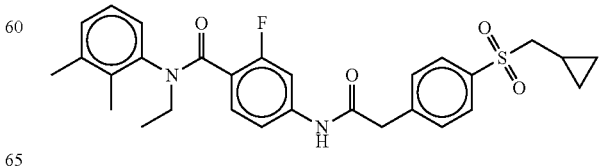

MS(ES$^+$) m/z 523.3 (M+H)$^+$.

120: 2-chloro-4-[2-(4-cyclopropylmethanesulfonyl-phenyl)acetamido]-N-(2,3-dimethylphenyl)-N-ethyl-benzamide

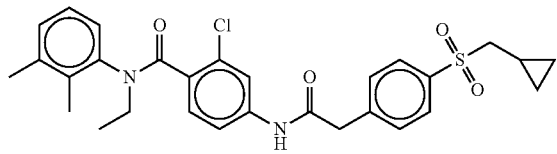

MS(ES⁺) m/z 539.3 (M+H)⁺.

121: N-[4-(3-tert-butyl-3,4-dihydro-2H-1,4-benzox-azine-4-carbonyl)phenyl]-2-(4-cyclopropylmethane-sulfonylphenyl)acetamide

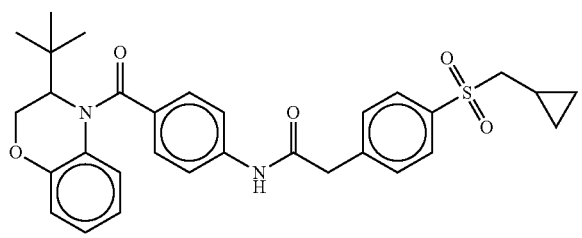

MS(ES⁺) m/z 547.3 (M+H)⁺.

122: 4-[2-(4-cyclopropylmethanesulfonylphenyl)acetamido]-N-(2-methoxyphenyl)-N,2-dimethylben-zamide

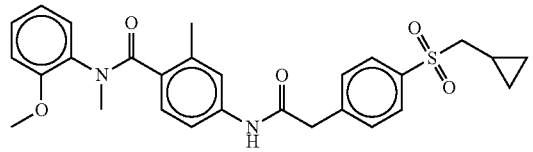

MS(ES⁺) m/z 507.3 (M+H)⁺.

123: 2-chloro-4-[2-(4-cyclopropylmethanesulfonyl-phenyl)acetamido]-N-phenyl-N-(2,2,2-trifluoroethyl)benzamide

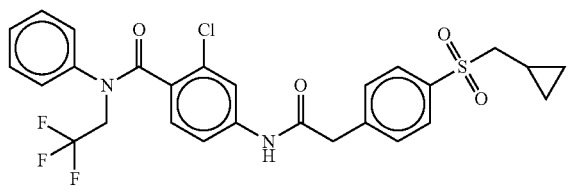

MS(ES⁺) m/z 565.2 (M+H)⁺.

124: 4-[2-(4-cyclopropylmethanesulfonylphenyl)acetamido]-2-fluoro-N-(2-methoxyphenyl)-N-methylbenzamide

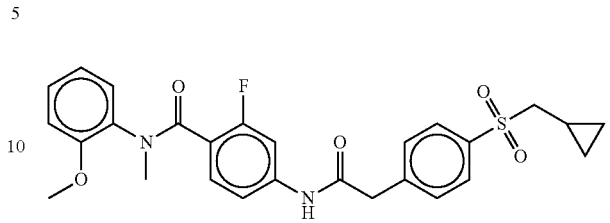

MS(ES⁺) m/z 511.3 (M+H)⁺.

125: 2-chloro-4-[2-(4-cyclopropylmethanesulfonyl-phenyl)acetamido]-N-(2-methoxyphenyl)-N-methyl-benzamide

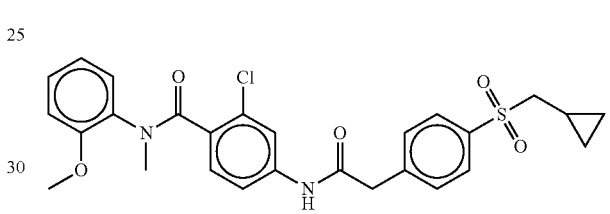

MS(ES⁺) m/z 527.2 (M+H)⁺.

126: 4-[2-(4-cyclopropylmethanesulfonylphenyl)acetamido]-2-fluoro-N-(2-fluorophenyl)-N-methyl-benzamide

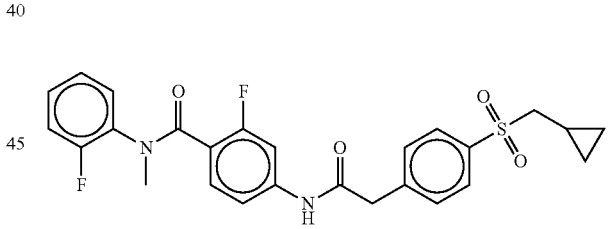

MS(ES⁺) m/z 499.2 (M+H)⁺.

127: 2-chloro-4-[2-(4-cyclopropylmethanesulfonyl-phenyl)acetamido]-N-(2-fluorophenyl)-N-methyl-benzamide

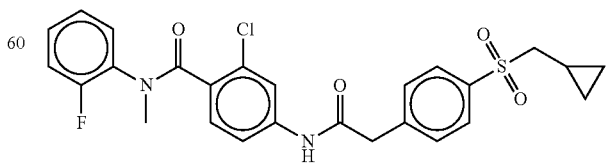

MS(ES⁺) m/z 515.2 (M+H)⁺.

128: 2-chloro-N-(2-chlorophenyl)-4-[2-(4-cyclopropylmethanesulfonylphenyl)acetamido]-N-ethylbenzamide

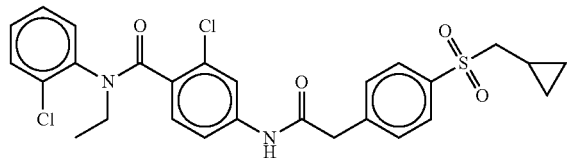

MS(ES⁺) m/z 545.2 (M+H)⁺.

129: 2-chloro-4-[2-(4-cyclopropylmethanesulfonylphenyl)acetamido]-N-ethyl-N-(2-methylphenyl)benzamide

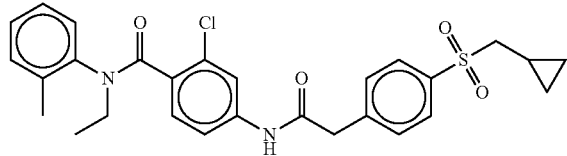

MS(ES⁺) m/z 525.3 (M+H)⁺.

130: N-tert-butyl-4-[2-(4-cyclopropylmethanesulfonylphenyl)acetamido]-N-phenylbenzamide

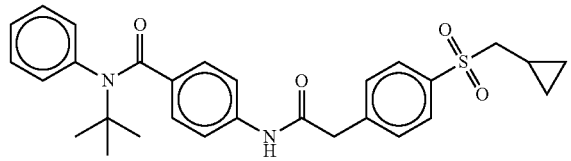

MS(ES⁺) m/z 505.3 (M+H)⁺.

131: N-tert-butyl-4-{2-[4-(cyclopropylsulfamoyl)phenyl]acetamido}-N-phenylbenzamide

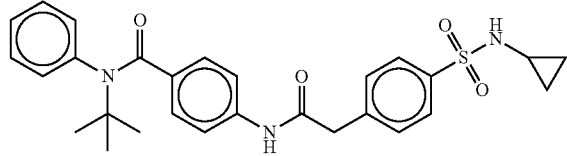

MS(ES⁺) m/z 506.3 (M+H)⁺.

132: 4-{2-[4-(cyclopropylsulfamoyl)phenyl]acetamido}-N-(4-methylphenyl)-N-[2-(oxolan-2-yl)propan-2-yl]benzamide

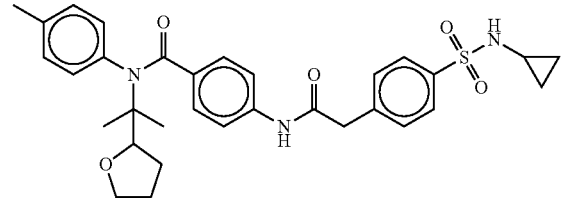

MS(ES⁺) m/z 576.2 (M+H)⁺.

133: 4-[2-(4-cyclopropylmethanesulfonylphenyl)acetamido]-N-(4-methylphenyl)-N-[2-(oxolan-2-yl)propan-2-yl]benzamide

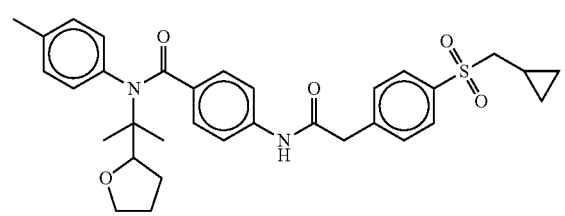

MS(ES⁺) m/z 575.2 (M+H)⁺.

134: N-tert-butyl-4-[2-(4-cyclopropylmethanesulfonylphenyl)acetamido]-3-fluoro-N-phenylbenzamide

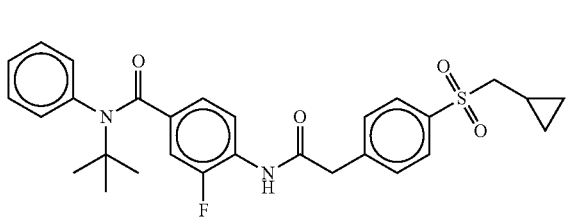

MS(ES⁺) m/z 523.2 (M+H)⁺.

135: 4-[2-(4-cyclopropylmethanesulfonylphenyl)acetamido]-N-[2-(oxolan-2-yl)propan-2-yl]-N-phenylbenzamide

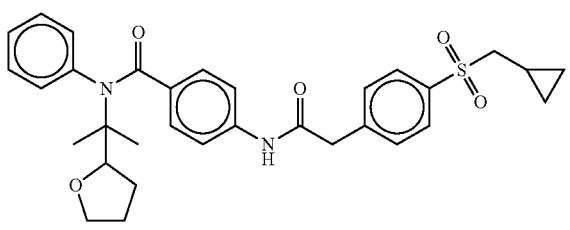

MS(ES⁺) m/z 561.2 (M+H)⁺.

136: 4-[2-(4-cyclopropylmethanesulfonylphenyl)acetamido]-N-(oxolan-3-yl)-N-(pyridin-2-yl)benzamide

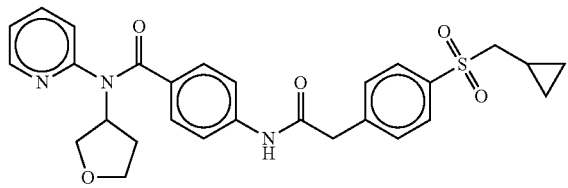

MS(ES⁺) m/z 520.1 (M+H)⁺.

137: N-cyclopropyl-4-[2-(4-cyclopropylmethanesulfonylphenyl)acetamido]-N-(pyridin-2-yl)benzamide

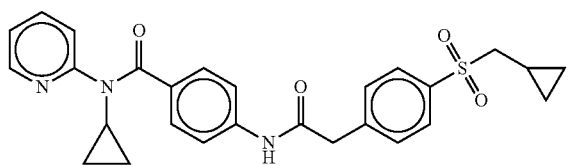

MS(ES⁺) m/z 490.1 (M+H)⁺.

138: 4-[2-(4-cyclopropylmethanesulfonylphenyl)acetamido]-N-(1-hydroxy-2-methylpropan-2-yl)-N-phenylbenzamide

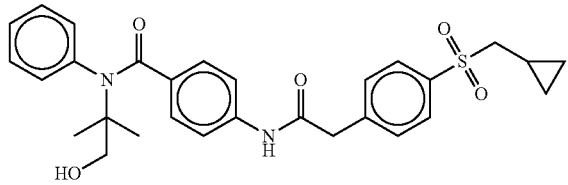

MS(ES⁺) m/z 521.2 (M+H)⁺.

139: N-cyclobutyl-4-[2-(4-cyclopropylmethanesulfonylphenyl)acetamido]-N-(pyridin-2-yl)benzamide

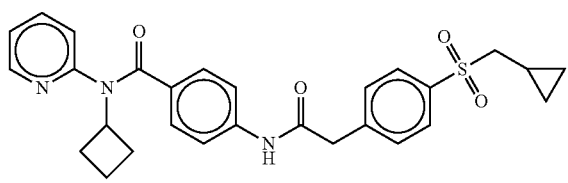

MS(ES⁺) m/z 504.2 (M+H)⁺.

140: N-cyclopropyl-4-[2-(4-cyclopropylmethanesulfonylphenyl)acetamido]-N-phenylbenzamide

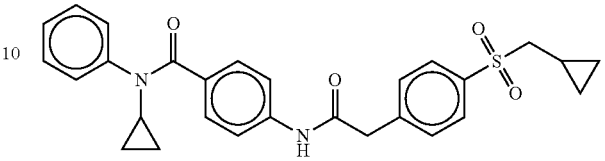

MS(ES⁺) m/z 489.1 (M+H)⁺.

141: N-cyclobutyl-4-[2-(4-cyclopropylmethanesulfonylphenyl)acetamido]-N-phenylbenzamide

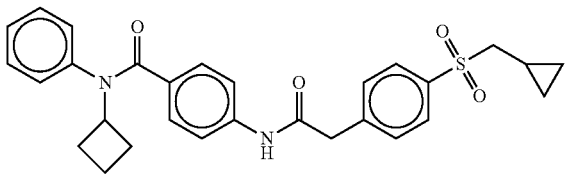

MS(ES⁺) m/z 503.2 (M+H)⁺.

142: 4-[2-(4-cyclopropylmethanesulfonylphenyl)acetamido]-N-(1-methylcyclopropyl)-N-phenylbenzamide

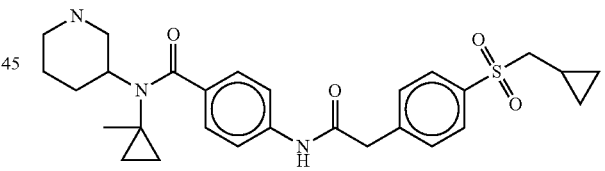

MS(ES⁺) m/z 503.2 (M+H)⁺.

143: N-cyclopropyl-4-[2-(4-cyclopropylmethanesulfonylphenyl)acetamido]-N-(pyridin-3-yl)benzamide

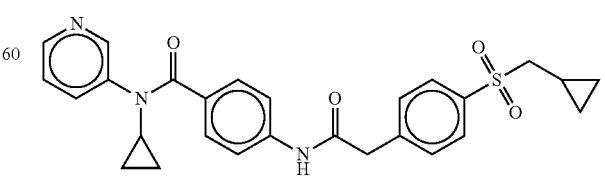

MS(ES⁺) m/z 490.1 (M+H)⁺.

144: 4-[2-(4-cyclopropylmethanesulfonylphenyl)acetamido]-N-(3,3-difluorocyclobutyl)-N-phenyl-benzamide

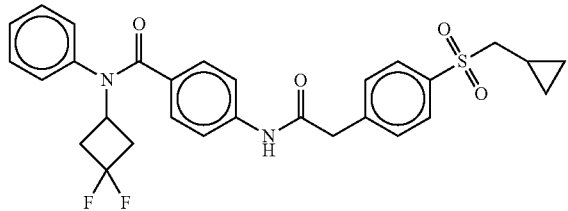

MS(ES⁺) m/z 539.1 (M+H)⁺.

145: methyl 2-(1-{4-[2-(4-cyclopropylmethanesulfonylphenyl)acetamido]phenyl}-N-phenylformamido)-2-methylpropanoate

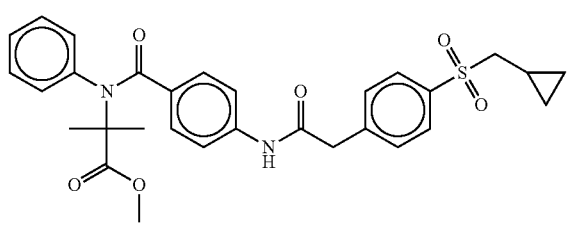

MS(ES⁺) m/z 549.1 (M+H)⁺.

146: 4-[2-(4-cyclopropylmethanesulfonylphenyl)acetamido]-N-phenyl-N-(1,1,1-trifluoropropan-2-yl)benzamide

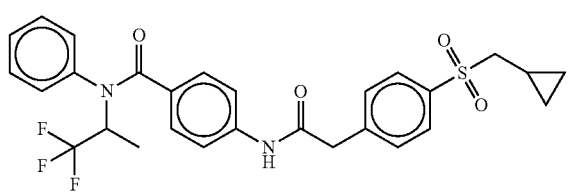

MS(ES⁺) m/z 545.1 (M+H)⁺.

147: 4-[2-(4-cyclopropylmethanesulfonylphenyl)acetamido]-N-(2,6-dichlorophenyl)benzamide

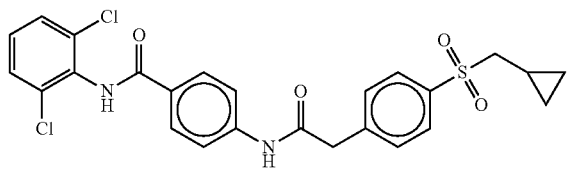

MS(ES⁺) m/z 517.1 (M+H)⁺.

148: 4-{2-[4-(cyclopropylsulfamoyl)phenyl]acetamido}-N-phenyl-N-(1,1,1-trifluoropropan-2-yl)benzamide

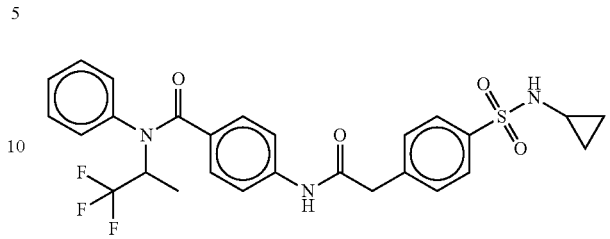

MS(ES⁺) m/z 546.2 (M+H)⁺.

149: 4-[2-(4-cyclopropylmethanesulfonylphenyl)acetamido]-N-(oxetan-3-yl)-N-phenylbenzamide

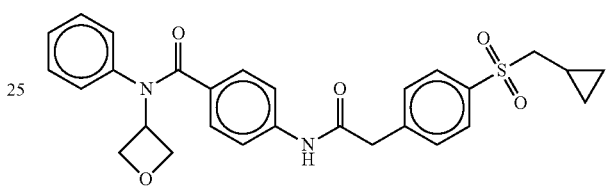

MS(ES⁺) m/z 505.2 (M+H)⁺.

150: N-(4-(7-oxa-4-azaspiro[2.5]octane-4-carbonyl)phenyl)-2-(4-((cyclopropylmethyl)sulfonyl)phenyl)acetamide

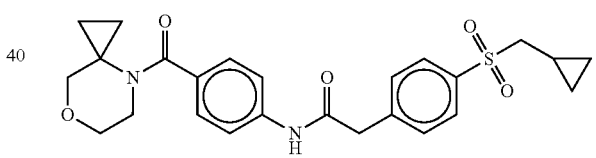

MS(ES⁺) m/z 469.2 (M+H)⁺.

151: N-(tert-butyl)-4-(2-(4-((cyclopropylmethyl)sulfonyl)phenyl)acetamido)-N-(2-hydroxyethyl)benzamide

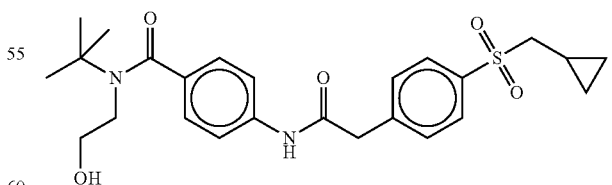

i) To a solution of 2-(tert-butylamino)ethan-1-ol (50 mg) and triethyl amine (66 μL) in CH₂Cl₂ (2 mL) was added tert-butylchlorodiphenylsilane (122 μL) and the reaction mixture was stirred overnight at room temperature. The reaction mixture was concentrated under reduced pressure and purified on SiO₂, using 0% to 2% methanol in dichloromethane, as the eluent, giving N-(2-((tert-butyldiphenyl-silyl)oxy)ethyl)-2-methylpropan-2-amine (135 mg).

ii) To a solution of the product obtained in the previous step (105 mg) and triethyl amine (79 μL) in CH₂Cl₂ (2 mL) was added a solution of 4-nitrobenzoyl chloride (50 mg) in CH₂Cl₂ (1 mL) and the reaction mixture was stirred overnight at room temperature. Water was added and the organic phase was separated. The aqueous phase was extracted with dichloromethane. The combined organic phases were filtered on a water repellent filter cartridge and concentrated under reduced pressure. The residue was purified on SiO₂, using 0% to 1% methanol in dichloromethane, as the eluent, giving N-(tert-butyl)-N-(2-((tert-butyldiphenylsilyl)oxy)ethyl)-4-nitrobenzamide (101 mg) as a white solid.

iii) To a solution of the product obtained in the previous step (100 mg) in ethanol (5 mL) were added water (0.5 mL), acetic acid (0.5 mL) and iron (33 mg) at room temperature and the reaction was stirred for 4 hours at 60° C. The reaction mixture was filtered. The filtrate was concentrated under reduced pressure, taken into dichloromethane, washed with water, brine, filtered on a water repellent filter cartridge and concentrated under reduced pressure giving 4-amino-N-(tert-butyl)-N-(2-((tert-butyldiphenylsilyl)oxy)ethyl)benzamide (100 mg).

iv) A solution of the product obtained in the previous step (103 mg), 2-(4-((cyclopropylmethyl)sulfonyl)phenyl)acetic acid (50 mg), EDCl (42 mg) and DMAP (4.8 mg) in CH₂Cl₂ (3 mL) was stirred overnight at room temperature. The organic layer was washed with water, brine, filtered on a water repellent filter cartridge and concentrated under reduced pressure. The residue was purified on SiO₂, using 0% to 4% methanol in dichloromethane, as the eluent, giving the title compound N-(tert-butyl)-N-(2-((tert-butyldiphenylsilyl)oxy)ethyl)-4-(2-(4-(cyclopropylmethyl)sulfonyl)phenyl)acetamido)benzamide (86 mg) as a white solid.

v) To a solution of the product obtained in the previous step (86 mg) in THF (3 mL) was added a 1M solution of tetrabutylammonium fluoride in THF (360 μL) and the reaction was stirred at room temperature overnight. The reaction mixture was quenched with water and extracted with dichloromethane. The organic phase was filtered on a water repellent filter cartridge, concentrated under reduced pressure and triturated with pentane/CH₂Cl₂ (10/1) giving the title compound N-(tert-butyl)-4-(2-(4-((cyclopropylmethyl)sulfonyl)phenyl)acetamido)-N-(2-hydroxyethyl)benzamide (22 mg) as a white solid. MS(ES⁺) m/z 473.2 (M+H)⁺.

Following a procedure analogous to that described for Example 151, using appropriate starting materials, the following compound has been prepared.

152: 4-(2-(4-((cyclopropylmethyl)sulfonyl)phenyl)acetamido)-N-(2-hydroxyethyl)-N-isobutylbenzamide

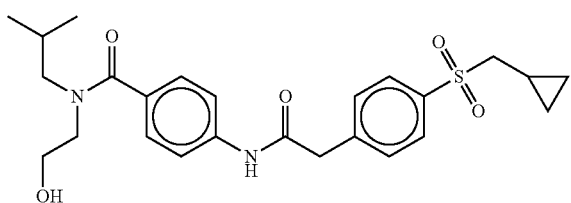

MS(ES⁺) m/z 473.2 (M+H)⁺.

153: 4-[2-(4-cyclopropylmethanesulfonylphenyl)acetamido]-N-(1-hydroxy-2-methylpropan-2-yl)-N-(4-methylphenyl)benzamide

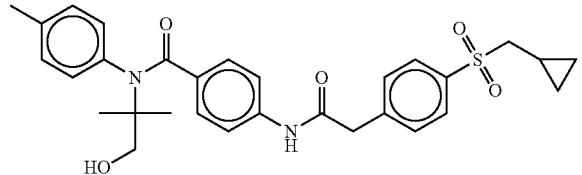

MS(ES⁺) m/z 535.2 (M+H)⁺.

154: 4-{2-[4-(cyclopropylsulfamoyl)phenyl]acetamido}-N-(1-hydroxy-2-methylpropan-2-yl)-N-(4-methylphenyl)benzamide

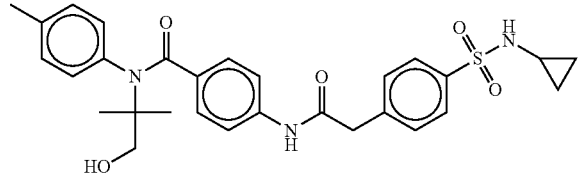

MS(ES⁺) m/z 536.2 (M+H)⁺.

155: 4-[2-(6-cyclopropylmethanesulfonylpyridin-3-yl)acetamido]-N-phenyl-N-(2,2,2-trifluoroethyl)benzamide

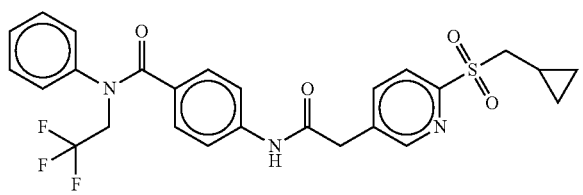

i) To a suspension of 2-bromo-5-methylpyridine (25 g) in water (200 ml) was added at room temperature an aqueous 8N HCl solution, after which thiourea (24.2) was added until the reaction mixture became a clear solution. The reaction mixture was stirred at reflux temperature for 48 hours during which more thiourea (18 g) was added portion wise, until complete conversion. The reaction mixture was cooled to 0° C. and quenched by the addition of an aqueous 4N NaOH solution (130 ml). The formed precipitate was dissolved in CH₂Cl₂ (220 mL) and the organic layer was washed with water. The aqueous layer was acidified to pH=3 and extracted with CH₂Cl₂ 3 times. The combined organic layers were dried over MgSO₄ and concentrated under vacuo. The residue was recrystallized from ethanol to give 5-methyl-pyridine-2-thiol (11.2 g) as a white solid.

ii) To a suspension of the product obtained in the previous step (2.3 g) and K₂CO₃ (600 mg) in acetonitrile (45 mL) was added at room temperature (bromomethyl)cyclopropane (10.4 mL). After stirring for 48 hours, the reaction mixture was filtered and the filtrate was concentrated under reduced pressure to give 2-[(cyclopropylmethyl)sulfanyl]-5-methyl-pyridine (17 g). The product was used in the next step without further purification.

iii) m-CPBA (38.1 g) was added to an ice cold solution of the product obtained in the previous step (17 g) in CH$_2$Cl$_2$ (250 mL). After stirring the reaction mixture over the weekend at room temperature, the reaction mixture was filtered and the filtrate was washed with a saturated aqueous NaHCO$_3$ solution, water and brine. The organic layer was dried on MgSO$_4$ and concentrated under reduced pressure to give 2-cyclopropylmethanesulfonyl-5-methylpyridine (17 g) as a white solid. The product was used in the next step without further purification.

iv) To a solution of the product obtained in the previous step (17 g) in acetonitrile (150 mL) were added NBS (15.8 g) and AIBN (660 mg). The reaction mixture was stirred for 17 hours at reflux temperature under a nitrogen atmosphere. After cooling, the reaction mixture was filtered and the filtrate was concentrated under reduced pressure. The crude product was purified on SiO$_2$, using 0% to 30% ethyl acetate in heptane as the eluent, to give 5-(bromomethyl)-2-cyclopropylmethanesulfonylpyridine (10.6 g).

v) The product obtained in the previous step (9 g) was added to a nitrogen purged solution of trimethylsilyl cyanide (3.1 g) and TBAF (31 mL) in acetonitrile (75 mL). The reaction mixture was stirred at 90° C. in a microwave reactor for 30 minutes. After cooling to room temperature the reaction mixture was diluted with a 3 to 1 mixture of CH$_2$Cl$_2$ and 2-propanol. The resulting mixture was washed with water, brine, dried on MgSO$_4$, filtered and the filtrate was concentrated under reduced pressure. The crude product was purified on SiO$_2$, using 0% to 80% ethyl acetate in heptane as the eluent to give 2-(6-cyclopropylmethanesulfonylpyridin-3-yl)acetonitrile (2.1 g) as a white solid.

vi) To a solution of the product obtained in the previous step (2.1 g) in ethanol (28 mL) was added a 2N aqueous NaOH solution (28 mL). The reaction mixture was stirred for 17 hours in a microwave reactor at 80° C. After cooling to room temperature, the reaction mixture was washed with CH$_2$Cl$_2$. The aqueous layer was acidified to pH=3 and extracted with ethyl acetate. The combined organic layers were washed with water, brine, dried on MgSO$_4$, filtered and concentrated under reduced pressure to give 2-(6-cyclopropylmethanesulfonylpyridin-3-yl)acetic acid (1.9 g) as the crude product. The product was used in the next step without further purification.

vii) Following a procedure analogous to that described for example 1, using the product obtained in the previous step and appropriate starting materials, the title compound 4-[2-(6-cyclopropylmethanesulfonylpyridin-3-yl)acetamido]-N-phenyl-N-(2,2,2-trifluoroethyl)benzamide (63 mg) has been prepared. MS(ES$^+$) m/z 532.2 (M+H)$^+$.

Following a procedure analogous to that described for example 155, the following compounds have been prepared.

156: 4-[2-(6-cyclopropylmethanesulfonylpyridin-3-yl)acetamido]-N-ethyl-2-fluoro-N-phenylbenzamide

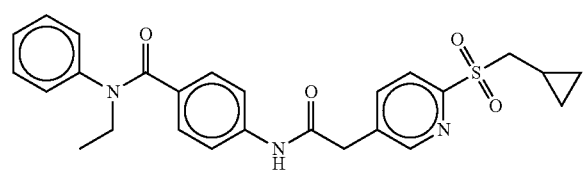

MS(ES$^+$) m/z 496.2 (M+H)$^+$.

157: 2-chloro-4-[2-(6-cyclopropylmethanesulfonylpyridin-3-yl)acetamido]-N-ethyl-N-phenylbenzamide

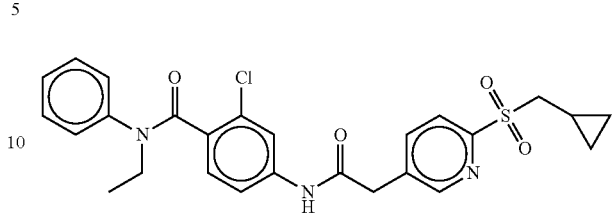

MS(ES$^+$) m/z 512.2 (M+H)$^+$.

158: N-tert-butyl-4-[2-(6-cyclopropylmethanesulfonylpyridin-3-yl)acetamido]-N-phenylbenzamide

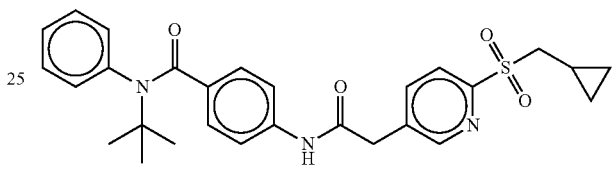

MS(ES$^+$) m/z 506.2 (M+H)$^+$.

159: N-tert-butyl-4-[2-(6-cyclopropylmethanesulfonylpyridin-3-yl)acetamido]-3-fluoro-N-phenylbenzamide

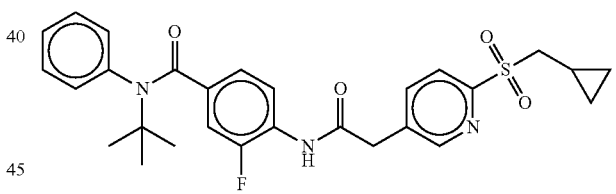

MS(ES$^+$) m/z 524.2 (M+H)$^+$.

160: 4-[2-(6-cyclopropylmethanesulfonylpyridin-3-yl)acetamido]-N-[2-(oxolan-2-yl)propan-2-yl]-N-phenylbenzamide

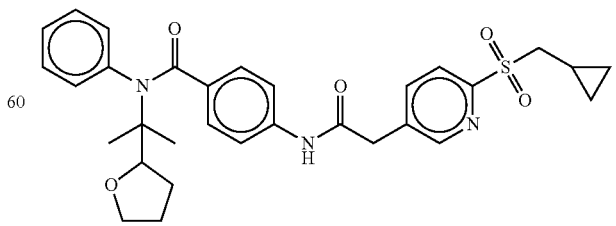

MS(ES$^+$) m/z 562.2 (M+H)$^+$.

161: 4-[2-(6-cyclopropylmethanesulfonylpyridin-3-yl)acetamido]-N-(1-hydroxy-2-methylpropan-2-yl)-N-(4-methylphenyl)benzamide

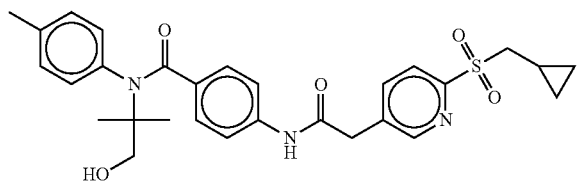

i) The title compound 4-[2-(6-cyclopropylmethanesulfonylpyridin-3-yl)acetamido]-N-(1-hydroxy-2-methylpropan-2-yl)-N-(4-methylphenyl)benzamide has been prepared following a procedure analogous to that described for example 151, using 2-(6-cyclopropylmethanesulfonylpyridin-3-yl) acetic acid (example 155. step vi) as the starting material. MS(ES$^+$) m/z 536.2 (M+H)$^+$.

162: 4-[2-(4-cyclopropylmethanesulfonylphenyl)acetamido]-N-ethyl-2-methyl-N-phenylbenzamide i) Following a procedure analogous to that described in Example 1, step iv), using 4-bromo-2-methylbenzoic acid (1.0 g) and N-ethylaniline (0.64 mL) as the starting materials, 4-bromo-N-ethyl-2-methyl-N-phenylbenzamide was synthesized (1.2 g).

ii) To a solution of the product obtained in the previous step (0.5 g) in NMP were added Cu$_2$O (11 mg) and an aqueous 35% NH$_4$OH solution (2 mL) and the mixture was stirred, for 8 hours, in a sealed tube at 80° C. in a microwave. The blue reaction mixture was poured into water and the product was extracted into ethyl acetate. The organic phase was washed with brine, dried on MgSO$_4$ and concentrated under reduced pressure giving 4-amino-N-ethyl-2-methyl-N-phenylbenzamide (0.4 g). The crude product was used without further purification in the next step.

iii) Following a procedure analogous to that described in Example 1, step iv), the product obtained in the previous step (54 mg) was converted to the title compound 4-[2-(4-cyclopropylmethanesulfonylphenyl)acetamido]-N-ethyl-2-methyl-N-phenylbenzamide (60 mg). MS(ES$^+$) m/z 491.2 (M+H)$^+$.

Following a procedure analogous to that described for Example 162, using appropriate starting materials, the following compounds have been prepared.

163: 4-[2-(4-cyclopropylmethanesulfonylphenyl)acetamido]-N,2-dimethyl-N-(2-methylphenyl)benzamide

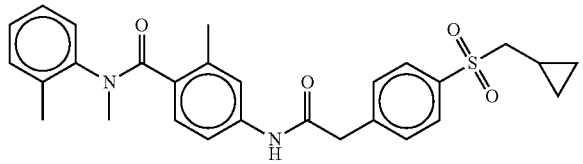

MS(ES$^+$) m/z 491.2 (M+H)$^+$.

164: 4-[2-(4-cyclopropylmethanesulfonylphenyl)acetamido]-N-(2,3-dimethylphenyl)-N-ethyl-2-methylbenzamide

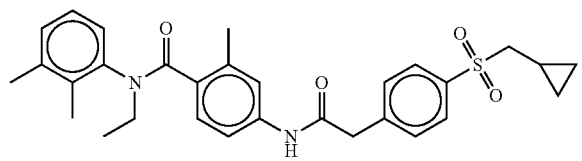

MS(ES$^+$) m/z 519.3 (M+H)$^+$.

165: 4-[2-(4-cyclopropylmethanesulfonylphenyl)acetamido]-N-(2-fluorophenyl)-N,2-dimethylbenzamide

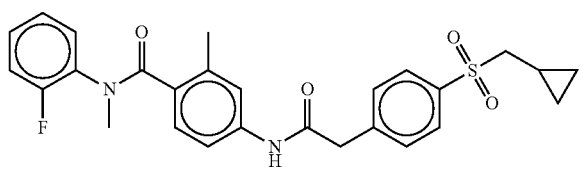

MS(ES$^+$) m/z 495.3 (M+H)$^+$.

166: N-(2-chlorophenyl)-4-[2-(4-cyclopropylmethanesulfonylphenyl)acetamido]-N-ethyl-2-methylbenzamide

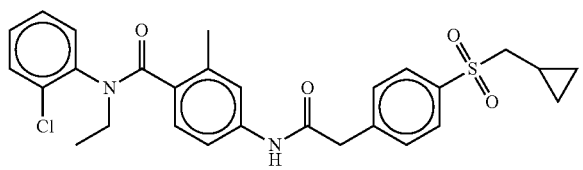

MS(ES$^+$) m/z 525.3 (M+H)$^+$.

Example 167

RORγ GAL4 Reporter Gene Assay

Example inhibitors 1-166 were tested for their ability to inhibit RORγ activity in a RORγ GAL4 reporter gene assay. The assay procedure and results are described below.

RORγ GAL4 Reporter Gene Assay Description

A GAL4 one-hybrid reporter system employing luciferase readout was established to determine inhibition of RORγ in 293FT cells. The RORγ ligand-binding domain (LBD) was fused to the yeast GAL4 DNA binding domain (DBD) and placed under the control of the human cytomegalovirus (CMV) immediate early promoter, using expression vector pFN26A (Promega) and standard recombinant DNA cloning methods. To serve as a control in the assay, a similar vector was generated in which the GAL4-DBD was fused to Herpes simplex virus protein 16 (VP16), a constitutive transcriptional activator.

To monitor the inhibitory effect of compounds on RORγ, a transcriptional reporter construct was used. The pGL4.35 vector (Promega) contains nine copies of the GAL4 Upstream Activator Sequence (UAS). This sequence drives the transcription of the luciferase reporter gene luc2P in response to binding of a fusion protein containing the GAL4 DNA binding domain, as for example expressed by the GAL4-RORγ-LBD and GAL4-VP16 expression vectors described above. To allow a GAL4 fusion protein to drive the expression of the luciferase reporter, the pGL4.35 expression vector and the appropriate GAL4 fusion protein expression vector were bulk transfected in the 293FT cells using standard transfection techniques.

The day after transfection, cells were plated into 96 well plates, test compound was added and the plates were incubated overnight. Subsequently, the firefly luciferase activity was quantified using luciferase detection reagent and luminescence readout.

Detailed Assay Description

293FT cells (Invitrogen) were transfected with a GAL4 fusion protein expression vector (as described above) and the transcriptional reporter construct (pGL4.35, Promega). 60 µL of TransIT-293 transfection reagent (Mirus Bio) was added drop wise to 1500 µl Opti-MEM I Reduced Serum Medium (Invitrogen) and incubated at room temperature (RT) for 5 to 20 minutes. 1500 µL of this reagent mixture was added to 5 µg of GAL4 fusion protein expression vector and 5 µg of the transcriptional reporter construct, and incubated at RT for 20 minutes.

To harvest 293FT cells from a T75 flask, first the culture medium was taken off the cells. Subsequently, the cells were washed with Phosphate Buffered Saline (PBS) (Lonza), after which the PBS was removed. To dissociate the cells, 1 ml of TrypLE Express (Invitrogen) was added to the flask, followed by incubation at RT until the cells visually started to detach. Cells were collected in 5 mL of assay medium (DMEM culture medium (Lonza), 10% dialyzed FBS (Invitrogen) and Pen/Strep (Lonza)) to achieve a single cell suspension. $10 \times 10^6$ cells were spun down and re-suspended in 10 mL of assay medium. Subsequently, the cell suspension was added to the transfection mix tube, and then transferred as a whole to a T75 flask (Greiner), followed by overnight (16-24 hours) incubation at 37° C. and 5% $CO_2$.

For compound screening, the cells were harvested (as described above) and counted. $13 \times 10^6$ cells were spun down, the supernatant was aspirated and the cells were re-suspended in 17.3 mL of assay medium obtaining a cell suspension of $0.75 \times 10^6$ cells/mL. 80 µL of cell suspension (60,000 cells) was plated per well into a white, flat bottom, tissue culture treated, 96 well screening plates (Greiner).

Test compounds were diluted, starting from a 10 mM dimethylsulfoxide (DMSO) stock solution, to serial dilutions in DMSO at 500× the final test concentration. Subsequently, these solutions were diluted to 5× the final test concentration in two 10-fold-dilution steps in assay medium.

The final DMSO concentration of the 5× test compound solution was 1%. 20 µL of the 5× test compound solution was added to each test well of the 96 well plate previously plated with 80 µl cell suspension, resulting in the final test concentration with 0.2% DMSO.

The plates were incubated overnight (16-24 hours) at 37° C. and 5% $CO_2$.

For the luciferase readout, the luciferase reagent (Britelite Plus, Perkin Elmer) was brought to RT. To each test well of the screening plates, 100 µL of 2.5-fold diluted Britelite Plus reagent was added, followed by incubation at RT for 10 minutes. The luciferase luminescence signal was measured using a Wallac Victor Microplate Reader (Perkin Elmer).

The half maximum inhibitory concentration (1050) values for the test compounds were calculated from the luciferase signal using GraphPad Prism software (GraphPad Software).

All exemplified compounds of Formula I (Examples 1-166) were found to have mean $pIC_{50}$ values above 5.

Examples 1-3, 5-76, 79, 81-97, 99-149 and 153-166 were found to have mean $pIC_{50}$ values above or equal to 6.

Examples 3, 5, 6, 9, 10, 12, 14-22, 24, 27, 29-32, 35, 37, 40, 42-49, 51-53, 55-59, 61, 63, 64, 66, 71, 74, 75, 81-84, 86-90, 92-96, 99, 100, 102-105, 107-109, 113, 115-146, 148, 149 and 153-166 were found to have mean $pIC_{50}$ values above or equal to 7.

Examples 3, 16, 19-21, 29, 31, 32, 37, 40, 43, 45, 46, 49, 63, 64, 81, 83, 86-90, 92-94, 99, 102-104, 109, 113, 117-119, 122-131, 134, 139, 140-142, 144-146, 149, 155, 158, 159, 163, 164 and 166 were found to have mean $pIC_{50}$ values above or equal to 8.

Example 168

Peripheral Blood Mononuclear Cell (PBMC) IL-17 Assay

Example inhibitors 3, 6, 9, 16, 17, 19, 20, 31, 35, 40, 45, 64, 71, 81, 86-89, 94, 103, 104, 115, 121, 130, 131, 133, 135, 137, 140, 144-146, 153, 155 and 158-160 were tested for their ability to inhibit the IL-17A production in anti-CD3/anti-CD28 stimulated peripheral blood mononuclear cells (PBMCs) isolated from human blood. The assay procedure and results are described below.

PBMC IL-17 Assay Description

This assay is designed to measure the levels of IL-17A secreted from anti-CD3/anti-CD28 stimulated PBMCs with the aim of measuring RORγ mediated inhibition of IL-17A production.

The assay medium consists of 90% RPMI 1640 (Lonza), 10% heat inactivated fetal bovin serum (FBS, Lonza) and 100 U/mL penicillin/streptomycin solution.

Assay Description

Anti-CD3 antibody (BD Pharmingen) was diluted to 10 µg/ml in PBS (Lonza). 30 µL of 10 µg/ml anti-CD3 solution was added to the inner 60 wells, excluding any negative control wells, of a 96-well cell culture treated U-bottom plate (Greiner). Plates were incubated overnight (16-24 hours) at 37° C. and 5% $CO_2$.

Peripheral blood mononuclear cells were separated from buffy coats (Sanquin) using Ficoll-Paque PREMIUM separation medium (GE Healthcare Life Sciences) according to manufacturer's protocol and re-suspended in assay medium at 37° C.

Test compounds were diluted, starting from a 10 mM dimethylsulfoxide (DMSO) stock solution, to serial dilutions in DMSO at 200× the final test concentration. Subsequently, these solutions were diluted in two dilution steps in assay medium to 10× the final test concentration. The DMSO concentration of the 10× test compound solution was 5%.

Anti-CD28 antibody (BD Pharmingen) was diluted to 20 µg/mL in PBS. The PBMCs were diluted to a concentration of $2.5 \times 10^6$ cells/mL in assay medium at 37° C.

For compound screening, the anti-CD3 coated plates were washed three times with PBS, the wells were subsequently aspirated using vacuum. To each screening well 80 µL of the PBMC suspension, 10 µL of the anti-CD28 solution and 10 µL of the 10× test compound solution was added, resulting in the final test concentration with 0.5% DMSO. All outer wells were filled with assay medium to prevent evaporation. Plates were incubated for 5 days at 37° C. and 5% $CO_2$.

After incubation the plates were spun down at 1500 rpm for 4 minutes and the supernatant was collected. Subsequently, the IL-17A levels in the supernatants was determined using an IL-17 ELISA kit (human IL-17 DuoSet, R&D systems) according to manufacturer's protocol.

The half maximum inhibitory concentration (1050) values for the test compounds were calculated from the IL-17A signal using GraphPad Prism software (GraphPad Software).

The tested examples 3, 6, 9, 16, 17, 19, 20, 31, 35, 40, 45, 64, 71, 81, 86-89, 94, 103, 104, 115, 121, 130, 131, 133, 135, 137, 140, 144-146, 153, 155 and 158-160 were found to have mean $pIC_{50}$ values above or equal to 6.

Examples 3, 16, 17, 19, 20, 31, 35, 40, 64, 81, 86-89, 94, 104, 115, 121, 130, 131, 133, 135, 137, 140, 144-146, 153, 155 and 158-160 were found to have mean $pIC_{50}$ values above or equal to 7.

Examples 3, 16, 19, 20, 31, 64, 81, 86-89, 94, 104, 115, 130, 133, 140, 144-146, 155 and 158 were found to have mean $pIC_{50}$ values above or equal to 8.

The invention claimed is:

1. A compound according to Formula I

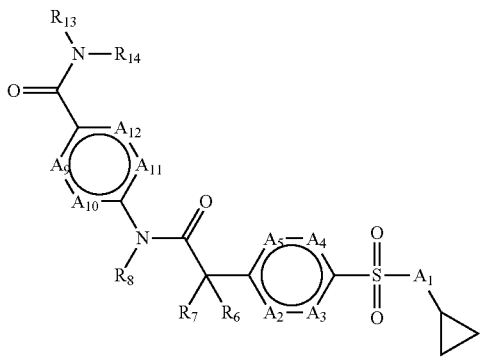

(Formula I)

or a pharmaceutically acceptable salt thereof wherein
$A_1$ is $NR_1$ or $CR_1$, with $R_1$ being H or methyl, with methyl, if present, optionally being substituted with one or more F;
the cyclopropyl moiety can be optionally substituted with one or more methyl and one or more F;
$A_2$-$A_5$ are N or $CR_2$-$CR_5$, respectively, with the proviso that no more than two of the four positions A in $A_2$-$A_5$ can be simultaneously N;
$R_2$-$R_5$ are independently H, halogen, amino, C(1-3)alkoxy, (di)C(1-3)alkylamino or C(1-6)alkyl;
$R_6$ and $R_7$ are independently H, F, methyl, ethyl, hydroxyl or methoxy or $R_6$ and $R_7$ together is carbonyl, all alkyl groups, if present, optionally being substituted with one or more F;
$R_8$ is H or C(1-6)alkyl;
$A_9$-$A_{12}$ are N or $CR_9$-$CR_{12}$, respectively, with the proviso that no more than two of the four positions A in $A_9$-$A_{12}$ can be simultaneously N;
$R_9$-$R_{12}$ are independently H, halogen, amino, C(1-3)alkoxy, (di)C(1-3)alkylamino or C(1-6)alkyl;
$R_{13}$ is H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, amino, hydroxyl, cyano, C(1-3)alkoxy, C(1-3)alkoxycarbonyl, (di)C(1-3)alkylamino or C(1-3)alkyl; and
$R_{14}$ is H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, amino, hydroxyl, cyano, C(1-3)alkoxy, C(1-3)alkoxycarbonyl, (di)C(1-3)alkylamino or C(1-3)alkyl;
or $R_{13}$ and $R_{14}$ are fused and form a ring having 5 to 7 atoms by joining $R_{13}$ being C(1-6)alkyl or C(2-6)alkenyl with an independent substituent within the definition of $R_{14}$, all groups optionally substituted with one or more halogen, amino, hydroxy, cyano, C(1-3)alkoxy, C(1-3)alkoxycarbonyl, (di)C(1-3)alkylamino or C(1-3)alkyl.

2. The compound according to claim 1 where $A_1$ is $CR_1$ and $R_1$ is hydrogen.

3. The compound according to claim 1 where $A_1$ is $NR_1$ and $R_1$ is hydrogen.

4. The compound according to claim 1 wherein all of the positions A in $A_2$-$A_5$ are carbon and all of the position R in $R_2$-$R_5$ are H.

5. The compound according to claim 1 where $R_6$ and $R_7$ are independently H, methyl or hydroxyl.

6. The compound according to claim 1 where $R_8$ is H.

7. The compound according to claim 1 wherein all positions A of $A_9$-$A_{12}$ are carbon or wherein position A in either $A_9$ or $A_{10}$ is nitrogen and the remaining positions A in $A_9$-$A_{12}$ are carbon.

8. The compound according to claim 1 wherein $R_9$-$R_{12}$ are independently H, halogen, methyl or methoxy.

9. The compound according to claim 1 wherein $R_{13}$ and $R_{14}$ are independently H, C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6-10)aryl, C(6-10)arylC(1-4)alkyl, C(1-9)heteroaryl or C(1-9)heteroarylC(1-4)alkyl, all groups optionally substituted with one or more halogen, hydroxyl, cyano, C(1-3)alkoxy, C(1-3)alkoxycarbonyl or C(1-3)alkyl.

10. The compound according to claim 1 wherein $R_{13}$ and $R_{14}$ are fused and form a ring consisting of 5 to 7 atoms by joining C(1-6)alkyl or C(2-6)alkenyl at $R_{13}$ with a substituent at $R_{14}$ selected from C(1-6)alkyl, C(2-6)alkenyl, C(3-6)cycloalkyl, C(3-6)cycloalkylC(1-4)alkyl, C(2-5)heterocycloalkyl, C(2-5)heterocycloalkyl-C(1-4)alkyl, C(6)aryl, C(6)arylC(1-4)alkyl, C(1-5)heteroaryl or C(1-5)heteroarylC(1-4)alkyl, with all groups optionally substituted with one or more halogen, hydroxy, cyano, C(1-3)alkoxy, C(1-3)alkoxycarbonyl, or C(1-3)alkyl.

11. A compound or a pharmaceutically acceptable salt thereof, wherein the compound is selected from the group consisting of:

4-[2-(4-cyclopropylmethanesulfonylphenyl)acetamido]-N-propylbenzamide;
4-[2-(4-cyclopropylmethanesulfonylphenyl)acetamido]-N-ethylbenzamide;
4-[2-(4-cyclopropylmethanesulfonylphenyl)acetamido]-N-methyl-N-phenylbenzamide;
4-[2-(4-cyclopropylmethanesulfonylphenyl)acetamido]-N,N-dimethylbenzamide;
N-benzyl-4-[2-(4-cyclopropylmethanesulfonylphenyl)acetamido]-N-methylbenzamide;
4-[2-(4-cyclopropylmethanesulfonylphenyl)acetamido]-N-(2-phenylpropan-2-yl)benzamide;
4-[2-(4-cyclopropylmethanesulfonylphenyl)acetamido]-N-methyl-N-propylbenzamide;
4-[2-(4-cyclopropylmethanesulfonylphenyl)acetamido]-N-methyl-N-(2-methylpropyl)benzamide;
4-[2-(4-cyclopropylmethanesulfonylphenyl)acetamido]-N-(cyclopropylmethyl)-N-propylbenzamide;
4-[2-(4-cyclopropylmethanesulfonylphenyl)acetamido]-N-methyl-N-(2-phenylethyl)benzamide;
N-tert-butyl-4-[2-(4-cyclopropylmethanesulfonylphenyl)acetamido]benzamide;
N,N-dibenzyl-4-[2-(4-cyclopropylmethanesulfonylphenyl)acetamido]benzamide;
N-benzyl-4-[2-(4-cyclopropylmethanesulfonylphenyl)acetamido]benzamide;
4-[2-(4-cyclopropylmethanesulfonylphenyl)acetamido]-N-(1-phenylethyl)benzamide;
4-[2-(4-cyclopropylmethanesulfonylphenyl)acetamido]-N,N-bis(2-methylpropyl)benzamide;
4-[2-(4-cyclopropylmethanesulfonylphenyl)acetamido]-N-ethyl-N-phenylbenzamide;
4-[2-(4-cyclopropylmethanesulfonylphenyl)acetamido]-N-methyl-N-(pyridin-2-yl)benzamide;
4-[2-(4-cyclopropylmethanesulfonylphenyl)acetamido]-N-methyl-N-[(1S)-1-phenylethyl]benzamide;
4-[2-(4-cyclopropylmethanesulfonylphenyl)acetamido]-N-phenyl-N-propylbenzamide;
4-[2-(4-cyclopropylmethanesulfonylphenyl)acetamido]-N-propyl-N-(pyridin-3-yl)benzamide;
N-benzyl-4-[2-(4-cyclopropylmethanesulfonylphenyl)acetamido]-N-propylbenzamide;
4-{2-[4-(cyclopropylsulfamoyl)phenyl]acetamido}-N-phenyl-N-propylbenzamide;
N-benzyl-4-{2-[4-(cyclopropylsulfamoyl)phenyl]acetamido}-N-propylbenzamide;
N,N-dibenzyl-4-{2-[4-(cyclopropylsulfamoyl)phenyl]acetamido}benzamide;
ethyl 1-{4-[2-(4-cyclopropylmethanesulfonylphenyl)acetamido]benzoyl}piperidine-3-carboxylate;
N-tert-butyl-4-[2-(4-cyclopropylmethanesulfonylphenyl)acetamido]-N-methylbenzamide;
N,N-dicyclobutyl-4-[2-(4-cyclopropylmethanesulfonylphenyl)acetamido]benzamide;
2-(4-cyclopropylmethanesulfonylphenyl)-N-[4-(2-methylpiperidine-1-carbonyl)phenyl]acetamide;
4-[2-(4-cyclopropylmethanesulfonylphenyl)acetamido]-N-ethyl-N-(4-methylphenyl)benzamide;
methyl 3-{N-ethyl-4-[2-(4-cyclopropylmethanesulfonylphenyl)acetamido]benzamido}benzoate;
4-[2-(4-cyclopropylmethanesulfonylphenyl)acetamido]-N-ethyl-N-(3-methylphenyl)benzamide;
ethyl 2-(N-benzyl-1-{4-[2-(4-cyclopropylmethanesulfonylphenyl)acetamido]phenyl}formamido)acetate;
ethyl 6-{4-[2-(4-cyclopropylmethanesulfonylphenyl)acetamido]benzoyl}-4H,5H,6H,7H-thieno[2,3-c]pyridine-2-carboxylate;
N-cyclohexyl-4-[2-(4-cyclopropylmethanesulfonylphenyl)acetamido]-N-methylbenzamide;
2-(4-cyclopropylmethanesulfonylphenyl)-N-[4-(2-phenylpyrrolidine-1-carbonyl)phenyl]acetamide;
2-(4-cyclopropylmethanesulfonylphenyl)-N-[4-(piperidine-1-carbonyl)phenyl]acetamide;
4-[2-(4-cyclopropylmethanesulfonylphenyl)acetamido]-N-(2-methylpropyl)-N-phenylbenzamide;
ethyl 2-(1-{4-[2-(4-cyclopropylmethanesulfonylphenyl)acetamido]benzoyl}pyrrolidin-2-yl)-1,3-thiazole-4-carboxylate;
2-(4-cyclopropylmethanesulfonylphenyl)-N-{4-[2-(morpholin-4-ylmethyl)piperidine-1-carbonyl]phenyl}acetamide;
2-(4-cyclopropylmethanesulfonylphenyl)-N-[4-(1,2,3,4-tetrahydroquinoline-1-carbonyl)phenyl]acetamide;
2-(4-cyclopropylmethanesulfonylphenyl)-N-[4-(2,3-dihydro-1H-indole-1-carbonyl)phenyl]acetamide;
N-benzyl-4-[2-(4-cyclopropylmethanesulfonylphenyl)acetamido]-N-ethylbenzamide;
4-{2-[4-(cyclopropylsulfamoyl)phenyl]acetamido}-N-ethyl-N-phenylbenzamide;
4-{2-[4-(cyclopropylsulfamoyl)phenyl]acetamido}-N-methyl-N-phenylbenzamide;
4-{2-[4-(cyclopropylsulfamoyl)phenyl]acetamido}-N-ethyl-N-(4-methylphenyl)benzamide;
4-{2-[4-(cyclopropylsulfamoyl)phenyl]acetamido}-N-ethyl-N-(3-methylphenyl)benzamide;
methyl 3-(N-ethyl-4-{2-[4-(cyclopropylsulfamoyl)phenyl]acetamido}benzamido)benzoate;
2-(4-cyclopropylmethanesulfonylphenyl)-N-[4-(3-phenylpiperidine-1-carbonyl)phenyl]acetamide;
2-(4-cyclopropylmethanesulfonylphenyl)-N-[4-(2-phenylpiperidine-1-carbonyl)phenyl]acetamide;
4-{2-[4-(cyclopropylsulfamoyl)phenyl]acetamido}-N-ethyl-N-(pyridin-3-yl)benzamide;
6-[2-(4-cyclopropylmethanesulfonylphenyl)acetamido]-N-ethyl-N-phenylpyridine-3-carboxamide;
4-[2-(4-cyclopropylmethanesulfonylphenyl)acetamido]-N-ethyl-N-(pyridin-3-yl)benzamide;
3-chloro-4-[2-(4-cyclopropylmethanesulfonylphenyl)acetamido]-N-ethyl-N-phenylbenzamide;
6-{2-[4-(cyclopropylsulfamoyl)phenyl]acetamido}-N-ethyl-N-phenylpyridine-3-carboxamide;
2-(4-cyclopropylmethanesulfonylphenyl)-N-[4-(1,2,3,4-tetrahydroisoquinoline-2-carbonyl)phenyl]acetamide;
4-[2-(4-cyclopropylmethanesulfonylphenyl)acetamido]-N-ethyl-N-[(5-methyl-1,2-oxazol-3-yl)methyl]benzamide;
2-(4-cyclopropylmethanesulfonylphenyl)-N-[4-(4-methyl-2-phenylpiperazine-1-carbonyl)phenyl]acetamide;
4-[2-(4-cyclopropylmethanesulfonylphenyl)acetamido]-N-ethyl-2-methoxy-N-phenylbenzamide;
4-[2-(4-cyclopropylmethanesulfonylphenyl)acetamido]-N-(furan-2-ylmethyl)-N-methylbenzamide;
4-[2-(4-cyclopropylmethanesulfonylphenyl)acetamido]-N-[2-methyl-1-(morpholin-4-yl)propan-2-yl]benzamide;
4-[2-(4-cyclopropylmethanesulfonylphenyl)acetamido]-N,N-bis(prop-2-en-1-yl)benzamide;
4-{2-[4-(cyclopropylsulfamoyl)phenyl]acetamido}-N,N-bis(2-methylpropyl)benzamide;

2-(4-cyclopropylmethanesulfonylphenyl)-N-[4-(2,3,4,5-tetrahydro-1H-1-benzazepine-1-carbonyl)phenyl]acetamide;
4-[2-(4-cyclopropylmethanesulfonylphenyl)acetamido]-N-(4-methyl-5-methyl-1,3-thiazol-2-yl)-N-ethylbenzamide;
4-{2-[4-(cyclopropylsulfamoyl)phenyl]acetamido}-N-propyl-N-(pyridin-3-yl)benzamide;
2-[4-(cyclopropylsulfamoyl)phenyl]-N-[4-(2-phenylpiperidine-1-carbonyl)phenyl]acetamide;
2-chloro-4-[2-(4-cyclopropylmethanesulfonylphenyl)acetamido]-N-methyl-N-(pyridin-2-yl)benzamide;
4-[2-(4-cyclopropylmethanesulfonylphenyl)acetamido]-N-[2-(pyridin-3-yl)propan-2-yl]benzamide;
4-[2-(4-cyclopropylmethanesulfonylphenyl)acetamido]-N-[(2R)-1,1,1-trifluoro-3-methylbutan-2-yl]benzamide;
4-[2-(4-cyclopropylmethanesulfonylphenyl)acetamido]-N-[(1S)-1-(2-methoxyphenyl)ethyl]benzamide;
4-[2-(4-cyclopropylmethanesulfonylphenyl)acetamido]-N-[(1S)-1-(2-fluorophenyl)ethyl]benzamide;
N-[cyano(thiophen-2-yl)methyl]-4-[2-(4-cyclopropylmethanesulfonylphenyl) acetamido]benzamide;
N-[cyano(phenyl)methyl]-4-[2-(4-cyclopropylmethanesulfonylphenyl) acetamido]benzamide;
4-[2-(4-cyclopropylmethanesulfonylphenyl)acetamido]-N-[2-(trifluoromethoxy)phenyl]benzamide;
4-[2-(4-cyclopropylmethanesulfonylphenyl)acetamido]-N-(2,6-dimethylphenyl)benzamide;
N-[(1R)-1-(4-chlorophenyl)-2,2,2-trifluoroethyl]-4-[2-(4-cyclopropylmethanesulfonylphenyl)acetamido]benzamide;
N-cyclopropyl-4-[[2-[4-(cyclopropylmethylsulfonyl)phenyl]acetyl]amino]-N-(2-hydroxyethyl)benzamide;
N-cyclopropyl-4-[[2-[4-(cyclopropylmethylsulfonyl)phenyl]acetyl]amino]-N-[(1-hydroxycyclobutyl)methyl]benzamide;
N-cyclopropyl-4-[[2-[4-(cyclopropylmethylsulfonyl)phenyl]acetyl]amino]-N-(2-methoxyethyl)benzamide;
N-cyclopropyl-4-[[2-[4-(cyclopropylmethylsulfonyl)phenyl]acetyl]amino]-N-tetrahydropyran-4-yl-benzamide;
4-[2-(4-cyclopropylmethanesulfonylphenyl)acetamido]-N-propyl-N-(thiophen-3-yl)benzamide;
N-butyl-4-[2-(4-cyclopropylmethanesulfonylphenyl)acetamido]-N-(1,3-thiazol-2-yl)benzamide;
4-[2-(4-cyclopropylmethanesulfonylphenyl)acetamido]-N-propyl-N-(1,3-thiazol-2-yl)benzamide;
4-[2-(4-cyclopropylmethanesulfonylphenyl)acetamido]-N-ethyl-N-(1,3-thiazol-2-yl)benzamide;
4-[2-(4-cyclopropylmethanesulfonylphenyl)acetamido]-N-methyl-N-(1,3-thiazol-2-yl)benzamide;
4-[2-(4-cyclopropylmethanesulfonylphenyl)acetamido]-N-(1,3-dimethyl-1H-pyrazol-5-yl)-N-propylbenzamide;
4-[2-(4-cyclopropylmethanesulfonylphenyl)acetamido]-N-(5-methyl-1,2-oxazol-3-yl)-N-propylbenzamide;
4-[2-(4-cyclopropylmethanesulfonylphenyl)acetamido]-N-(1,3-dimethyl-1H-pyrazol-5-yl)-N-ethylbenzamide;
4-[2-(4-cyclopropylmethanesulfonylphenyl)acetamido]-N-ethyl-N-(5-methyl-1,2-oxazol-3-yl)benzamide;
4-[2-(4-cyclopropylmethanesulfonylphenyl)acetamido]-N-methyl-N-(5-methyl-1,2-oxazol-3-yl)benzamide;
4-{2-[4-(cyclopropylsulfamoyl)phenyl]acetamido}-N-methyl-N-(5-methyl-1,2-oxazol-3-yl)benzamide;
4-{2-[4-(cyclopropylsulfamoyl)phenyl]acetamido}-N-(1,3-dimethyl-1H-pyrazol-5-yl)-N-propylbenzamide;
4-{2-[4-(cyclopropylsulfamoyl)phenyl]acetamido}-N-(5-methyl-1,2-oxazol-3-yl)-N-propylbenzamide;
4-[2-(4-cyclopropylmethanesulfonylphenyl)acetamido]-N-ethyl-N-(3-methyl-1,2-oxazol-5-yl)benzamide;
4-{2-[4-(cyclopropylsulfamoyl)phenyl]acetamido}-N-ethyl-N-(3-methyl-1,2-oxazol-5-yl)benzamide;
4-[2-(4-cyclopropylmethanesulfonylphenyl)acetamido]-N-ethyl-N-(5-methyl-1,3,4-thiadiazol-2-yl)benzamide;
4-{2-[4-(cyclopropylsulfamoyl)phenyl]acetamido}-N-ethyl-N-(5-methyl-1,3,4-thiadiazol-2-yl)benzamide;
4-{2-[4-(cyclopropylsulfamoyl)phenyl]acetamido}-N-ethyl-3-methoxy-N-phenylbenzamide;
4-[2-(4-cyclopropylmethanesulfonylphenyl)acetamido]-N-ethyl-2-fluoro-N-phenylbenzamide;
2-chloro-4-[2-(4-cyclopropylmethanesulfonylphenyl)acetamido]-N-ethyl-N-phenylbenzamide;
4-[2-(4-cyclopropylmethanesulfonylphenyl)acetamido]-N-ethyl-3-methoxy-N-phenylbenzamide;
4-[2-(4-cyclopropylmethanesulfonylphenyl)acetamido]-N-ethyl-3-fluoro-N-phenylbenzamide;
4-[2-(4-cyclopropylmethanesulfonylphenyl)acetamido]-N-ethyl-N-(1,2-oxazol-3-yl)benzamide;
4-[2-(4-cyclopropylmethanesulfonylphenyl)acetamido]-N-phenyl-N-(2,2,2-trifluoroethyl)benzamide;
4-[2-(4-cyclopropylmethanesulfonylphenyl)acetamido]-N-ethyl-3-methyl-N-phenylbenzamide;
4-{2-[4-(cyclopropylsulfamoyl)phenyl]acetamido}-N-ethyl-3-methyl-N-phenylbenzamide;
4-{2-[4-(cyclopropylsulfamoyl)phenyl]acetamido}-N-(4-methyl-5-methyl-1,3-thiazol-2-yl)-N-ethyl-benzamide;
4-[2-(4-cyclopropylmethanesulfonylphenyl)acetamido]-N-(dimethyl-1,2-oxazol-4-yl)-N-ethyl-benzamide;
4-{2-[4-(cyclopropylsulfamoyl)phenyl]acetamido}-N-phenyl-N-(2,2,2-trifluoroethyl)benzamide;
4-{2-[4-(cyclopropylsulfamoyl)phenyl]acetamido}-N-(dimethyl-1,2-oxazol-4-yl)-N-ethylbenzamide;
4-{2-[4-(cyclopropylsulfamoyl)phenyl]acetamido}-N-ethyl-2-fluoro-N-phenylbenzamide;
2-chloro-4-{2-[4-(cyclopropylsulfamoyl)phenyl]acetamido}-N-ethyl-N-phenylbenzamide;
N-benzyl-N-tert-butyl-4-[2-(4-cyclopropylmethanesulfonylphenyl) acetamido]benzamide;
4-[2-(4-cyclopropylmethanesulfonylphenyl)acetamido]-N-(1-methylpiperidin-4-yl)-N-phenylbenzamide;
N-(4-bromophenyl)-4-[2-(4-cyclopropylmethanesulfonylphenyl)acetamido]-N-phenylbenzamide;
4-[2-(4-cyclopropylmethanesulfonylphenyl)acetamido]-2-fluoro-N-methyl-N-(2-methylphenyl)benzamide;
2-chloro-4-[2-(4-cyclopropylmethanesulfonylphenyl)acetamido]-N-methyl-N-(2-methylphenyl)benzamide;
N-(2-chlorophenyl)-4-[2-(4-cyclopropylmethanesulfonylphenyl)acetamido]-N-ethyl-2-fluorobenzamide;
4-[2-(4-cyclopropylmethanesulfonylphenyl)acetamido]-N-(2,3-dimethylphenyl)-N-ethyl-2-fluorobenzamide;
2-chloro-4-[2-(4-cyclopropylmethanesulfonylphenyl)acetamido]-N-(2,3-dimethylphenyl)-N-ethylbenzamide;
N-[4-(3-tert-butyl-3,4-dihydro-2H-1,4-benzoxazine-4-carbonyl)phenyl]-2-(4-cyclopropylmethanesulfonylphenyl)acetamide;
4-[2-(4-cyclopropylmethanesulfonylphenyl)acetamido]-N-(2-methoxyphenyl)-N,2-dimethylbenzamide;
2-chloro-4-[2-(4-cyclopropylmethanesulfonylphenyl)acetamido]-N-phenyl-N-(2,2,2-trifluoroethyl)benzamide;
4-[2-(4-cyclopropylmethanesulfonylphenyl)acetamido]-2-fluoro-N-(2-methoxyphenyl)-N-methylbenzamide;
2-chloro-4-[2-(4-cyclopropylmethanesulfonylphenyl)acetamido]-N-(2-methoxyphenyl)-N-methylbenzamide;

4-[2-(4-cyclopropylmethanesulfonylphenyl)acetamido]-2-fluoro-N-(2-fluorophenyl)-N-methylbenzamide;

2-chloro-4-[2-(4-cyclopropylmethanesulfonylphenyl)acetamido]-N-(2-fluorophenyl)-N-methylbenzamide;

2-chloro-N-(2-chlorophenyl)-4-[2-(4-cyclopropylmethanesulfonylphenyl) acetamido]-N-ethylbenzamide;

2-chloro-4-[2-(4-cyclopropylmethanesulfonylphenyl)acetamido]-N-ethyl-N-(2-methylphenyl)benzamide;

N-tert-butyl-4-[2-(4-cyclopropylmethanesulfonylphenyl) acetamido]-N-phenylbenzamide;

N-tert-butyl-4-{2-[4-(cyclopropylsulfamoyl)phenyl]acetamido}-N-phenylbenzamide;

4-{2-[4-(cyclopropylsulfamoyl)phenyl]acetamido}-N-(4-methylphenyl)-N-[2-(oxolan-2-yl)propan-2-yl]benzamide;

4-[2-(4-cyclopropylmethanesulfonylphenyl)acetamido]-N-(4-methylphenyl)-N-[2-(oxolan-2-yl)propan-2-yl]benzamide;

N-tert-butyl-4-[2-(4-cyclopropylmethanesulfonylphenyl) acetamido]-3-fluoro-N-phenylbenzamide;

4-[2-(4-cyclopropylmethanesulfonylphenyl)acetamido]-N-[2-(oxolan-2-yl)propan-2-yl]-N-phenylbenzamide;

4-[2-(4-cyclopropylmethanesulfonylphenyl)acetamido]-N-(oxolan-3-yl)-N-(pyridin-2-yl)benzamide;

N-cyclopropyl-4-[2-(4-cyclopropylmethanesulfonylphenyl)acetamido]-N-(pyridin-2-yl)benzamide;

4-[2-(4-cyclopropylmethanesulfonylphenyl)acetamido]-N-(1-hydroxy-2-methylpropan-2-yl)-N-phenylbenzamide;

N-cyclobutyl-4-[2-(4-cyclopropylmethanesulfonylphenyl)acetamido]-N-(pyridin-2-yl)benzamide;

N-cyclopropyl-4-[2-(4-cyclopropylmethanesulfonylphenyl)acetamido]-N-phenylbenzamide;

N-cyclobutyl-4-[2-(4-cyclopropylmethanesulfonylphenyl)acetamido]-N-phenylbenzamide;

4-[2-(4-cyclopropylmethanesulfonylphenyl)acetamido]-N-(1-methylcyclopropyl)-N-phenylbenzamide;

N-cyclopropyl-4-[2-(4-cyclopropylmethanesulfonylphenyl)acetamido]-N-(pyridin-3-yl)benzamide;

4-[2-(4-cyclopropylmethanesulfonylphenyl)acetamido]-N-(3,3-difluorocyclobutyl)-N-phenylbenzamide;

methyl 2-(1-{4-[2-(4-cyclopropylmethanesulfonylphenyl)acetamido]phenyl}-N-phenylformamido)-2-methylpropanoate;

4-[2-(4-cyclopropylmethanesulfonylphenyl)acetamido]-N-phenyl-N-(1,1,1-trifluoropropan-2-yl)benzamide;

4-[2-(4-cyclopropylmethanesulfonylphenyl)acetamido]-N-(2,6-dichlorophenyl)benzamide;

4-{2-[4-(cyclopropylsulfamoyl)phenyl]acetamido}-N-phenyl-N-(1,1,1-trifluoropropan-2-yl)benzamide;

4-[2-(4-cyclopropylmethanesulfonylphenyl)acetamido]-N-(oxetan-3-yl)-N-phenylbenzamide;

N-(4-(7-oxa-4-azaspiro[2.5]octane-4-carbonyl)phenyl)-2-(4-((cyclopropylmethyl)sulfonyl)phenyl)acetamide;

N-(tert-butyl)-4-(2-(4-((cyclopropylmethyl)sulfonyl)phenyl)acetamido)-N-(2-hydroxyethyl)benzamide;

4-(2-(4-((cyclopropylmethyl)sulfonyl)phenyl)acetamido)-N-(2-hydroxyethyl)-N-isobutylbenzamide;

4-[2-(4-cyclopropylmethanesulfonylphenyl)acetamido]-N-(1-hydroxy-2-methylpropan-2-yl)-N-(4-methylphenyl)benzamide;

4-{2-[4-(cyclopropylsulfamoyl)phenyl]acetamido}-N-(1-hydroxy-2-methylpropan-2-yl)-N-(4-methylphenyl)benzamide;

4-[2-(6-cyclopropylmethanesulfonylpyridin-3-yl)acetamido]-N-phenyl-N-(2,2,2-trifluoroethyl)benzamide;

4-[2-(6-cyclopropylmethanesulfonylpyridin-3-yl)acetamido]-N-ethyl-2-fluoro-N-phenylbenzamide;

2-chloro-4-[2-(6-cyclopropylmethanesulfonylpyridin-3-yl)acetamido]-N-ethyl-N-phenylbenzamide;

N-tert-butyl-4-[2-(6-cyclopropylmethanesulfonylpyridin-3-yl)acetamido]-N-phenylbenzamide;

N-tert-butyl-4-[2-(6-cyclopropylmethanesulfonylpyridin-3-yl)acetamido]-3-fluoro-N-phenylbenzamide;

4-[2-(6-cyclopropylmethanesulfonylpyridin-3-yl)acetamido]-N-[2-(oxolan-2-yl)propan-2-yl]-N-phenylbenzamide;

4-[2-(6-cyclopropylmethanesulfonylpyridin-3-yl)acetamido]-N-(1-hydroxy-2-methylpropan-2-yl)-N-(4-methylphenyl)benzamide;

4-[2-(4-cyclopropylmethanesulfonylphenyl)acetamido]-N-ethyl-2-methyl-N-phenylbenzamide;

4-[2-(4-cyclopropylmethanesulfonylphenyl)acetamido]-N,2-dimethyl-N-(2-methylphenyl)benzamide;

4-[2-(4-cyclopropylmethanesulfonylphenyl)acetamido]-N-(2,3-dimethylphenyl)-N-ethyl-2-methylbenzamide;

4-[2-(4-cyclopropylmethanesulfonylphenyl)acetamido]-N-(2-fluorophenyl)-N,2-dimethylbenzamide and N-(2-chlorophenyl)-4-[2-(4-cyclopropylmethanesulfonylphenyl) acetamido]-N-ethyl-2-methylbenzamide.

12. A pharmaceutical composition, which comprises a compound of Formula I according to claim 1 or a pharmaceutically acceptable salt thereof and one or more pharmaceutically acceptable excipients.

13. The pharmaceutical composition according to claim 12, which further comprises at least one additional therapeutically active agent.

14. A pharmaceutical composition, which comprises a compound according to claim 11 or a pharmaceutically acceptable salt thereof and one or more pharmaceutically acceptable excipients.

15. The pharmaceutical composition according to claim 14, which further comprises at least one additional therapeutically active agent.

* * * * *